US008906635B2

(12) United States Patent
Jin et al.

(10) Patent No.: US 8,906,635 B2
(45) Date of Patent: Dec. 9, 2014

(54) METHODS OF DIAGNOSING *CLOSTRIDIUM DIFFICILE* INFECTION

(75) Inventors: Jian-Ping Jin, Northbrook, IL (US); Lance R. Peterson, Winnetka, IL (US)

(73) Assignee: Northshore University Healthsystem, Evanston, IL (US)

( * ) Notice: Subject to any disclaimer, the term of this patent is extended or adjusted under 35 U.S.C. 154(b) by 0 days.

(21) Appl. No.: 13/978,965

(22) PCT Filed: Feb. 23, 2012

(86) PCT No.: PCT/US2012/026346
§ 371 (c)(1),
(2), (4) Date: Oct. 8, 2013

(87) PCT Pub. No.: WO2012/118693
PCT Pub. Date: Sep. 7, 2012

(65) Prior Publication Data
US 2014/0038184 A1 Feb. 6, 2014

Related U.S. Application Data

(60) Provisional application No. 61/447,225, filed on Feb. 28, 2011.

(51) Int. Cl.
*G01N 33/569* (2006.01)
*C12Q 1/68* (2006.01)
(52) U.S. Cl.
CPC .......... *G01N 33/56911* (2013.01); *C12Q 1/689* (2013.01); *G01N 2333/33* (2013.01); *Y10S 435/81* (2013.01)
USPC .......................... 435/7.32; 435/7.92; 435/810
(58) Field of Classification Search
CPC ...................... G01N 2333/33; G01N 33/56911
USPC ................................................ 435/7.32, 7.92
See application file for complete search history.

(56) References Cited

U.S. PATENT DOCUMENTS

| | | |
|---|---|---|
| 4,816,567 A | 3/1989 | Cabilly et al. |
| 5,085,862 A | 2/1992 | Klein et al. |
| 5,221,618 A | 6/1993 | Klein et al. |
| 5,244,657 A | 9/1993 | Klein et al. |
| 5,332,583 A | 7/1994 | Klein et al. |
| 5,358,868 A | 10/1994 | Klein et al. |
| 5,433,945 A | 7/1995 | Klein et al. |
| 5,545,806 A | 8/1996 | Lonberg et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,770,429 A | 6/1998 | Lonberg et al. |
| 5,789,650 A | 8/1998 | Lonberg et al. |
| 5,814,318 A | 9/1998 | Lonberg et al. |
| 5,874,299 A | 2/1999 | Lonberg et al. |
| 5,877,397 A | 3/1999 | Lonberg et al. |
| 8,257,709 B2 * | 9/2012 | Ambrosino et al. ....... 424/141.1 |
| 2004/0137601 A1 | 7/2004 | Von Eichel-Streiber et al. |
| 2005/0287150 A1 | 12/2005 | Ambrosino et al. |

FOREIGN PATENT DOCUMENTS

| | | |
|---|---|---|
| WO | WO-92/03918 A1 | 3/1992 |
| WO | WO-93/01227 A1 | 1/1993 |
| WO | WO-94/25585 A1 | 11/1994 |
| WO | WO-98/24884 A1 | 6/1998 |
| WO | WO-01/14424 A2 | 3/2001 |

OTHER PUBLICATIONS

Lederman et al (Molecular Immunology 28:1171-1181, 1991.*
James J. Storhoff , SBIR, Award ID 85313, 2007.*
Jin et al , S3:3 American Society for Microbiology conference 2008, p. 13 out of 66 pages.*
Bermudez-Humaran, *Lactococcus lactis* as a live vector for mucosal delivery of therapeutic proteins, *Hum. Vacc.* 5:264-7 (2009).
Bird et al., Single-chain antigen-binding proteins, *Science* 242:423-6 (1988).
Bowie et al., Deciphering the message in protein sequences: tolerance to amino acid substitutions, *Science* 247:1306-10 (1990).
Brodeur et al., Mouse—human myeloma partners for the production of heterohybridomas, Monoclonal Antibody Production Techniques and Applications, pp. 51-63 (Marcel Dekker, Inc., New York, 1987).
Chen et al, B cell development in mice that lack one or both immunoglobulin kappa light chain genes, *EMBO J.* 12:821-30 (1993).
Chen et al., A mouse model of *Clostridium difficile*-associated disease, *Gastroenterol.* 135:1984-92 (2008).
Choi et al., Transgenic mice containing a human heavy chain immunoglobulin gene fragment cloned in a yeast artificial chromosome, *Nature Genetics* 4:117-23 (1993).
Chothia et al., Canonical structures for the hypervariable regions of immunoglobulins, *J. Mol. Biol.* 196:901-17 (1987).
Dove et al., Molecular characterization of the *Clostridium difficile* toxin A gene, *Infect. Immun.* 58:480-8 (1990).
Fishwild et al., High-avidity human IgG kappa monoclonal antibodies from a novel strain of minilocus transgenic mice, *Nature Biotechnology* 14:845-51 (1996).
GenBank Accession No. AAA23283, Toxin A [[*Clostridium*] difficile], dated May 24, 1993.
GenBank Accession No. X53138.1, *Clostridium difficile* toxB gene for toxin B, dated Apr. 18, 2005.
Hossain et al., h2-Calponin is regulated by mechanical tension and modifies the function of actin cytoskeleton, *J. Biol. Chem.* 280:42442-53 (2005).

(Continued)

*Primary Examiner* — Padma V Baskar
(74) *Attorney, Agent, or Firm* — Marshall, Gerstein & Borun LLP

(57) ABSTRACT

Methods of diagnosing *Clostridium difficile* infection and compounds used in the methods are provided. The diagnostic methods are specific and sensitive methods for detecting a host cell response and, in some aspects, a target response, i.e. a *Clostridium difficile* toxin, in an individual infected with *Clostridium difficile*. The methods comprise detecting in a stool specimen or fluid exposed to the stool specimen a *Clostridium difficile* toxin, or a fragment thereof, and an increase in a colonic epithelial cell protein exemplified by a non-muscle tropomyosin. Also provided are kits comprising reagents for detecting host cell proteins and *Clostridium difficile* toxins.

16 Claims, 7 Drawing Sheets

(56) References Cited

OTHER PUBLICATIONS

Huston et al., Protein engineering of antibody binding sites: recovery of specific activity in an anti-digoxin single-chain Fv analogue produced in *Escherichia coli*, *Proc. Natl. Acad. Sci. USA* 85:5879-83 (1988).
Kohler et al., Continuous cultures of fused cells secreting antibody of predefined specificity, *Nature* 256:495-7 (1975).
Kozbor, A human hybrid myeloma for production of human monoclonal antibodies, *J. Immunol.* 133:3001 (1984).
Lin et al., Differential localization of tropomyosin isoforms in cultured nonmuscle cells, *J. Cell Biol.* 107:563-72 (1988).
Lonberg et al., Antigen-specific human antibodies from mice comprising four distinct genetic modifications, *Nature* 368:856-9 (1994).
Lonberg et al., Human antibodies from transgenic mice, *Intern. Rev. Immunol.* 13:65-93 (1995).
Lyras et al, Toxin B is essential for virulence of *Clostridium difficile*, *Nature* 458:1176-9 (2009).
Marks et al., By-passing immunization, *J. Mol. Biol.* 222:581-97 (1991).
Mirza et al., Autoimmunity against human tropomyosin isoforms in ulcerative colitis: localization of specific human tropomyosin isoforms in the intestine and extraintestinal organs, *Inflam. Bowel Dis.* 12(11):1036-43 (2006).
Munson et al., Ligand: a versatile computerized approach for characterization of ligand-binding systems, *Anal. Biochem.* 107:220 (1980).
Murray et al., Truncation in the tcdC region of the *Clostridium difficile* PathLoc of clinical isolates does not predict increased biological activity of Toxin B or Toxin A, *BMC Infectious Diseases* 9:103 (2009).
Needleman et al., A general method applicable to the search for similarities in the amino acid sequence of two proteins, *J. Mol. Biol.* 48:444-53 (1970).
Novy et al., In vitro functional characterization of bacterially expressed human fibroblast tropomyosin isoforms and their chimeric mutants, *Cell Motil. Cytoskeleton* 26:248-61 (1993).
Perry et al., Vertebrate tropomyosin: distribution, properties and function, *J. Muscle Res. Cell Motif.* 22:5-49 (2001).
Peterson et al., Detection of toxigenic *Clostridium difficile* in stool samples by real-time polymerase chain reaction for the diagnosis of *C. difficile*-associated diarrhea, *Clin. Infect. Dis.* 45:1152-60 (2007).
Rolfe et al., Purification and characterization of *Clostridium difficile* toxin, *Infection and Immunity* 25:191-201 (1979).
Scatchard, The attractions of proteins for small molecules and ions, *Ann. N.Y. Acad. Sci.* 51:660-72 (1949).
Shen et al., *Clostridium difficile* infection in patients with ileal pouch-anal anastomosis, *Clin. Gastroenterol. Hepatol.* 6(7):782-8 (2008).
Steidler et al., Treatment of murine colitis by *Lactococcus lactis* secreting interleukin-10, *Science* 289(5483):1352-5 (2000).
Stubbe et al., Polymeric IgA is superior to monomeric IgA and IgG carrying the same variable domain in preventing *Clostridium difficile* toxin A damaging of T84 monolayers, *J. Immunol.* 164:1952-60 (2000).
Taylor et al., A transgenic mouse that expresses a diversity of human sequence heavy and light chain immunoglobulins, *Nucl. Acids Res.* 20:6287-95 (1992).
Taylor et al., Human immunoglobulin transgenes undergo rearrangement, somatic mutation and class switching in mice that lack endogenous IgM, *Internl. Immunol.* 6: 579-91 (1994).
Tuaillon et al., Human immunoglobulin heavy-chain minilocus recombination in transgenic mice: gene-segment use in mu and gamma transcripts, *Proc. Natl. Acad. Sci. USA* 90:3720-4 (1993).
van Asseldonk et al., Cloning of usp45, a gene encoding a secreted protein from *Lactococcus lactis* subsp. *lactis* MG1363, *Gene* 95:155-60 (1990).
Ward et al., Binding activities of a repertoire of single immunoglobulin variable domains secreted from *Escherichia coli*, *Nature* 341:544-6 (1989).
Warren et al., Forced expression of chimeric human fibroblast tropomyosin mutants affects cytokinesis, *J. Cell Biol.* 129:697-708 (1995).
Yu et al, A proteolytic NH2-terminal truncation of cardiac troponin I that is up-regulated in simulated microgravity, *J. Biol. Chem.* 276:15753-60 (2001).
International Search Report and Written Opinion of the International Searching Authority, United States Patent Office, PCT/US2012/26346, dated Jun. 5, 2012.

\* cited by examiner

```
  1    MSLISKEELIKLAY-SIRPRENEYKTILTNLDEYNKLTTNNENKYLQIKKLNESIDVFMNKYKTSSRNRALSNLKKDILKEVILIKNSNTSPVEKNLHF
  1    MSLVNRKQLEKMANVRFRTQEDEYVAILDALEEYHNMSENTVVEKYLKLKDINSLTDIYIDTYKKSGRNKALKKFKEYLVTEVLELKNNNLTPVEKNLHF

100    VWIGGEVSDIALEYIKQWADINAEYNIKLWYDSEAFLVNTLKKAIVESSTTEALQLLEEEIQNPQFDNMKFYKKRMEFIYDRQKRFINYYKSQINKPTVP
101    MSLVNRKQLEKMANVRFRTQEDEYVAILDALEEYHNMSENTVVEKYLKLKDINSLTDIYIDTYKKSGRNKALKKFKEYLVTEVLELKNNNLTPVEKNLHF

200    TIDDIIKSHLVSEYNRDETVLESYRTNSLRKINSNHGIDIRANSLFTEQELLNIYSQELLNRGNLAAASDIVRLLALKNFGGVYLDVDMLPGIHSDLFKT
201    VWIGGQINDTAINYINQWKDVNSDYNVNVFYDSNAFLINTLKKTVVESAINDTLESFRENLNDPRFDYNKFFRKRMEIIYDKQKNFINYYKAQREENPEL

300    ISRPSSIGLDRWEMIKLEATMKYKKYINNYTSENFDKLDQQLKDNFKLIIESKSEKSEIFSKLENLNVSDLEIKIAFALGSVINQALISKQGSYLTNLVI
301    IEKPSSVTVDFWEMTKLEAIMKYKEYIPEYTSEHFDMLDEEVQSSFESVLASKSDKSEIFSSLGDMEASPLEVKIAFNSKGIINQGLISVKDSYCSNLIV

400    EQVKNRYQFLNQHLNPAIESDNNFTDTTKIFHDSLFNSATAENSMFLTKIAPYLQVGFMPEARSTISLSGPGAYASAYYDFINLQENTIEKTLKASDLIE
401    KQIENRYKILNNSLNPAISEDNDFNTTTNTFIDSIMAEANADNGRFMMELGKYLRVGFFPDVKTTINLSGPEAYAAAYQDLLMFKEGSMNIHLIEADLRN

500    FKFPENNLSQLTEQEINSLWSFDQASAKYQFEKYVRDYTGGSLSEDNGVDFNKNTALDKNYLLNNKIPSNNVEEAGSKNYVHYIIQLQGDDISYEATCNL
501    FEISKTNISQSTEQEMASLWSFDDARAKAQFEEYKRNYFEGSLGEDDNLDFSQNIVDKEYLLE-KISS--LARSSERGYIHYIVQLQGDKISYEAACNL

600    FSKNPKNSIIIQRNMNESAKSYFLSDDGESILELNKYRIPERLKNKEKVKVTFIGHGKDEFNTSEFARLSVDSLSNEISSFLDTIKLDISPKNVEVNLLG
598    FAKTPYDSVLFQKNIEDSEIAYYNPGDGEIQEIDKYKIPSIISDRPKIKLTFIGHGKDEFNTDIFAGFDVDSLSTEIEAAIDLAKEDISPKSIEINLLG

700    CNMFSYDFNVEETYPGKLLLSIMDKITSTLPDVNKNSITIGANQYEVRINSEGRKELLAHSGKWINKEEAIMSDLSSKEYIFFDSIDNKLKAKSKNIPGL
698    CNMFSYSINVEETYPGKLLLKVKDKISELMPSISQDSIIVSANQYEVRINSEGRRELLDHSGEWINKEESIIKDISSKEYISFNPKENKITVKSKNLPEL

800    ASISEDIKTLLLLDASVSPDTKFILNNLKLNIESSIGDYIIYYEKLEPVKNIIHNSIDDLIDEFNLLENVSDELYELKLNNLDEKYLISFEDISKNNSTYS
798    STLLQEIRNNSNSSDIELEEKVMLTECEINVISNIDTQIVEERIEEAKNLTSDSINYIKDEFKLIESISDALCDLKQQNELEDSHFISFEDISETDEGFS

900    VRFINKSNGESVYVETEKEIFSKYSEHITKEISTIKNSIITDVNGNLLDNIQLDHTSQVNTLNAAFFIQSLIDYSSNKDVLNDLSTSVKQLYAQLFSTG
898    IRFINKETGESIFVETEKTIFSEYANHITEEISIKIKGTIFDTVNGKLVKKVNLDTTHEVNTLNAAFFIQSLIEYNSSKESLSNLSVAMKVQVYAQLFSTG

1000   LNTIYDSIQLVNLISNAVNDTINVLPTITEGIPIVSTILDGINLGAAIKELLDEHDPLLKKELEAKVGVLAINMSLSTAATVASIVGIGAEVTIFLLPIA
998    LNTITDAAKVVELVSTALDETIDLLPTLSEGLPIIATIIDGVSLGAAIKELSETSDPLLRQEEAKIGIMAVNLTTATTAITTSSLGIASGFSILLVPLA

1100   GISAGIPSLVNNELILHDKATSVVNYFNHLSESKKYGPLKTEDDKILVPIDDLVISEIDFNNNSIKLGTCNILAMEGGSGHTVTGNIDHFFSSPSISSHI
1098   GISAGIPSLVNNELVLRDKATKVVDYFKHVSLVETEGVFTLLDDKIMMPQDDLVISEIDFNNNSIVLGKCEIWRMEGGSGHTVTDDIDHFFSAPSITYRE
```

Figure 1A

```
1200  PSLSIYSAIGIETENLDFSKKIMMLPNAPSRVFWWETGAVPGLRSLENDGTRLLDSIRDLYPGKFYWRFYAFF-DYAITTLKPVYEDTNIKIKLDKDTRN
1198  PHLSIYDVLEVQKEELDLSKDLMVLPNAPNRVFAWETGWTPGLRSLENDGTKLLDRIRDNYEGEFYWRYFAFIADALITTLKPRYEDTNIRINLDSNTRS

1299  FIMPTITTNEIRNKLSYSFDGAGGTYSLLLSSYPISTNINLSKDDLWIFNIDNEVREISIENGTIKKGKLIKDVLSKIDINKNKLIIGNQTIDFSGDIDN
1298  FIVPITTEYIREKLSYSFYGSGGTYALSLSQYNMGINIELSESDVWIIDVDNVVRDVTIESDKIKKGDLIEGILSTLSIEENKIILNSHEINFSGEVNG

1399  KDRYIFLTCELDDKISLIIEINLVAKSYSLLLSGDKNYLISNLSNIIEKINTLGLDS---KNIAYNYTDESNNK--YFGAISKTS-----QKSIIH--
1389  SNGFVSLTFSLEGINAIIEVDLLSKSYKLLISGELKILMLNSNHIQQKIDYIGFNSELQKNIPYSFVDSEGKENGFINGSTKEGLFVSELPDVVLISKV

1485  YKKDSKNILEFYNDSTLEFNSKDFIAEDINVFMKDDINTITGKYYVDNNTDKSIDFSISLVSKNQVKVNGLYLNESVYSSYLDFVKNSDGHHNTSNFMNL
1498  YMDDSKPSFGYYSNNL------KDVKVITKDNVNILTG--YYLKDDI--KISLSLTLQDEKTIKLNSVHLDESGVAELKFMNRKGNTNTSDSLMS-

1585  FLDNISFWKLF-GF--ENINFVIDKYFTLVGKTNLGYVEFICDNNKNIDIYFGEWKTSSSKSTIFSGNGRNVVVEPIYNPDTGEDISTSL-DFSYEPLYG
1584  FLESMNIKSIFVNFLQSNIKFILDANFIISGTTSIGQFEFICDENDNIQPYFIKFNTLETNYTLYVGNRQNMIVEPNYDLDDSGDISSTVINFSQKYLYG

1681  IDRYINKVLIAPDLYTSLININTNYYSNEYYPEIIVLNPNTFHKKVNINLDSSSFEYKWSTEGSDFILVRYLEESNKKILQKIRIKGILSNTQSFNKMSI
1684  IDSCVNKVVISPNIYTDEINITPVYETNNTYPEVIVLDANYINEKINVNINDLSIRYVWSNDGNDFILMS-TSEENKVSQVKIRFVNVFKDKTLANKLSF

1781  DFKDIKKLSLGYIMSNFKSFNSENELDRDHLGFKIIDNKTYYDEDSKLVKGLININNSLFYFDPIEFNLVTGWQTINGKKYYFD-INTGAALTSYKIIN
1783  NFSDKQDVPVSEIILSFTPSYYEDGLIGYDLGLVSLYNEKFYINNFGMMVSGLIYINDSLYYFKPPVNNLIIGFVTVGDDKYYFNPINGGAASIGETIID

1880  GKHFYFNNDGVMQLGVFKGPDGFEYFAPANTQNNNIEGQAIVYQSKFLTLNGKKYYFDNDSKAVTGWRIINNEKYYFNPNNAIAAYGLQVIDNKYYFNP
1883  DKNYYFNQSGVLQTGVFSTEDGFKYFAPANTLDENLEGEAIDFTGK-LIIDENIYYFDDNYRGAVEWKELDGEMHYFSPETGKAFKGLNQIGDDKYYFNS

1980  DTAIISKGWQTVNGSRYYFDTDTAIAFNGYKTIDGKHFYFDSDCVVKIGVFSTSNGFEYFAPANTYNNNIEGQAIVYQSKFLTLNGKKYYFDNNSKAVTG
1982  D-GVMQKGFVSINDNKHYFD-DSGVMKVGYTEIDGKHFYFAENGEMQIGVFNTEDGFKYFAHHNEDLGNEEGEEISYSG-ILNFNNKIYYFDDSFTAVVG

2080  WQTIDSKKYYFNTNTAEAATGWQTIDGKKYYFNTNTAIASTGYTIINGKHFYFNTDGIMQIGVFKGPNGFEYFAPANTD
2079  WKDLE------DGSKYYFSDS------YI-----GLSLINDGQYYFNDDGIMQVG--

2180  ANNIEGQAILYQNEFLTLNGKKYYFGSDSKAVTGWRIINNKKYYFNPNNAIAAIHLCTINNDKYYFSYDGILQNGYITIERNNFYFDANNESKMVTGVFK
2121  ------FVTINDKVFYFSDS---------GIIESGVQNIDDNYFYID--DNGIVQIGVFD

2280  GPNGFEYFAPANTHNNNIEGQAIVYQNKFLTLNGKKYYFDNDSKAVTGWQTIDGKKYYFNLNTAEAATGWQTIDGKYY
2164  TSDGYKYFAPANTVNDNIYGQAVEY-SGLVRVGEDVYYFGETYTIETGW------IYDMEN------ESDKYYFNPETKKACKGINLIDDIKYY
```

Figure 1B

```
2380 FNTNTFIASTGYTSINGKHFYFNTDGIMQIGVFKGPNGFEYFAPANTHNNNIEGQAILYQNKFLTLNGKKYYFGSDSKAVTGLRTIDGKKYYFNTNTAVA
2245 FDEKG-IMRTGLISFENNNYYFNENGEMQFG---------------------------------------------------------------------

2480 VTGWQTINGKKYYFNTNTSIASTGYTIISGKHFYFNTDGIMQIGVFKGPDGFEYFAPANTDANNIEGQAIRYQNRFLYLHDNIYYFGNNSKAATGWVTID
2275 ------------------------YINIEDKMFYFGEDGVMQIGVFNTPDGFKYFAHQNTLDENFEGESINY---------------------TGWLDLD

2580 GNRYYFEPNTAMGANGYKTIDNKNFYFRNGLPQIGVFKGSNGFEYFAPANTDANNIEGQAIRYQNRFLHLLGKIYYFGNNSKAVTGWQTINGKVYYFMPD
2230 -------------------------------------------EYIAA------------------------------------TGSVIIDGEEYYFDPD

2680 TAMAAAGGLFEIDGVIYFFGVDGVKAPGIYG       Toxin A
2359 TAQLV-----------------------ISE       Toxin B
```

The sequence of CDB=C250 is underlined

Toxin A - SEQ ID NO: 14
Toxin B - SEQ ID NO: 1

Figure 1C

Sequence repeats:

MQVGFVTINDKVFYFSDSGIIES (SEQ ID NO: 3)
GVQNIDDNYFYIDDNGIVQI (SEQ ID NO: 4)
GVFDTSDGYKYFAPANTVNDNIYGQAVEYS (SEQ ID NO: 5)
GLVRVGEDVYYFGETYTIET (SEQ ID NO: 6)
GWIYDMENESDKYYFNPETKKACK (SEQ ID NO: 7)
GINLIDDIKYYFDEKGIMRT (SEQ ID NO: 8)
GLISFENNNYYFNENGEMQF (SEQ ID NO: 9)
GYINIEDKMFYFGEDGVMQI (SEQ ID NO: 10)
GVFNTPDGFKYFAHQNTLDENFE (SEQ ID NO: 11)
GESINYTGWLDLDEKRYYFTDEYIAAT (SEQ ID NO: 12)
GSVIIDGEEYYFDPDTAQLVISE (SEQ ID NO: 13)

CDR1

```
                                                    10            20            30            40
                          ----+----|----+----|----+----|----+----|----+----|----+----|----+----|----+----|
Consensus         ---LEESG:ELVKPGASVKISCKXSGYXFTSYTMHWVKQSPGKGLEWIG
1C11 IgG1 HC.pro  ---LEESGAELVKPGASVKLSCTTSGFNIKDTYIHWMKQRPEQGLEWIG
3E1  IgG1 HC.pro  EVKLEESG:ELVKPGASVKISCKTSGYTFTEYTMHWVKQSHGKSLEWIG
3G8  IgG2b HC.pro -VQLEESG:ELVKPGTSVKMSCKASGYTFTSYVMHWVKQKPGQGLEWIG
3H10 IgG1 HC.pro  ----EESG:ELVKPGASMKISCKASGYSFTGYTMNWVKQSHGKNLEWIG
4B3  IgG1 HC.pro  ---EESG:DLVAPSQSLSITCTVSGFSLTSYGVHWVRQPPGKGLEWLV
```

CDR2                                                                                        CDR3

```
                     50            60            70            80            90           100           110
                  ----+----|----+----|----+----|----+----|----+----|----+----|----+----|----+----|
Consensus         XIIPYNGGTXYNQKFKGKATLTVDKSSSTAYMELSSLTSEDSAVYYCARSTX-RXXDXW----       (SEQ ID NO: 60)
1C11 IgG1 HC.pro  RIDPANGNTKYDPKFQDRATITADTSSNTAYLHLSSLTSEDTAVYYCARSTG-WYFDVWGAGP       (SEQ ID NO: 15)
3E1  IgG1 HC.pro  GIIPNNGGTSYNQKFKGKATLTVDKSSSTAYMELRSLTSEDSAVYYCARWTT                  (SEQ ID NO: 16)
3G8  IgG2b HC.pro YINPYNDGTKYNEKFKGKATLTSDKSSSTAYMELSSLTSEDSAVYYCTRSAYYRYFDVWGA        (SEQ ID NO: 17)
3H10 IgG1 HC.pro  LIIPYNGGTSYNQKFKGKATLTVDKSSSTAYMELLSLTSEDSAVYYCARGGLRRAMDYW          (SEQ ID NO: 18)
4B3  IgG1 HC.pro  VIWT-DGSTTYNSALKSRLSISKDNSKSQVFLKMNSLQTDDTAIYYCARQRF-YAMDYW          (SEQ ID NO: 19)
```

Figure 4A

SEQUENCE LISTING

<160> NUMBER OF SEQ ID NOS: 61

<210> SEQ ID NO 1

```
<211> LENGTH: 2366
<212> TYPE: PRT
<213> ORGANISM: Clostridium difficile
<220> FEATURE:
<221> NAME/KEY: MISC_FEATURE
<223> OTHER INFORMATION: C. difficile toxin B amino acid sequence

<400> SEQUENCE: 1
```

| Met | Ser | Leu | Val | Asn | Arg | Lys | Gln | Leu | Glu | Lys | Met | Ala | Asn | Val | Arg |
|---|---|---|---|---|---|---|---|---|---|---|---|---|---|---|---|
| 1 | | | | 5 | | | | | 10 | | | | | 15 | |

| Phe | Arg | Thr | Gln | Glu | Asp | Glu | Tyr | Val | Ala | Ile | Leu | Asp | Ala | Leu | Glu |
|---|---|---|---|---|---|---|---|---|---|---|---|---|---|---|---|
| | | | 20 | | | | | 25 | | | | | 30 | | |

| Glu | Tyr | His | Asn | Met | Ser | Glu | Asn | Thr | Val | Val | Glu | Lys | Tyr | Leu | Lys |
|---|---|---|---|---|---|---|---|---|---|---|---|---|---|---|---|
| | | | 35 | | | | | 40 | | | | 45 | | | |

| Leu | Lys | Asp | Ile | Asn | Ser | Leu | Thr | Asp | Ile | Tyr | Ile | Asp | Thr | Tyr | Lys |
|---|---|---|---|---|---|---|---|---|---|---|---|---|---|---|---|
| | 50 | | | | | 55 | | | | | 60 | | | | |

| Lys | Ser | Gly | Arg | Asn | Lys | Ala | Leu | Lys | Lys | Phe | Lys | Glu | Tyr | Leu | Val |
|---|---|---|---|---|---|---|---|---|---|---|---|---|---|---|---|
| 65 | | | | | 70 | | | | | 75 | | | | | 80 |

| Thr | Glu | Val | Leu | Glu | Leu | Lys | Asn | Asn | Leu | Thr | Pro | Val | Glu | Lys | |
|---|---|---|---|---|---|---|---|---|---|---|---|---|---|---|---|
| | | | | 85 | | | | | 90 | | | | | 95 | |

| Asn | Leu | His | Phe | Val | Trp | Ile | Gly | Gly | Gln | Ile | Asn | Asp | Thr | Ala | Ile |
|---|---|---|---|---|---|---|---|---|---|---|---|---|---|---|---|
| | | | 100 | | | | | 105 | | | | | 110 | | |

| Asn | Tyr | Ile | Asn | Gln | Trp | Lys | Asp | Val | Asn | Ser | Asp | Tyr | Asn | Val | Asn |
|---|---|---|---|---|---|---|---|---|---|---|---|---|---|---|---|
| | | | 115 | | | | | 120 | | | | | 125 | | |

| Val | Phe | Tyr | Asp | Ser | Asn | Ala | Phe | Leu | Ile | Asn | Thr | Leu | Lys | Lys | Thr |
|---|---|---|---|---|---|---|---|---|---|---|---|---|---|---|---|
| | 130 | | | | | 135 | | | | | 140 | | | | |

| Val | Val | Glu | Ser | Ala | Ile | Asn | Asp | Thr | Leu | Glu | Ser | Phe | Arg | Glu | Asn |
|---|---|---|---|---|---|---|---|---|---|---|---|---|---|---|---|
| 145 | | | | | 150 | | | | | 155 | | | | | 160 |

| Leu | Asn | Asp | Pro | Arg | Phe | Asp | Tyr | Asn | Lys | Phe | Phe | Arg | Lys | Arg | Met |
|---|---|---|---|---|---|---|---|---|---|---|---|---|---|---|---|
| | | | | 165 | | | | | 170 | | | | | 175 | |

| Glu | Ile | Ile | Tyr | Asp | Lys | Gln | Lys | Asn | Phe | Ile | Asn | Tyr | Tyr | Lys | Ala |
|---|---|---|---|---|---|---|---|---|---|---|---|---|---|---|---|
| | | | | 180 | | | | | 185 | | | | | 190 | |

| Gln | Arg | Glu | Glu | Asn | Pro | Glu | Leu | Ile | Ile | Asp | Asp | Ile | Val | Lys | Thr |
|---|---|---|---|---|---|---|---|---|---|---|---|---|---|---|---|
| | | | 195 | | | | | 200 | | | | | 205 | | |

| Tyr | Leu | Ser | Asn | Glu | Tyr | Ser | Lys | Glu | Ile | Asp | Glu | Leu | Asn | Thr | Tyr |
|---|---|---|---|---|---|---|---|---|---|---|---|---|---|---|---|
| | 210 | | | | | 215 | | | | | 220 | | | | |

| Ile | Glu | Glu | Ser | Leu | Asn | Lys | Ile | Thr | Gln | Asn | Ser | Gly | Asn | Asp | Val |
|---|---|---|---|---|---|---|---|---|---|---|---|---|---|---|---|
| 225 | | | | | 230 | | | | | 235 | | | | | 240 |

| Arg | Asn | Phe | Glu | Glu | Phe | Lys | Asn | Gly | Glu | Ser | Phe | Asn | Leu | Tyr | Glu |
|---|---|---|---|---|---|---|---|---|---|---|---|---|---|---|---|
| | | | | 245 | | | | | 250 | | | | | 255 | |

| Gln | Glu | Leu | Val | Glu | Arg | Trp | Asn | Leu | Ala | Ala | Ala | Ser | Asp | Ile | Leu |
|---|---|---|---|---|---|---|---|---|---|---|---|---|---|---|---|
| | | | 260 | | | | | 265 | | | | | 270 | | |

| Arg | Ile | Ser | Ala | Leu | Lys | Glu | Ile | Gly | Gly | Met | Tyr | Leu | Asp | Val | Asp |
|---|---|---|---|---|---|---|---|---|---|---|---|---|---|---|---|
| | | | 275 | | | | | 280 | | | | | 285 | | |

| Met | Leu | Pro | Gly | Ile | Gln | Pro | Asp | Leu | Phe | Glu | Ser | Ile | Glu | Lys | Pro |
|---|---|---|---|---|---|---|---|---|---|---|---|---|---|---|---|
| | 290 | | | | | 295 | | | | | 300 | | | | |

| Ser | Ser | Val | Thr | Val | Asp | Phe | Trp | Glu | Met | Thr | Lys | Leu | Glu | Ala | Ile |
|---|---|---|---|---|---|---|---|---|---|---|---|---|---|---|---|
| 305 | | | | | 310 | | | | | 315 | | | | | 320 |

| Met | Lys | Tyr | Lys | Glu | Tyr | Ile | Pro | Glu | Tyr | Thr | Ser | Glu | His | Phe | Asp |
|---|---|---|---|---|---|---|---|---|---|---|---|---|---|---|---|
| | | | | 325 | | | | | 330 | | | | | 335 | |

| Met | Leu | Asp | Glu | Val | Gln | Ser | Phe | Glu | Ser | Val | Leu | Ala | Ser | | |
|---|---|---|---|---|---|---|---|---|---|---|---|---|---|---|---|
| | | | 340 | | | | | 345 | | | | | 350 | | |

| Lys | Ser | Asp | Lys | Ser | Glu | Ile | Phe | Ser | Ser | Leu | Gly | Asp | Met | Glu | Ala |
|---|---|---|---|---|---|---|---|---|---|---|---|---|---|---|---|
| | | | 355 | | | | | 360 | | | | | 365 | | |

| Ser | Pro | Leu | Glu | Val | Lys | Ile | Ala | Phe | Asn | Ser | Lys | Gly | Ile | Ile | Asn |

```
               370                 375                 380
Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
                420                 425                 430

Asp Ser Ile Met Ala Glu Ala Asn Ala Asp Asn Gly Arg Phe Met Met
                435                 440                 445

Glu Leu Gly Lys Tyr Leu Arg Val Gly Phe Phe Pro Asp Val Lys Thr
450                 455                 460

Thr Ile Asn Leu Ser Gly Pro Glu Ala Tyr Ala Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
                500                 505                 510

Glu Gln Glu Met Ala Ser Leu Trp Ser Phe Asp Asp Ala Arg Ala Lys
                515                 520                 525

Ala Gln Phe Glu Glu Tyr Lys Arg Asn Tyr Phe Glu Gly Ser Leu Gly
                530                 535                 540

Glu Asp Asp Asn Leu Asp Phe Ser Gln Asn Ile Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
                580                 585                 590

Ala Ala Cys Asn Leu Phe Ala Lys Thr Pro Tyr Asp Ser Val Leu Phe
                595                 600                 605

Gln Lys Asn Ile Glu Asp Ser Glu Ile Ala Tyr Tyr Asn Pro Gly
                610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Phe Asp Val Asp Ser Leu Ser
                660                 665                 670

Thr Glu Ile Glu Ala Ala Ile Asp Leu Ala Lys Glu Asp Ile Ser Pro
                675                 680                 685

Lys Ser Ile Glu Ile Asn Leu Leu Gly Cys Asn Met Phe Ser Tyr Ser
                690                 695                 700

Ile Asn Val Glu Glu Thr Tyr Pro Gly Lys Leu Leu Lys Val Lys
705                 710                 715                 720

Asp Lys Ile Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
                740                 745                 750

Glu Leu Leu Asp His Ser Gly Glu Trp Ile Asn Lys Glu Ser Ile
                755                 760                 765

Ile Lys Asp Ile Ser Ser Lys Glu Tyr Ile Ser Phe Asn Pro Lys Glu
                770                 775                 780

Asn Lys Ile Thr Val Lys Ser Lys Asn Leu Pro Glu Leu Ser Thr Leu
785                 790                 795                 800
```

```
Leu Gln Glu Ile Arg Asn Asn Ser Asn Ser Ser Asp Ile Glu Leu Glu
                805                 810                 815

Glu Lys Val Met Leu Thr Glu Cys Glu Ile Asn Val Ile Ser Asn Ile
                820                 825                 830

Asp Thr Gln Ile Val Glu Glu Arg Ile Glu Glu Ala Lys Asn Leu Thr
                835                 840                 845

Ser Asp Ser Ile Asn Tyr Ile Lys Asp Glu Phe Lys Leu Ile Glu Ser
850                 855                 860

Ile Ser Asp Ala Leu Cys Asp Leu Lys Gln Gln Asn Glu Leu Glu Asp
865                 870                 875                 880

Ser His Phe Ile Ser Phe Glu Asp Ile Ser Glu Thr Asp Glu Gly Phe
                885                 890                 895

Ser Ile Arg Phe Ile Asn Lys Glu Thr Gly Glu Ser Ile Phe Val Glu
                900                 905                 910

Thr Glu Lys Thr Ile Phe Ser Glu Tyr Ala Asn His Ile Thr Glu Glu
                915                 920                 925

Ile Ser Lys Ile Lys Gly Thr Ile Phe Asp Thr Val Asn Gly Lys Leu
                930                 935                 940

Val Lys Lys Val Asn Leu Asp Thr Thr His Glu Val Asn Thr Leu Asn
945                 950                 955                 960

Ala Ala Phe Phe Ile Gln Ser Leu Ile Glu Tyr Asn Ser Ser Lys Glu
                965                 970                 975

Ser Leu Ser Asn Leu Ser Val Ala Met Lys Val Gln Val Tyr Ala Gln
                980                 985                 990

Leu Phe Ser Thr Gly Leu Asn Thr  Ile Thr Asp Ala Ala  Lys Val Val
                995                 1000                1005

Glu Leu Val Ser Thr Ala Leu  Asp Glu Thr Ile Asp  Leu Leu Pro
    1010                1015                1020

Thr Leu Ser Glu Gly Leu Pro  Ile Ile Ala Thr Ile  Ile Asp Gly
    1025                1030                1035

Val Ser  Leu Gly Ala Ala Ile  Lys Glu Leu Ser Glu  Thr Ser Asp
    1040                1045                1050

Pro Leu Leu Arg Gln Glu Ile  Glu Ala Lys Ile Gly  Ile Met Ala
    1055                1060                1065

Val Asn Leu Thr Thr Ala Thr  Ala Ile Ile Thr  Ser Ser Leu
    1070                1075                1080

Gly Ile Ala Ser Gly Phe Ser  Ile Leu Leu Val Pro  Leu Ala Gly
    1085                1090                1095

Ile Ser Ala Gly Ile Pro Ser  Leu Val Asn Asn Glu  Leu Val Leu
    1100                1105                1110

Arg Asp Lys Ala Thr Lys Val  Val Asp Tyr Phe Lys  His Val Ser
    1115                1120                1125

Leu Val Glu Thr Glu Gly Val  Phe Thr Leu Leu Asp  Asp Lys Ile
    1130                1135                1140

Met Met Pro Gln Asp Asp Leu  Val Ile Ser Glu Ile  Asp Phe Asn
    1145                1150                1155

Asn Asn Ser Ile Val Leu Gly  Lys Cys Glu Ile Trp  Arg Met Glu
    1160                1165                1170

Gly Gly Ser Gly His Thr Val  Thr Asp Asp Ile Asp  His Phe Phe
    1175                1180                1185

Ser Ala Pro Ser Ile Thr Tyr  Arg Glu Pro His Leu  Ser Ile Tyr
    1190                1195                1200
```

```
Asp Val Leu Glu Val Gln Lys Glu Glu Leu Asp Leu Ser Lys Asp
    1205                1210                1215

Leu Met Val Leu Pro Asn Ala Pro Asn Arg Val Phe Ala Trp Glu
    1220                1225                1230

Thr Gly Trp Thr Pro Gly Leu Arg Ser Leu Glu Asn Asp Gly Thr
    1235                1240                1245

Lys Leu Leu Asp Arg Ile Arg Asp Asn Tyr Glu Gly Glu Phe Tyr
    1250                1255                1260

Trp Arg Tyr Phe Ala Phe Ile Ala Asp Ala Leu Ile Thr Thr Leu
    1265                1270                1275

Lys Pro Arg Tyr Glu Asp Thr Asn Ile Arg Ile Asn Leu Asp Ser
    1280                1285                1290

Asn Thr Arg Ser Phe Ile Val Pro Ile Ile Thr Thr Glu Tyr Ile
    1295                1300                1305

Arg Glu Lys Leu Ser Tyr Ser Phe Tyr Gly Ser Gly Gly Thr Tyr
    1310                1315                1320

Ala Leu Ser Leu Ser Gln Tyr Asn Met Gly Ile Asn Ile Glu Leu
    1325                1330                1335

Ser Glu Ser Asp Val Trp Ile Ile Asp Val Asp Asn Val Val Arg
    1340                1345                1350

Asp Val Thr Ile Glu Ser Asp Lys Ile Lys Lys Gly Asp Leu Ile
    1355                1360                1365

Glu Gly Ile Leu Ser Thr Leu Ser Ile Glu Glu Asn Lys Ile Ile
    1370                1375                1380

Leu Asn Ser His Glu Ile Asn Phe Ser Gly Glu Val Asn Gly Ser
    1385                1390                1395

Asn Gly Phe Val Ser Leu Thr Phe Ser Ile Leu Glu Gly Ile Asn
    1400                1405                1410

Ala Ile Ile Glu Val Asp Leu Leu Ser Lys Ser Tyr Lys Leu Leu
    1415                1420                1425

Ile Ser Gly Glu Leu Lys Ile Leu Met Leu Asn Ser Asn His Ile
    1430                1435                1440

Gln Gln Lys Ile Asp Tyr Ile Gly Phe Asn Ser Glu Leu Gln Lys
    1445                1450                1455

Asn Ile Pro Tyr Ser Phe Val Asp Ser Glu Gly Lys Glu Asn Gly
    1460                1465                1470

Phe Ile Asn Gly Ser Thr Lys Glu Gly Leu Phe Val Ser Glu Leu
    1475                1480                1485

Pro Asp Val Val Leu Ile Ser Lys Val Tyr Met Asp Asp Ser Lys
    1490                1495                1500

Pro Ser Phe Gly Tyr Tyr Ser Asn Asn Leu Lys Asp Val Lys Val
    1505                1510                1515

Ile Thr Lys Asp Asn Val Asn Ile Leu Thr Gly Tyr Tyr Leu Lys
    1520                1525                1530

Asp Asp Ile Lys Ile Ser Leu Ser Leu Thr Leu Gln Asp Glu Lys
    1535                1540                1545

Thr Ile Lys Leu Asn Ser Val His Leu Asp Glu Ser Gly Val Ala
    1550                1555                1560

Glu Ile Leu Lys Phe Met Asn Arg Lys Gly Asn Thr Asn Thr Ser
    1565                1570                1575

Asp Ser Leu Met Ser Phe Leu Glu Ser Met Asn Ile Lys Ser Ile
    1580                1585                1590

Phe Val Asn Phe Leu Gln Ser Asn Ile Lys Phe Ile Leu Asp Ala
```

-continued

```
            1595                1600                1605
Asn Phe Ile Ile Ser Gly Thr Thr Ser Ile Gly Gln Phe Glu Phe
            1610                1615                1620
Ile Cys Asp Glu Asn Asp Asn Ile Gln Pro Tyr Phe Ile Lys Phe
            1625                1630                1635
Asn Thr Leu Glu Thr Asn Tyr Thr Leu Tyr Val Gly Asn Arg Gln
            1640                1645                1650
Asn Met Ile Val Glu Pro Asn Tyr Asp Leu Asp Asp Ser Gly Asp
            1655                1660                1665
Ile Ser Ser Thr Val Ile Asn Phe Ser Gln Lys Tyr Leu Tyr Gly
            1670                1675                1680
Ile Asp Ser Cys Val Asn Lys Val Val Ile Ser Pro Asn Ile Tyr
            1685                1690                1695
Thr Asp Glu Ile Asn Ile Thr Pro Val Tyr Glu Thr Asn Asn Thr
            1700                1705                1710
Tyr Pro Glu Val Ile Val Leu Asp Ala Asn Tyr Ile Asn Glu Lys
            1715                1720                1725
Ile Asn Val Asn Ile Asn Asp Leu Ser Ile Arg Tyr Val Trp Ser
            1730                1735                1740
Asn Asp Gly Asn Asp Phe Ile Leu Met Ser Thr Ser Glu Glu Asn
            1745                1750                1755
Lys Val Ser Gln Val Lys Ile Arg Phe Val Asn Val Phe Lys Asp
            1760                1765                1770
Lys Thr Leu Ala Asn Lys Leu Ser Phe Asn Phe Ser Asp Lys Gln
            1775                1780                1785
Asp Val Pro Val Ser Glu Ile Ile Leu Ser Phe Thr Pro Ser Tyr
            1790                1795                1800
Tyr Glu Asp Gly Leu Ile Gly Tyr Asp Leu Gly Leu Val Ser Leu
            1805                1810                1815
Tyr Asn Glu Lys Phe Tyr Ile Asn Asn Phe Gly Met Met Val Ser
            1820                1825                1830
Gly Leu Ile Tyr Ile Asn Asp Ser Leu Tyr Tyr Phe Lys Pro Pro
            1835                1840                1845
Val Asn Asn Leu Ile Thr Gly Phe Val Thr Val Gly Asp Asp Lys
            1850                1855                1860
Tyr Tyr Phe Asn Pro Ile Asn Gly Gly Ala Ala Ser Ile Gly Glu
            1865                1870                1875
Thr Ile Ile Asp Asp Lys Asn Tyr Tyr Phe Asn Gln Ser Gly Val
            1880                1885                1890
Leu Gln Thr Gly Val Phe Ser Thr Glu Asp Gly Phe Lys Tyr Phe
            1895                1900                1905
Ala Pro Ala Asn Thr Leu Asp Glu Asn Leu Glu Gly Glu Ala Ile
            1910                1915                1920
Asp Phe Thr Gly Lys Leu Ile Ile Asp Glu Asn Ile Tyr Tyr Phe
            1925                1930                1935
Asp Asp Asn Tyr Arg Gly Ala Val Glu Trp Lys Glu Leu Asp Gly
            1940                1945                1950
Glu Met His Tyr Phe Ser Pro Glu Thr Gly Lys Ala Phe Lys Gly
            1955                1960                1965
Leu Asn Gln Ile Gly Asp Asp Lys Tyr Tyr Phe Asn Ser Asp Gly
            1970                1975                1980
Val Met Gln Lys Gly Phe Val Ser Ile Asn Asp Asn Lys His Tyr
            1985                1990                1995
```

-continued

Phe Asp Asp Ser Gly Val Met Lys Val Gly Tyr Thr Glu Ile Asp
2000            2005                2010

Gly Lys His Phe Tyr Phe Ala Glu Asn Gly Glu Met Gln Ile Gly
2015            2020                2025

Val Phe Asn Thr Glu Asp Gly Phe Lys Tyr Phe Ala His His Asn
2030            2035                2040

Glu Asp Leu Gly Asn Glu Glu Gly Glu Ile Ser Tyr Ser Gly
2045            2050                2055

Ile Leu Asn Phe Asn Asn Lys Ile Tyr Tyr Phe Asp Asp Ser Phe
2060            2065                2070

Thr Ala Val Val Gly Trp Lys Asp Leu Glu Asp Gly Ser Lys Tyr
2075            2080                2085

Tyr Phe Asp Glu Asp Thr Ala Glu Ala Tyr Ile Gly Leu Ser Leu
2090            2095                2100

Ile Asn Asp Gly Gln Tyr Tyr Phe Asn Asp Asp Gly Ile Met Gln
2105            2110                2115

Val Gly Phe Val Thr Ile Asn Asp Lys Val Phe Tyr Phe Ser Asp
2120            2125                2130

Ser Gly Ile Ile Glu Ser Gly Val Gln Asn Ile Asp Asp Asn Tyr
2135            2140                2145

Phe Tyr Ile Asp Asp Asn Gly Ile Val Gln Ile Gly Val Phe Asp
2150            2155                2160

Thr Ser Asp Gly Tyr Lys Tyr Phe Ala Pro Ala Asn Thr Val Asn
2165            2170                2175

Asp Asn Ile Tyr Gly Gln Ala Val Glu Tyr Ser Gly Leu Val Arg
2180            2185                2190

Val Gly Glu Asp Val Tyr Tyr Phe Gly Glu Thr Tyr Thr Ile Glu
2195            2200                2205

Thr Gly Trp Ile Tyr Asp Met Glu Asn Glu Ser Asp Lys Tyr Tyr
2210            2215                2220

Phe Asn Pro Glu Thr Lys Lys Ala Cys Lys Gly Ile Asn Leu Ile
2225            2230                2235

Asp Asp Ile Lys Tyr Tyr Phe Asp Glu Lys Gly Ile Met Arg Thr
2240            2245                2250

Gly Leu Ile Ser Phe Glu Asn Asn Asn Tyr Tyr Phe Asn Glu Asn
2255            2260                2265

Gly Glu Met Gln Phe Gly Tyr Ile Asn Ile Glu Asp Lys Met Phe
2270            2275                2280

Tyr Phe Gly Glu Asp Gly Val Met Gln Ile Gly Val Phe Asn Thr
2285            2290                2295

Pro Asp Gly Phe Lys Tyr Phe Ala His Gln Asn Thr Leu Asp Glu
2300            2305                2310

Asn Phe Glu Gly Glu Ser Ile Asn Tyr Thr Gly Trp Leu Asp Leu
2315            2320                2325

Asp Glu Lys Arg Tyr Tyr Phe Thr Asp Glu Tyr Ile Ala Ala Thr
2330            2335                2340

Gly Ser Val Ile Ile Asp Gly Glu Glu Tyr Tyr Phe Asp Pro Asp
2345            2350                2355

Thr Ala Gln Leu Val Ile Ser Glu
2360            2365

<210> SEQ ID NO 2
<211> LENGTH: 250

```
<212> TYPE: PRT
<213> ORGANISM: Clostridium difficile
<220> FEATURE:
<221> NAME/KEY: MISC_FEATURE
<223> OTHER INFORMATION: C. difficile C-terminal CDB-C250 of toxin B
      amino acid sequence

<400> SEQUENCE: 2
```

Met Gln Val Gly Phe Val Thr Ile Asn Asp Lys Val Phe Tyr Phe Ser
1               5                   10                  15

Asp Ser Gly Ile Ile Glu Ser Gly Val Gln Asn Ile Asp Asp Asn Tyr
            20                  25                  30

Phe Tyr Ile Asp Asp Asn Gly Ile Val Gln Ile Gly Val Phe Asp Thr
        35                  40                  45

Ser Asp Gly Tyr Lys Tyr Phe Ala Pro Ala Asn Thr Val Asn Asp Asn
50                  55                  60

Ile Tyr Gly Gln Ala Val Glu Tyr Ser Gly Leu Val Arg Val Gly Glu
65                  70                  75                  80

Asp Val Tyr Tyr Phe Gly Glu Thr Tyr Thr Ile Glu Thr Gly Trp Ile
                85                  90                  95

Tyr Asp Met Glu Asn Glu Ser Asp Lys Tyr Tyr Phe Asn Pro Glu Thr
            100                 105                 110

Lys Lys Ala Cys Lys Gly Ile Asn Leu Ile Asp Asp Ile Lys Tyr Tyr
        115                 120                 125

Phe Asp Glu Lys Gly Ile Met Arg Thr Gly Leu Ile Ser Phe Glu Asn
130                 135                 140

Asn Asn Tyr Tyr Phe Asn Glu Asn Gly Glu Met Gln Phe Gly Tyr Ile
145                 150                 155                 160

Asn Ile Glu Asp Lys Met Phe Tyr Phe Gly Glu Asp Gly Val Met Gln
                165                 170                 175

Ile Gly Val Phe Asn Thr Pro Asp Gly Phe Lys Tyr Phe Ala His Gln
            180                 185                 190

Asn Thr Leu Asp Glu Asn Phe Glu Gly Glu Ser Ile Asn Tyr Thr Gly
        195                 200                 205

Trp Leu Asp Leu Asp Glu Lys Arg Tyr Tyr Phe Thr Asp Glu Tyr Ile
210                 215                 220

Ala Ala Thr Gly Ser Val Ile Ile Asp Gly Glu Glu Tyr Tyr Phe Asp
225                 230                 235                 240

Pro Asp Thr Ala Gln Leu Val Ile Ser Glu
                245                 250

```
<210> SEQ ID NO 3
<211> LENGTH: 23
<212> TYPE: PRT
<213> ORGANISM: Clostridium difficile
<220> FEATURE:
<221> NAME/KEY: MISC_FEATURE
<223> OTHER INFORMATION: C. difficile C-terminal repeat A

<400> SEQUENCE: 3
```

Met Gln Val Gly Phe Val Thr Ile Asn Asp Lys Val Phe Tyr Phe Ser
1               5                   10                  15

Asp Ser Gly Ile Ile Glu Ser
            20

```
<210> SEQ ID NO 4
<211> LENGTH: 20
<212> TYPE: PRT
<213> ORGANISM: Clostridium difficile
```

```
<220> FEATURE:
<221> NAME/KEY: MISC_FEATURE
<223> OTHER INFORMATION: C. difficile C-terminal repeat B

<400> SEQUENCE: 4

Gly Val Gln Asn Ile Asp Asp Asn Tyr Phe Tyr Ile Asp Asp Asn Gly
1               5                   10                  15

Ile Val Gln Ile
            20

<210> SEQ ID NO 5
<211> LENGTH: 30
<212> TYPE: PRT
<213> ORGANISM: Clostridium difficile
<220> FEATURE:
<221> NAME/KEY: MISC_FEATURE
<223> OTHER INFORMATION: C. difficile C-terminal repeat C

<400> SEQUENCE: 5

Gly Val Phe Asp Thr Ser Asp Gly Tyr Lys Tyr Phe Ala Pro Ala Asn
1               5                   10                  15

Thr Val Asn Asp Asn Ile Tyr Gly Gln Ala Val Glu Tyr Ser
            20                  25                  30

<210> SEQ ID NO 6
<211> LENGTH: 20
<212> TYPE: PRT
<213> ORGANISM: Clostridium difficile
<220> FEATURE:
<221> NAME/KEY: MISC_FEATURE
<223> OTHER INFORMATION: C. difficile C-terminal repeat D

<400> SEQUENCE: 6

Gly Leu Val Arg Val Gly Glu Asp Val Tyr Tyr Phe Gly Glu Thr Tyr
1               5                   10                  15

Thr Ile Glu Thr
            20

<210> SEQ ID NO 7
<211> LENGTH: 24
<212> TYPE: PRT
<213> ORGANISM: Clostridium difficile
<220> FEATURE:
<221> NAME/KEY: MISC_FEATURE
<223> OTHER INFORMATION: C. difficile C-terminal repeat E

<400> SEQUENCE: 7

Gly Trp Ile Tyr Asp Met Glu Asn Glu Ser Asp Lys Tyr Tyr Phe Asn
1               5                   10                  15

Pro Glu Thr Lys Lys Ala Cys Lys
            20

<210> SEQ ID NO 8
<211> LENGTH: 20
<212> TYPE: PRT
<213> ORGANISM: Clostridium difficile
<220> FEATURE:
<221> NAME/KEY: MISC_FEATURE
<223> OTHER INFORMATION: C. difficile C-terminal repeat F

<400> SEQUENCE: 8

Gly Ile Asn Leu Ile Asp Asp Ile Lys Tyr Tyr Phe Asp Glu Lys Gly
1               5                   10                  15

Ile Met Arg Thr
            20
```

<210> SEQ ID NO 9
<211> LENGTH: 20
<212> TYPE: PRT
<213> ORGANISM: Clostridium difficile
<220> FEATURE:
<221> NAME/KEY: MISC_FEATURE
<223> OTHER INFORMATION: C. difficile C-terminal repeat G

<400> SEQUENCE: 9

Gly Leu Ile Ser Phe Glu Asn Asn Asn Tyr Tyr Phe Asn Glu Asn Gly
1               5                   10                  15

Glu Met Gln Phe
            20

<210> SEQ ID NO 10
<211> LENGTH: 20
<212> TYPE: PRT
<213> ORGANISM: Clostridium difficile
<220> FEATURE:
<221> NAME/KEY: MISC_FEATURE
<223> OTHER INFORMATION: C. difficile C-terminal repeat H

<400> SEQUENCE: 10

Gly Tyr Ile Asn Ile Glu Asp Lys Met Phe Tyr Phe Gly Glu Asp Gly
1               5                   10                  15

Val Met Gln Ile
            20

<210> SEQ ID NO 11
<211> LENGTH: 23
<212> TYPE: PRT
<213> ORGANISM: Clostridium difficile
<220> FEATURE:
<221> NAME/KEY: MISC_FEATURE
<223> OTHER INFORMATION: C. difficile C-terminal repeat I

<400> SEQUENCE: 11

Gly Val Phe Asn Thr Pro Asp Gly Phe Lys Tyr Phe Ala His Gln Asn
1               5                   10                  15

Thr Leu Asp Glu Asn Phe Glu
            20

<210> SEQ ID NO 12
<211> LENGTH: 27
<212> TYPE: PRT
<213> ORGANISM: Clostridium difficile
<220> FEATURE:
<221> NAME/KEY: MISC_FEATURE
<223> OTHER INFORMATION: C. difficile C-terminal repeat J

<400> SEQUENCE: 12

Gly Glu Ser Ile Asn Tyr Thr Gly Trp Leu Asp Leu Asp Glu Lys Arg
1               5                   10                  15

Tyr Tyr Phe Thr Asp Glu Tyr Ile Ala Ala Thr
            20                  25

<210> SEQ ID NO 13
<211> LENGTH: 23
<212> TYPE: PRT
<213> ORGANISM: Clostridium difficile
<220> FEATURE:
<221> NAME/KEY: MISC_FEATURE
<223> OTHER INFORMATION: C. difficile C-terminal repeat K

<400> SEQUENCE: 13

```
Gly Ser Val Ile Ile Asp Gly Glu Glu Tyr Tyr Phe Asp Pro Asp Thr
1               5                   10                  15

Ala Gln Leu Val Ile Ser Glu
            20
```

<210> SEQ ID NO 14
<211> LENGTH: 2710
<212> TYPE: PRT
<213> ORGANISM: Clostridium difficile
<220> FEATURE:
<221> NAME/KEY: MISC_FEATURE
<223> OTHER INFORMATION: C. difficile toxin A amino acid sequence

<400> SEQUENCE: 14

```
Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
            20                  25                  30

Tyr Asn Lys Leu Thr Thr Asn Asn Glu Asn Lys Tyr Leu Gln Leu
        35                  40                  45

Lys Lys Leu Asn Glu Ser Ile Asp Val Phe Met Asn Lys Tyr Lys Thr
50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
            100                 105                 110

Tyr Ile Lys Gln Trp Ala Asp Ile Asn Ala Glu Tyr Asn Ile Lys Leu
        115                 120                 125

Trp Tyr Asp Ser Glu Ala Phe Leu Val Asn Thr Leu Lys Lys Ala Ile
    130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175

Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Ile Lys Ser His
        195                 200                 205

Leu Val Ser Glu Tyr Asn Arg Asp Glu Thr Val Leu Glu Ser Tyr Arg
    210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
                245                 250                 255

Glu Leu Leu Asn Arg Gly Asn Leu Ala Ala Ala Ser Asp Ile Val Arg
            260                 265                 270

Leu Leu Ala Leu Lys Asn Phe Gly Gly Val Tyr Leu Asp Val Asp Met
        275                 280                 285

Leu Pro Gly Ile His Ser Asp Leu Phe Lys Thr Ile Ser Arg Pro Ser
    290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
```

-continued

```
                325                 330                 335
Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
        355                 360                 365

Asp Leu Glu Ile Lys Ile Ala Phe Ala Leu Gly Ser Val Ile Asn Gln
    370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
                405                 410                 415

Ile Glu Ser Asp Asn Asn Phe Thr Asp Thr Thr Lys Ile Phe His Asp
            420                 425                 430

Ser Leu Phe Asn Ser Ala Thr Ala Glu Asn Ser Met Phe Leu Thr Lys
        435                 440                 445

Ile Ala Pro Tyr Leu Gln Val Gly Phe Met Pro Glu Ala Arg Ser Thr
    450                 455                 460

Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
                485                 490                 495

Leu Ile Glu Phe Lys Phe Pro Glu Asn Asn Leu Ser Gln Leu Thr Glu
            500                 505                 510

Gln Glu Ile Asn Ser Leu Trp Ser Phe Asp Gln Ala Ser Ala Lys Tyr
        515                 520                 525

Gln Phe Glu Lys Tyr Val Arg Asp Tyr Thr Gly Gly Ser Leu Ser Glu
    530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Asn Val Glu Glu Ala Gly Ser
                565                 570                 575

Lys Asn Tyr Val His Tyr Ile Ile Gln Leu Gln Gly Asp Asp Ile Ser
            580                 585                 590

Tyr Glu Ala Thr Cys Asn Leu Phe Ser Lys Asn Pro Lys Asn Ser Ile
        595                 600                 605

Ile Ile Gln Arg Asn Met Asn Glu Ser Ala Lys Ser Tyr Phe Leu Ser
    610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
                645                 650                 655

Lys Asp Glu Phe Asn Thr Ser Glu Phe Ala Arg Leu Ser Val Asp Ser
            660                 665                 670

Leu Ser Asn Glu Ile Ser Ser Phe Leu Asp Thr Ile Lys Leu Asp Ile
        675                 680                 685

Ser Pro Lys Asn Val Glu Val Asn Leu Leu Gly Cys Asn Met Phe Ser
    690                 695                 700

Tyr Asp Phe Asn Val Glu Glu Thr Tyr Pro Gly Lys Leu Leu Leu Ser
705                 710                 715                 720

Ile Met Asp Lys Ile Thr Ser Thr Leu Pro Asp Val Asn Lys Asn Ser
                725                 730                 735

Ile Thr Ile Gly Ala Asn Gln Tyr Glu Val Arg Ile Asn Ser Glu Gly
            740                 745                 750
```

-continued

```
Arg Lys Glu Leu Leu Ala His Ser Gly Lys Trp Ile Asn Lys Glu Glu
        755                 760                 765
Ala Ile Met Ser Asp Leu Ser Ser Lys Glu Tyr Ile Phe Phe Asp Ser
770                 775                 780
Ile Asp Asn Lys Leu Lys Ala Lys Ser Lys Asn Ile Pro Gly Leu Ala
785                 790                 795                 800
Ser Ile Ser Glu Asp Ile Lys Thr Leu Leu Asp Ala Ser Val Ser
                    805                 810                 815
Pro Asp Thr Lys Phe Ile Leu Asn Asn Leu Lys Leu Asn Ile Glu Ser
                820                 825                 830
Ser Ile Gly Asp Tyr Ile Tyr Tyr Glu Lys Leu Glu Pro Val Lys Asn
            835                 840                 845
Ile Ile His Asn Ser Ile Asp Asp Leu Ile Asp Glu Phe Asn Leu Leu
        850                 855                 860
Glu Asn Val Ser Asp Glu Leu Tyr Glu Leu Lys Lys Leu Asn Asn Leu
865                 870                 875                 880
Asp Glu Lys Tyr Leu Ile Ser Phe Glu Asp Ile Ser Lys Asn Asn Ser
                    885                 890                 895
Thr Tyr Ser Val Arg Phe Ile Asn Lys Ser Asn Gly Glu Ser Val Tyr
                900                 905                 910
Val Glu Thr Glu Lys Glu Ile Phe Ser Lys Tyr Ser Glu His Ile Thr
            915                 920                 925
Lys Glu Ile Ser Thr Ile Lys Asn Ser Ile Ile Thr Asp Val Asn Gly
        930                 935                 940
Asn Leu Leu Asp Asn Ile Gln Leu Asp His Thr Ser Gln Val Asn Thr
945                 950                 955                 960
Leu Asn Ala Ala Phe Phe Ile Gln Ser Leu Ile Asp Tyr Ser Ser Asn
                    965                 970                 975
Lys Asp Val Leu Asn Asp Leu Ser Thr Ser Val Lys Val Gln Leu Tyr
                980                 985                 990
Ala Gln Leu Phe Ser Thr Gly Leu  Asn Thr Ile Tyr Asp  Ser Ile Gln
            995                 1000                1005
Leu Val  Asn Leu Ile Ser Asn  Ala Val Asn Asp Thr  Ile Asn Val
    1010                1015                1020
Leu Pro  Thr Ile Thr Glu Gly  Ile Pro Ile Val Ser  Thr Ile Leu
    1025                1030                1035
Asp Gly  Ile Asn Leu Gly Ala  Ala Ile Lys Glu Leu  Leu Asp Glu
    1040                1045                1050
His Asp  Pro Leu Leu Lys Lys  Glu Leu Glu Ala Lys  Val Gly Val
    1055                1060                1065
Leu Ala  Ile Asn Met Ser Leu  Ser Ile Ala Ala Thr  Val Ala Ser
    1070                1075                1080
Ile Val  Gly Ile Gly Ala Glu  Val Thr Ile Phe Leu  Leu Pro Ile
    1085                1090                1095
Ala Gly  Ile Ser Ala Gly Ile  Pro Ser Leu Val Asn  Asn Glu Leu
    1100                1105                1110
Ile Leu  His Asp Lys Ala Thr  Ser Val Val Asn Tyr  Phe Asn His
    1115                1120                1125
Leu Ser  Glu Ser Lys Lys Tyr  Gly Pro Leu Lys Thr  Glu Asp Asp
    1130                1135                1140
Lys Ile  Leu Val Pro Ile Asp  Asp Leu Val Ile Ser  Glu Ile Asp
    1145                1150                1155
```

```
Phe Asn Asn Asn Ser Ile Lys Leu Gly Thr Cys Asn Ile Leu Ala
1160                1165                1170

Met Glu Gly Gly Ser Gly His Thr Val Thr Gly Asn Ile Asp His
1175                1180                1185

Phe Phe Ser Ser Pro Ser Ile Ser Ser His Ile Pro Ser Leu Ser
1190                1195                1200

Ile Tyr Ser Ala Ile Gly Ile Glu Thr Glu Asn Leu Asp Phe Ser
1205                1210                1215

Lys Lys Ile Met Met Leu Pro Asn Ala Pro Ser Arg Val Phe Trp
1220                1225                1230

Trp Glu Thr Gly Ala Val Pro Gly Leu Arg Ser Leu Glu Asn Asp
1235                1240                1245

Gly Thr Arg Leu Leu Asp Ser Ile Arg Asp Leu Tyr Pro Gly Lys
1250                1255                1260

Phe Tyr Trp Arg Phe Tyr Ala Phe Phe Asp Tyr Ala Ile Thr Thr
1265                1270                1275

Leu Lys Pro Val Tyr Glu Asp Thr Asn Ile Lys Ile Lys Leu Asp
1280                1285                1290

Lys Asp Thr Arg Asn Phe Ile Met Pro Thr Ile Thr Thr Asn Glu
1295                1300                1305

Ile Arg Asn Lys Leu Ser Tyr Ser Phe Asp Gly Ala Gly Gly Thr
1310                1315                1320

Tyr Ser Leu Leu Leu Ser Ser Tyr Pro Ile Ser Thr Asn Ile Asn
1325                1330                1335

Leu Ser Lys Asp Asp Leu Trp Ile Phe Asn Ile Asp Asn Glu Val
1340                1345                1350

Arg Glu Ile Ser Ile Glu Asn Gly Thr Ile Lys Lys Gly Lys Leu
1355                1360                1365

Ile Lys Asp Val Leu Ser Lys Ile Asp Ile Asn Lys Asn Lys Leu
1370                1375                1380

Ile Ile Gly Asn Gln Thr Ile Asp Phe Ser Gly Asp Ile Asp Asn
1385                1390                1395

Lys Asp Arg Tyr Ile Phe Leu Thr Cys Glu Leu Asp Asp Lys Ile
1400                1405                1410

Ser Leu Ile Ile Glu Ile Asn Leu Val Ala Lys Ser Tyr Ser Leu
1415                1420                1425

Leu Leu Ser Gly Asp Lys Asn Tyr Leu Ile Ser Asn Leu Ser Asn
1430                1435                1440

Ile Ile Glu Lys Ile Asn Thr Leu Gly Leu Asp Ser Lys Asn Ile
1445                1450                1455

Ala Tyr Asn Tyr Thr Asp Glu Ser Asn Asn Lys Tyr Phe Gly Ala
1460                1465                1470

Ile Ser Lys Thr Ser Gln Lys Ser Ile Ile His Tyr Lys Lys Asp
1475                1480                1485

Ser Lys Asn Ile Leu Glu Phe Tyr Asn Asp Ser Thr Leu Glu Phe
1490                1495                1500

Asn Ser Lys Asp Phe Ile Ala Glu Asp Ile Asn Val Phe Met Lys
1505                1510                1515

Asp Asp Ile Asn Thr Ile Thr Gly Lys Tyr Tyr Val Asp Asn Asn
1520                1525                1530

Thr Asp Lys Ser Ile Asp Phe Ser Ile Ser Leu Val Ser Lys Asn
1535                1540                1545

Gln Val Lys Val Asn Gly Leu Tyr Leu Asn Glu Ser Val Tyr Ser
```

-continued

```
                 1550              1555              1560
Ser Tyr Leu Asp Phe Val Lys Asn Ser Asp Gly His His Asn Thr
    1565              1570              1575
Ser Asn Phe Met Asn Leu Phe Leu Asp Asn Ile Ser Phe Trp Lys
    1580              1585              1590
Leu Phe Gly Phe Glu Asn Ile Asn Phe Val Ile Asp Lys Tyr Phe
    1595              1600              1605
Thr Leu Val Gly Lys Thr Asn Leu Gly Tyr Val Glu Phe Ile Cys
    1610              1615              1620
Asp Asn Asn Lys Asn Ile Asp Ile Tyr Phe Gly Glu Trp Lys Thr
    1625              1630              1635
Ser Ser Ser Lys Ser Thr Ile Phe Ser Gly Asn Gly Arg Asn Val
    1640              1645              1650
Val Val Glu Pro Ile Tyr Asn Pro Asp Thr Gly Glu Asp Ile Ser
    1655              1660              1665
Thr Ser Leu Asp Phe Ser Tyr Glu Pro Leu Tyr Gly Ile Asp Arg
    1670              1675              1680
Tyr Ile Asn Lys Val Leu Ile Ala Pro Asp Leu Tyr Thr Ser Leu
    1685              1690              1695
Ile Asn Ile Asn Thr Asn Tyr Tyr Ser Asn Glu Tyr Tyr Pro Glu
    1700              1705              1710
Ile Ile Val Leu Asn Pro Asn Thr Phe His Lys Lys Val Asn Ile
    1715              1720              1725
Asn Leu Asp Ser Ser Phe Glu Tyr Lys Trp Ser Thr Glu Gly
    1730              1735              1740
Ser Asp Phe Ile Leu Val Arg Tyr Leu Glu Glu Ser Asn Lys Lys
    1745              1750              1755
Ile Leu Gln Lys Ile Arg Ile Lys Gly Ile Leu Ser Asn Thr Gln
    1760              1765              1770
Ser Phe Asn Lys Met Ser Ile Asp Phe Lys Asp Ile Lys Lys Leu
    1775              1780              1785
Ser Leu Gly Tyr Ile Met Ser Asn Phe Lys Ser Phe Asn Ser Glu
    1790              1795              1800
Asn Glu Leu Asp Arg Asp His Leu Gly Phe Lys Ile Ile Asp Asn
    1805              1810              1815
Lys Thr Tyr Tyr Tyr Asp Glu Asp Ser Lys Leu Val Lys Gly Leu
    1820              1825              1830
Ile Asn Ile Asn Asn Ser Leu Phe Tyr Phe Asp Pro Ile Glu Phe
    1835              1840              1845
Asn Leu Val Thr Gly Trp Gln Thr Ile Asn Gly Lys Lys Tyr Tyr
    1850              1855              1860
Phe Asp Ile Asn Thr Gly Ala Ala Leu Thr Ser Tyr Lys Ile Ile
    1865              1870              1875
Asn Gly Lys His Phe Tyr Phe Asn Asn Asp Gly Val Met Gln Leu
    1880              1885              1890
Gly Val Phe Lys Gly Pro Asp Gly Phe Glu Tyr Phe Ala Pro Ala
    1895              1900              1905
Asn Thr Gln Asn Asn Asn Ile Glu Gly Gln Ala Ile Val Tyr Gln
    1910              1915              1920
Ser Lys Phe Leu Thr Leu Asn Gly Lys Lys Tyr Tyr Phe Asp Asn
    1925              1930              1935
Asp Ser Lys Ala Val Thr Gly Trp Arg Ile Ile Asn Asn Glu Lys
    1940              1945              1950
```

```
Tyr Tyr Phe Asn Pro Asn Asn Ala Ile Ala Ala Tyr Gly Leu Gln
1955                1960                1965

Val Ile Asp Asn Asn Lys Tyr Tyr Phe Asn Pro Asp Thr Ala Ile
1970                1975                1980

Ile Ser Lys Gly Trp Gln Thr Val Asn Gly Ser Arg Tyr Tyr Phe
1985                1990                1995

Asp Thr Asp Thr Ala Ile Ala Phe Asn Gly Tyr Lys Thr Ile Asp
2000                2005                2010

Gly Lys His Phe Tyr Phe Asp Ser Asp Cys Val Val Lys Ile Gly
2015                2020                2025

Val Phe Ser Thr Ser Asn Gly Phe Glu Tyr Phe Ala Pro Ala Asn
2030                2035                2040

Thr Tyr Asn Asn Asn Ile Glu Gly Gln Ala Ile Val Tyr Gln Ser
2045                2050                2055

Lys Phe Leu Thr Leu Asn Gly Lys Lys Tyr Tyr Phe Asp Asn Asn
2060                2065                2070

Ser Lys Ala Val Thr Gly Trp Gln Thr Ile Asp Ser Lys Lys Tyr
2075                2080                2085

Tyr Phe Asn Thr Asn Thr Ala Glu Ala Ala Thr Gly Trp Gln Thr
2090                2095                2100

Ile Asp Gly Lys Lys Tyr Tyr Phe Asn Thr Asn Thr Ala Glu Ala
2105                2110                2115

Ala Thr Gly Trp Gln Thr Ile Asp Gly Lys Lys Tyr Tyr Phe Asn
2120                2125                2130

Thr Asn Thr Ala Ile Ala Ser Thr Gly Tyr Thr Ile Ile Asn Gly
2135                2140                2145

Lys His Phe Tyr Phe Asn Thr Asp Gly Ile Met Gln Ile Gly Val
2150                2155                2160

Phe Lys Gly Pro Asn Gly Phe Glu Tyr Phe Ala Pro Ala Asn Thr
2165                2170                2175

Asp Ala Asn Asn Ile Glu Gly Gln Ala Ile Leu Tyr Gln Asn Glu
2180                2185                2190

Phe Leu Thr Leu Asn Gly Lys Lys Tyr Tyr Phe Gly Ser Asp Ser
2195                2200                2205

Lys Ala Val Thr Gly Trp Arg Ile Ile Asn Asn Lys Lys Tyr Tyr
2210                2215                2220

Phe Asn Pro Asn Asn Ala Ile Ala Ala Ile His Leu Cys Thr Ile
2225                2230                2235

Asn Asn Asp Lys Tyr Tyr Phe Ser Tyr Asp Gly Ile Leu Gln Asn
2240                2245                2250

Gly Tyr Ile Thr Ile Glu Arg Asn Asn Phe Tyr Phe Asp Ala Asn
2255                2260                2265

Asn Glu Ser Lys Met Val Thr Gly Val Phe Lys Gly Pro Asn Gly
2270                2275                2280

Phe Glu Tyr Phe Ala Pro Ala Asn Thr His Asn Asn Asn Ile Glu
2285                2290                2295

Gly Gln Ala Ile Val Tyr Gln Asn Lys Phe Leu Thr Leu Asn Gly
2300                2305                2310

Lys Lys Tyr Tyr Phe Asp Asn Asp Ser Lys Ala Val Thr Gly Trp
2315                2320                2325

Gln Thr Ile Asp Gly Lys Lys Tyr Tyr Phe Asn Leu Asn Thr Ala
2330                2335                2340
```

Glu Ala Ala Thr Gly Trp Gln Thr Ile Asp Gly Lys Lys Tyr Tyr
2345                2350                2355

Phe Asn Leu Asn Thr Ala Glu Ala Ala Thr Gly Trp Gln Thr Ile
2360                2365                2370

Asp Gly Lys Lys Tyr Tyr Phe Asn Thr Asn Thr Phe Ile Ala Ser
2375                2380                2385

Thr Gly Tyr Thr Ser Ile Asn Gly Lys His Phe Tyr Phe Asn Thr
2390                2395                2400

Asp Gly Ile Met Gln Ile Gly Val Phe Lys Gly Pro Asn Gly Phe
2405                2410                2415

Glu Tyr Phe Ala Pro Ala Asn Thr His Asn Asn Asn Ile Glu Gly
2420                2425                2430

Gln Ala Ile Leu Tyr Gln Asn Lys Phe Leu Thr Leu Asn Gly Lys
2435                2440                2445

Lys Tyr Tyr Phe Gly Ser Asp Ser Lys Ala Val Thr Gly Leu Arg
2450                2455                2460

Thr Ile Asp Gly Lys Lys Tyr Tyr Phe Asn Thr Asn Thr Ala Val
2465                2470                2475

Ala Val Thr Gly Trp Gln Thr Ile Asn Gly Lys Lys Tyr Tyr Phe
2480                2485                2490

Asn Thr Asn Thr Ser Ile Ala Ser Thr Gly Tyr Thr Ile Ile Ser
2495                2500                2505

Gly Lys His Phe Tyr Phe Asn Thr Asp Gly Ile Met Gln Ile Gly
2510                2515                2520

Val Phe Lys Gly Pro Asp Gly Phe Glu Tyr Phe Ala Pro Ala Asn
2525                2530                2535

Thr Asp Ala Asn Asn Ile Glu Gly Gln Ala Ile Arg Tyr Gln Asn
2540                2545                2550

Arg Phe Leu Tyr Leu His Asp Asn Ile Tyr Tyr Phe Gly Asn Asn
2555                2560                2565

Ser Lys Ala Ala Thr Gly Trp Val Thr Ile Asp Gly Asn Arg Tyr
2570                2575                2580

Tyr Phe Glu Pro Asn Thr Ala Met Gly Ala Asn Gly Tyr Lys Thr
2585                2590                2595

Ile Asp Asn Lys Asn Phe Tyr Phe Arg Asn Gly Leu Pro Gln Ile
2600                2605                2610

Gly Val Phe Lys Gly Ser Asn Gly Phe Glu Tyr Phe Ala Pro Ala
2615                2620                2625

Asn Thr Asp Ala Asn Asn Ile Glu Gly Gln Ala Ile Arg Tyr Gln
2630                2635                2640

Asn Arg Phe Leu His Leu Leu Gly Lys Ile Tyr Tyr Phe Gly Asn
2645                2650                2655

Asn Ser Lys Ala Val Thr Gly Trp Gln Thr Ile Asn Gly Lys Val
2660                2665                2670

Tyr Tyr Phe Met Pro Asp Thr Ala Met Ala Ala Ala Gly Gly Leu
2675                2680                2685

Phe Glu Ile Asp Gly Val Ile Tyr Phe Phe Gly Val Asp Gly Val
2690                2695                2700

Lys Ala Pro Gly Ile Tyr Gly
2705                2710

<210> SEQ ID NO 15
<211> LENGTH: 108
<212> TYPE: PRT

```
<213> ORGANISM: Mus musculus
<220> FEATURE:
<221> NAME/KEY: MISC_FEATURE
<223> OTHER INFORMATION: 1C11 IgG1 HC.pro

<400> SEQUENCE: 15

Leu Glu Glu Ser Gly Ala Glu Leu Val Lys Pro Gly Ala Ser Val Lys
1               5                   10                  15

Leu Ser Cys Thr Thr Ser Gly Phe Asn Ile Lys Asp Thr Tyr Ile His
            20                  25                  30

Trp Met Lys Gln Arg Pro Glu Gln Gly Leu Glu Trp Ile Gly Arg Ile
        35                  40                  45

Asp Pro Ala Asn Gly Asn Thr Lys Tyr Asp Pro Lys Phe Gln Asp Arg
    50                  55                  60

Ala Thr Ile Thr Ala Asp Thr Ser Ser Asn Thr Ala Tyr Leu His Leu
65                  70                  75                  80

Ser Ser Leu Thr Ser Glu Asp Thr Ala Val Tyr Tyr Cys Ala Arg Ser
                85                  90                  95

Thr Gly Trp Tyr Phe Asp Val Trp Gly Ala Gly Pro
            100                 105

<210> SEQ ID NO 16
<211> LENGTH: 101
<212> TYPE: PRT
<213> ORGANISM: Mus musculus
<220> FEATURE:
<221> NAME/KEY: MISC_FEATURE
<223> OTHER INFORMATION: 3E1 IgG1 HC.pro

<400> SEQUENCE: 16

Glu Val Lys Leu Glu Glu Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile Ile Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Trp Thr Thr
            100

<210> SEQ ID NO 17
<211> LENGTH: 109
<212> TYPE: PRT
<213> ORGANISM: Mus musculus
<220> FEATURE:
<221> NAME/KEY: MISC_FEATURE
<223> OTHER INFORMATION: 3G8 IgG2b HC.pro

<400> SEQUENCE: 17

Val Gln Leu Glu Glu Ser Gly Pro Glu Leu Val Lys Pro Gly Thr Ser
1               5                   10                  15

Val Lys Met Ser Cys Lys Ala Ser Gly Tyr Thr Phe Thr Ser Tyr Val
            20                  25                  30

Met His Trp Val Lys Gln Lys Pro Gly Gln Gly Leu Glu Trp Ile Gly
        35                  40                  45
```

```
Tyr Ile Asn Pro Tyr Asn Asp Gly Thr Lys Tyr Asn Glu Lys Phe Lys
         50                  55                  60

Gly Lys Ala Thr Leu Thr Ser Asp Lys Ser Ser Ser Thr Ala Tyr Met
 65                  70                  75                  80

Glu Leu Ser Ser Leu Thr Ser Glu Asp Ser Ala Val Tyr Tyr Cys Thr
                 85                  90                  95

Arg Ser Ala Tyr Tyr Arg Tyr Phe Asp Val Trp Gly Ala
                100                 105
```

```
<210> SEQ ID NO 18
<211> LENGTH: 104
<212> TYPE: PRT
<213> ORGANISM: Mus musculus
<220> FEATURE:
<221> NAME/KEY: MISC_FEATURE
<223> OTHER INFORMATION: 3H10 IgG1 HC.pro

<400> SEQUENCE: 18

Glu Glu Ser Gly Pro Glu Leu Val Lys Pro Gly Ala Ser Met Lys Ile
 1               5                   10                  15

Ser Cys Lys Ala Ser Gly Tyr Ser Phe Thr Gly Tyr Thr Met Asn Trp
             20                  25                  30

Val Lys Gln Ser His Gly Lys Asn Leu Glu Trp Ile Gly Leu Ile Ile
         35                  40                  45

Pro Tyr Asn Gly Gly Thr Ser Tyr Asn Gln Lys Phe Lys Gly Lys Ala
     50                  55                  60

Thr Leu Thr Val Asp Lys Ser Ser Thr Ala Tyr Met Glu Leu Leu
 65                  70                  75                  80

Ser Leu Thr Ser Glu Asp Ser Ala Val Tyr Tyr Cys Ala Arg Gly Gly
                 85                  90                  95

Leu Arg Arg Ala Met Asp Tyr Trp
                100
```

```
<210> SEQ ID NO 19
<211> LENGTH: 101
<212> TYPE: PRT
<213> ORGANISM: Mus musculus
<220> FEATURE:
<221> NAME/KEY: MISC_FEATURE
<223> OTHER INFORMATION: 4B3 IgG1 HC.pro

<400> SEQUENCE: 19

Glu Ser Gly Pro Asp Leu Val Ala Pro Ser Gln Ser Leu Ser Ile Thr
 1               5                   10                  15

Cys Thr Val Ser Gly Phe Ser Leu Thr Ser Tyr Gly Val His Trp Val
             20                  25                  30

Arg Gln Pro Pro Gly Lys Gly Leu Glu Trp Leu Val Val Ile Trp Thr
         35                  40                  45

Asp Gly Ser Thr Thr Tyr Asn Ser Ala Leu Lys Ser Arg Leu Ser Ile
     50                  55                  60

Ser Lys Asp Asn Ser Lys Ser Gln Val Phe Leu Lys Met Asn Ser Leu
 65                  70                  75                  80

Gln Thr Asp Asp Thr Ala Ile Tyr Tyr Cys Ala Arg Gln Arg Phe Tyr
                 85                  90                  95

Ala Met Asp Tyr Trp
                100
```

```
<210> SEQ ID NO 20
```

<211> LENGTH: 88
<212> TYPE: PRT
<213> ORGANISM: Mus musculus
<220> FEATURE:
<221> NAME/KEY: MISC_FEATURE
<223> OTHER INFORMATION: 1C11 Kappa LC.pro

<400> SEQUENCE: 20

Asp Ile Val Met Thr Gln Thr Pro Ser Ser Leu Ala Val Ser Val Gly
1               5                   10                  15

Glu Lys Val Thr Met Asn Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Lys Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp
                85

<210> SEQ ID NO 21
<211> LENGTH: 89
<212> TYPE: PRT
<213> ORGANISM: Mus musculus
<220> FEATURE:
<221> NAME/KEY: MISC_FEATURE
<223> OTHER INFORMATION: 3E1 Kappa LC.pro

<400> SEQUENCE: 21

Ile Met Ser Ala Ser Pro Gly Glu Lys Val Thr Ile Thr Cys Ser Ala
1               5                   10                  15

Arg Ser Ser Val Ser Tyr Met His Trp Phe Gln Gln Lys Pro Gly Thr
            20                  25                  30

Ser Pro Lys Leu Trp Ile Tyr Ser Thr Ser Asn Leu Ala Ser Gly Val
        35                  40                  45

Pro Ala Arg Phe Ser Gly Ser Gly Ser Gly Thr Ser Tyr Ser Leu Thr
    50                  55                  60

Ile Ser Arg Met Glu Ala Glu Asp Ala Ala Thr Tyr Tyr Cys Gln Gln
65                  70                  75                  80

Arg Ser Ser Tyr Pro Phe Thr Phe Gly
                85

<210> SEQ ID NO 22
<211> LENGTH: 91
<212> TYPE: PRT
<213> ORGANISM: Mus musculus
<220> FEATURE:
<221> NAME/KEY: MISC_FEATURE
<223> OTHER INFORMATION: 3G8 Kappa LC.pro

<400> SEQUENCE: 22

Ser Ser Leu Ser Ala Ser Leu Gly Glu Arg Val Ser Leu Thr Cys Arg
1               5                   10                  15

Ala Ser Gln Asp Ile Gly Ser Ser Leu Asn Trp Leu Gln Gln Glu Pro
            20                  25                  30

Asp Gly Thr Ile Lys Arg Leu Ile Tyr Ala Thr Ser Ser Leu Asp Ser
        35                  40                  45

Gly Val Pro Lys Arg Phe Ser Gly Ser Arg Ser Gly Ser Asp Tyr Ser
    50                  55                  60

```
Leu Thr Ile Ser Ser Leu Glu Ser Glu Asp Phe Val Asp Tyr Tyr Cys
 65                  70                  75                  80

Leu Gln Tyr Ala Ser Ser Pro Tyr Thr Phe Gly
                 85                  90

<210> SEQ ID NO 23
<211> LENGTH: 96
<212> TYPE: PRT
<213> ORGANISM: Mus musculus
<220> FEATURE:
<221> NAME/KEY: MISC_FEATURE
<223> OTHER INFORMATION: 3H10 Kappa LC.pro

<400> SEQUENCE: 23

His Gln Ser Pro Ser Ser Leu Ser Ala Ser Leu Gly Glu Arg Val Ser
  1               5                  10                  15

Leu Thr Cys Arg Ala Ser Gln Asp Ile Gly Ser Ser Leu Asn Trp Leu
             20                  25                  30

Gln Gln Glu Pro Asp Gly Thr Ile Lys Arg Leu Ile Tyr Ala Thr Ser
         35                  40                  45

Ser Leu Asp Ser Gly Val Pro Lys Arg Phe Gly Ser Arg Ser Gly
 50                  55                  60

Ser Asp Tyr Ser Leu Thr Ile Ser Ser Leu Glu Ser Glu Asp Phe Val
 65                  70                  75                  80

Asp Tyr Tyr Cys Leu Gln Tyr Ala Ser Ser Pro Trp Thr Phe Gly Gly
                 85                  90                  95

<210> SEQ ID NO 24
<211> LENGTH: 101
<212> TYPE: PRT
<213> ORGANISM: Mus musculus
<220> FEATURE:
<221> NAME/KEY: MISC_FEATURE
<223> OTHER INFORMATION: 4B3 Kappa LC.pro

<400> SEQUENCE: 24

Ser Pro Leu Ser Leu Pro Val Ser Leu Gly Asp Gln Ala Ser Ile Ser
  1               5                  10                  15

Cys Arg Ser Ser Gln Ser Leu Val His Ser Asn Gly Asn Thr His Leu
             20                  25                  30

His Trp Tyr Leu Gln Lys Pro Gly Gln Ser Pro Lys Leu Leu Ile Tyr
             35                  40                  45

Lys Val Ser Asn Arg Phe Ser Gly Val Pro Asp Arg Phe Ser Gly Ser
 50                  55                  60

Gly Ser Gly Thr Glu Phe Thr Leu Lys Ile Ser Arg Val Glu Ala Glu
 65                  70                  75                  80

Asp Leu Gly Val Tyr Phe Cys Ser Gln Ser Thr His Val Pro Leu Thr
                 85                  90                  95

Phe Gly Ala Gly Thr
            100

<210> SEQ ID NO 25
<211> LENGTH: 17
<212> TYPE: PRT
<213> ORGANISM: Mus musculus
<220> FEATURE:
<221> NAME/KEY: MISC_FEATURE
<223> OTHER INFORMATION: 1C11 Kappa LC.pro CDR1

<400> SEQUENCE: 25

Lys Ser Ser Gln Ser Leu Leu Tyr Ser Gly Asn Gln Lys Asn Tyr Leu
```

```
1               5                   10                  15

Ala

<210> SEQ ID NO 26
<211> LENGTH: 7
<212> TYPE: PRT
<213> ORGANISM: Mus musculus
<220> FEATURE:
<221> NAME/KEY: MISC_FEATURE
<223> OTHER INFORMATION: 1C11 Kappa LC.pro CDR2

<400> SEQUENCE: 26

Ile Tyr Trp Ala Ser Thr Arg
1               5

<210> SEQ ID NO 27
<211> LENGTH: 10
<212> TYPE: PRT
<213> ORGANISM: Mus musculus
<220> FEATURE:
<221> NAME/KEY: MISC_FEATURE
<223> OTHER INFORMATION: 3E1 Kappa LC.pro CDR1

<400> SEQUENCE: 27

Ser Ala Arg Ser Ser Val Ser Tyr Met His
1               5                   10

<210> SEQ ID NO 28
<211> LENGTH: 7
<212> TYPE: PRT
<213> ORGANISM: Mus musculus
<220> FEATURE:
<221> NAME/KEY: MISC_FEATURE
<223> OTHER INFORMATION: 3E1 Kappa LC.pro CDR2

<400> SEQUENCE: 28

Ile Tyr Ser Thr Ser Asn Leu
1               5

<210> SEQ ID NO 29
<211> LENGTH: 9
<212> TYPE: PRT
<213> ORGANISM: Mus musculus
<220> FEATURE:
<221> NAME/KEY: MISC_FEATURE
<223> OTHER INFORMATION: 3E1 Kappa LC.pro CDR3

<400> SEQUENCE: 29

Gln Gln Arg Ser Ser Tyr Pro Phe Thr
1               5

<210> SEQ ID NO 30
<211> LENGTH: 11
<212> TYPE: PRT
<213> ORGANISM: Mus musculus
<220> FEATURE:
<221> NAME/KEY: MISC_FEATURE
<223> OTHER INFORMATION: 3G8 Kappa LC.pro CDR1

<400> SEQUENCE: 30

Arg Ala Ser Gln Asp Ile Gly Ser Ser Leu Asn
1               5                   10

<210> SEQ ID NO 31
<211> LENGTH: 7
<212> TYPE: PRT
<213> ORGANISM: Mus musculus
```

<220> FEATURE:
<221> NAME/KEY: MISC_FEATURE
<223> OTHER INFORMATION: 3G8 Kappa LC.pro CDR2

<400> SEQUENCE: 31

Ile Tyr Ala Thr Ser Ser Leu
1               5

<210> SEQ ID NO 32
<211> LENGTH: 9
<212> TYPE: PRT
<213> ORGANISM: Mus musculus
<220> FEATURE:
<221> NAME/KEY: MISC_FEATURE
<223> OTHER INFORMATION: 3G8 Kappa LC.pro CDR3

<400> SEQUENCE: 32

Leu Gln Tyr Ala Ser Ser Pro Tyr Thr
1               5

<210> SEQ ID NO 33
<211> LENGTH: 11
<212> TYPE: PRT
<213> ORGANISM: Mus musculus
<220> FEATURE:
<221> NAME/KEY: MISC_FEATURE
<223> OTHER INFORMATION: 3H10 Kappa LC.pro CDR1

<400> SEQUENCE: 33

Arg Ala Ser Gln Asp Ile Gly Ser Ser Leu Asn
1               5                   10

<210> SEQ ID NO 34
<211> LENGTH: 7
<212> TYPE: PRT
<213> ORGANISM: Mus musculus
<220> FEATURE:
<221> NAME/KEY: MISC_FEATURE
<223> OTHER INFORMATION: 3H10 Kappa LC.pro CDR2

<400> SEQUENCE: 34

Ile Tyr Ala Thr Ser Ser Leu
1               5

<210> SEQ ID NO 35
<211> LENGTH: 9
<212> TYPE: PRT
<213> ORGANISM: Mus musculus
<220> FEATURE:
<221> NAME/KEY: MISC_FEATURE
<223> OTHER INFORMATION: 3H10 Kappa LC.pro CDR3

<400> SEQUENCE: 35

Leu Gln Tyr Ala Ser Ser Pro Trp Thr
1               5

<210> SEQ ID NO 36
<211> LENGTH: 16
<212> TYPE: PRT
<213> ORGANISM: Mus musculus
<220> FEATURE:
<221> NAME/KEY: MISC_FEATURE
<223> OTHER INFORMATION: 4B3 Kappa LC.pro CDR1

<400> SEQUENCE: 36

Arg Ser Ser Gln Ser Leu Val His Ser Asn Gly Asn Thr His Leu His
1               5                   10                  15

```
<210> SEQ ID NO 37
<211> LENGTH: 7
<212> TYPE: PRT
<213> ORGANISM: Mus musculus
<220> FEATURE:
<221> NAME/KEY: MISC_FEATURE
<223> OTHER INFORMATION: 4B3 Kappa LC.pro CDR2

<400> SEQUENCE: 37

Ile Tyr Lys Val Ser Asn Arg
1               5

<210> SEQ ID NO 38
<211> LENGTH: 9
<212> TYPE: PRT
<213> ORGANISM: Mus musculus
<220> FEATURE:
<221> NAME/KEY: MISC_FEATURE
<223> OTHER INFORMATION: 4B3 Kappa LC.pro CDR3

<400> SEQUENCE: 38

Ser Gln Ser Thr His Val Pro Leu Thr
1               5

<210> SEQ ID NO 39
<211> LENGTH: 10
<212> TYPE: PRT
<213> ORGANISM: Mus musculus
<220> FEATURE:
<221> NAME/KEY: MISC_FEATURE
<223> OTHER INFORMATION: 1C11 IgG1 HC pro CDR1

<400> SEQUENCE: 39

Gly Phe Asn Ile Lys Asp Thr Tyr Ile His
1               5                   10

<210> SEQ ID NO 40
<211> LENGTH: 18
<212> TYPE: PRT
<213> ORGANISM: Mus musculus
<220> FEATURE:
<221> NAME/KEY: MISC_FEATURE
<223> OTHER INFORMATION: 1C11 IgG1 HC pro CDR2

<400> SEQUENCE: 40

Arg Ile Asp Pro Ala Asn Gly Asn Thr Lys Tyr Asp Pro Lys Phe Gln
1               5                   10                  15

Asp Arg

<210> SEQ ID NO 41
<211> LENGTH: 8
<212> TYPE: PRT
<213> ORGANISM: Mus musculus
<220> FEATURE:
<221> NAME/KEY: MISC_FEATURE
<223> OTHER INFORMATION: 1C11 IgG1 HC pro CDR3

<400> SEQUENCE: 41

Ser Thr Gly Trp Tyr Phe Asp Val
1               5

<210> SEQ ID NO 42
<211> LENGTH: 10
<212> TYPE: PRT
<213> ORGANISM: Mus musculus
<220> FEATURE:
<221> NAME/KEY: MISC_FEATURE
```

```
<223> OTHER INFORMATION: 3E1 IgG1 HC pro CDR1

<400> SEQUENCE: 42

Gly Tyr Thr Phe Thr Glu Tyr Thr Met His
1               5                   10

<210> SEQ ID NO 43
<211> LENGTH: 18
<212> TYPE: PRT
<213> ORGANISM: Mus musculus
<220> FEATURE:
<221> NAME/KEY: MISC_FEATURE
<223> OTHER INFORMATION: 3E1 IgG1 HC pro CDR2

<400> SEQUENCE: 43

Gly Ile Ile Pro Asn Asn Gly Gly Thr Ser Tyr Asn Gln Lys Phe Lys
1               5                   10                  15

Gly Lys

<210> SEQ ID NO 44
<211> LENGTH: 3
<212> TYPE: PRT
<213> ORGANISM: Mus musculus
<220> FEATURE:
<221> NAME/KEY: MISC_FEATURE
<223> OTHER INFORMATION: 3E1 IgG1 HC pro CDR3

<400> SEQUENCE: 44

Trp Thr Thr
1

<210> SEQ ID NO 45
<211> LENGTH: 10
<212> TYPE: PRT
<213> ORGANISM: Mus musculus
<220> FEATURE:
<221> NAME/KEY: MISC_FEATURE
<223> OTHER INFORMATION: 3G8 IgG2b HC pro CDR1

<400> SEQUENCE: 45

Gly Tyr Thr Phe Thr Ser Tyr Val Met His
1               5                   10

<210> SEQ ID NO 46
<211> LENGTH: 18
<212> TYPE: PRT
<213> ORGANISM: Mus musculus
<220> FEATURE:
<221> NAME/KEY: MISC_FEATURE
<223> OTHER INFORMATION: 3G8 IgG2b HC pro CDR2

<400> SEQUENCE: 46

Tyr Ile Asn Pro Tyr Asn Asp Gly Thr Lys Tyr Asn Glu Lys Phe Lys
1               5                   10                  15

Gly Lys

<210> SEQ ID NO 47
<211> LENGTH: 9
<212> TYPE: PRT
<213> ORGANISM: Mus musculus
<220> FEATURE:
<221> NAME/KEY: MISC_FEATURE
<223> OTHER INFORMATION: 3G8 IgG2b HC pro CDR3

<400> SEQUENCE: 47

Ser Ala Tyr Tyr Arg Tyr Phe Asp Val
```

```
<210> SEQ ID NO 48
<211> LENGTH: 10
<212> TYPE: PRT
<213> ORGANISM: Mus musculus
<220> FEATURE:
<221> NAME/KEY: MISC_FEATURE
<223> OTHER INFORMATION: 3H10 IgG1 HC pro CDR1

<400> SEQUENCE: 48

Gly Tyr Ser Phe Thr Gly Tyr Thr Met Asn
1               5                   10

<210> SEQ ID NO 49
<211> LENGTH: 18
<212> TYPE: PRT
<213> ORGANISM: Mus musculus
<220> FEATURE:
<221> NAME/KEY: MISC_FEATURE
<223> OTHER INFORMATION: 3H10 IgG1 HC pro CDR2

<400> SEQUENCE: 49

Leu Ile Ile Pro Tyr Asn Gly Gly Thr Ser Tyr Asn Gln Lys Phe Lys
1               5                   10                  15

Gly Lys

<210> SEQ ID NO 50
<211> LENGTH: 9
<212> TYPE: PRT
<213> ORGANISM: Mus musculus
<220> FEATURE:
<221> NAME/KEY: MISC_FEATURE
<223> OTHER INFORMATION: 3H10 IgG1 HC pro CDR3

<400> SEQUENCE: 50

Gly Gly Leu Arg Arg Ala Met Asp Tyr
1               5

<210> SEQ ID NO 51
<211> LENGTH: 10
<212> TYPE: PRT
<213> ORGANISM: Mus musculus
<220> FEATURE:
<221> NAME/KEY: MISC_FEATURE
<223> OTHER INFORMATION: 4B3 IgG1 HC pro CDR1

<400> SEQUENCE: 51

Gly Phe Ser Leu Thr Ser Tyr Gly Val His
1               5                   10

<210> SEQ ID NO 52
<211> LENGTH: 17
<212> TYPE: PRT
<213> ORGANISM: Mus musculus
<220> FEATURE:
<221> NAME/KEY: MISC_FEATURE
<223> OTHER INFORMATION: 4B3 IgG1 HC pro CDR2

<400> SEQUENCE: 52

Val Ile Trp Thr Asp Gly Ser Thr Thr Tyr Asn Ser Ala Leu Lys Ser
1               5                   10                  15

Arg

<210> SEQ ID NO 53
<211> LENGTH: 8
```

```
<212> TYPE: PRT
<213> ORGANISM: Mus musculus
<220> FEATURE:
<221> NAME/KEY: MISC_FEATURE
<223> OTHER INFORMATION: 4B3 IgG1 HC pro CDR3

<400> SEQUENCE: 53

Gln Arg Phe Tyr Ala Met Asp Tyr
1               5

<210> SEQ ID NO 54
<211> LENGTH: 11
<212> TYPE: PRT
<213> ORGANISM: Mus musculus
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 54

Arg Ala Ser Gln Ser Xaa Gly Ser Ser Leu Xaa
1               5                   10

<210> SEQ ID NO 55
<211> LENGTH: 7
<212> TYPE: PRT
<213> ORGANISM: Mus musculus
<220> FEATURE:
<221> NAME/KEY: misc_feature
<222> LOCATION: (6)..(6)
<223> OTHER INFORMATION: Xaa can be any naturally occurring amino acid

<400> SEQUENCE: 55

Ile Tyr Ala Thr Ser Xaa Leu
1               5

<210> SEQ ID NO 56
<211> LENGTH: 9
<212> TYPE: PRT
<213> ORGANISM: Mus musculus
<220> FEATURE:
<221> NAME/KEY: misc_feature
<222> LOCATION: (8)..(8)
<223> OTHER INFORMATION: Xaa can be any naturally occurring amino acid

<400> SEQUENCE: 56

Leu Gln Tyr Ala Ser Ser Pro Xaa Thr
1               5

<210> SEQ ID NO 57
<211> LENGTH: 10
<212> TYPE: PRT
<213> ORGANISM: Mus musculus
<220> FEATURE:
<221> NAME/KEY: misc_feature
<222> LOCATION: (3)..(3)
<223> OTHER INFORMATION: Xaa can be any naturally occurring amino acid

<400> SEQUENCE: 57

Gly Tyr Xaa Phe Thr Ser Tyr Thr Met His
1               5                   10

<210> SEQ ID NO 58
<211> LENGTH: 18
<212> TYPE: PRT
```

```
<213> ORGANISM: Mus musculus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 58

Xaa Ile Ile Pro Tyr Asn Gly Gly Thr Xaa Tyr Asn Gln Lys Phe Lys
1               5                   10                  15

Gly Lys

<210> SEQ ID NO 59
<211> LENGTH: 8
<212> TYPE: PRT
<213> ORGANISM: Mus musculus
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 59

Ser Thr Xaa Arg Xaa Xaa Asp Xaa
1               5

<210> SEQ ID NO 60
<211> LENGTH: 104
<212> TYPE: PRT
<213> ORGANISM: Mus musculus
<220> FEATURE:
<221> NAME/KEY: MISC_FEATURE
<222> LOCATION: (21)..(21)
<223> OTHER INFORMATION: Xaa is Thr, Ala or Val
<220> FEATURE:
<221> NAME/KEY: MISC_FEATURE
<222> LOCATION: (25)..(25)
<223> OTHER INFORMATION: Xaa is Asn, Thr, or Ser
<220> FEATURE:
<221> NAME/KEY: MISC_FEATURE
<222> LOCATION: (47)..(47)
<223> OTHER INFORMATION: Xaa is Arg, Gly, Tyr, Leu or Val
<220> FEATURE:
<221> NAME/KEY: MISC_FEATURE
<222> LOCATION: (56)..(56)
<223> OTHER INFORMATION: Xaa is Lys, Ser or Thr
<220> FEATURE:
<221> NAME/KEY: MISC_FEATURE
<222> LOCATION: (98)..(98)
<223> OTHER INFORMATION: Xaa is Gly, Thr, Tyr, Leu or Phe
<220> FEATURE:
<221> NAME/KEY: MISC_FEATURE
<222> LOCATION: (100)..(100)
<223> OTHER INFORMATION: Xaa is Tyr or Ala
<220> FEATURE:
<221> NAME/KEY: MISC_FEATURE
<222> LOCATION: (101)..(101)
<223> OTHER INFORMATION: Xaa is Phe or Met
<220> FEATURE:
<221> NAME/KEY: MISC_FEATURE
<222> LOCATION: (103)..(103)
<223> OTHER INFORMATION: Xaa is Val or Tyr

<400> SEQUENCE: 60
```

Leu Glu Glu Ser Gly Pro Glu Leu Val Lys Pro Gly Ala Ser Val Lys
1               5                   10                  15

Ile Ser Cys Lys Xaa Ser Gly Tyr Xaa Phe Thr Ser Tyr Thr Met His
                20                  25                  30

Trp Val Lys Gln Ser Pro Gly Lys Gly Leu Glu Trp Ile Gly Xaa Ile
            35                  40                  45

Ile Pro Tyr Asn Gly Gly Thr Xaa Tyr Asn Gln Lys Phe Lys Gly Lys
        50                  55                  60

Ala Thr Leu Thr Val Asp Lys Ser Ser Ser Thr Ala Tyr Met Glu Leu
65                  70                  75                  80

Ser Ser Leu Thr Ser Glu Asp Ser Ala Val Tyr Tyr Cys Ala Arg Ser
                85                  90                  95

Thr Xaa Arg Xaa Xaa Asp Xaa Trp
            100

<210> SEQ ID NO 61
<211> LENGTH: 93
<212> TYPE: PRT
<213> ORGANISM: Mus musculus
<220> FEATURE:
<221> NAME/KEY: MISC_FEATURE
<222> LOCATION: (1)..(1)
<223> OTHER INFORMATION: Xaa is Thr or Ser
<220> FEATURE:
<221> NAME/KEY: MISC_FEATURE
<222> LOCATION: (12)..(12)
<223> OTHER INFORMATION: Xaa is Lys, Arg or Gln
<220> FEATURE:
<221> NAME/KEY: MISC_FEATURE
<222> LOCATION: (15)..(15)
<223> OTHER INFORMATION: Xaa is Met, Ile or Leu
<220> FEATURE:
<221> NAME/KEY: MISC_FEATURE
<222> LOCATION: (23)..(23)
<223> OTHER INFORMATION: Xaa is Leu, Val or Ile
<220> FEATURE:
<221> NAME/KEY: MISC_FEATURE
<222> LOCATION: (28)..(28)
<223> OTHER INFORMATION: Xaa is Ala, His or Asn
<220> FEATURE:
<221> NAME/KEY: MISC_FEATURE
<222> LOCATION: (30)..(30)
<223> OTHER INFORMATION: Xaa is Tyr, Phe or Leu
<220> FEATURE:
<221> NAME/KEY: MISC_FEATURE
<222> LOCATION: (36)..(36)
<223> OTHER INFORMATION: Xaa is Gln, Thr, Gly and Gln
<220> FEATURE:
<221> NAME/KEY: MISC_FEATURE
<222> LOCATION: (47)..(47)
<223> OTHER INFORMATION: Xaa is Thr, Asn or Ser
<220> FEATURE:
<221> NAME/KEY: MISC_FEATURE
<222> LOCATION: (54)..(54)
<223> OTHER INFORMATION: Xaa is Asp, Ala or Lys
<220> FEATURE:
<221> NAME/KEY: MISC_FEATURE
<222> LOCATION: (72)..(72)
<223> OTHER INFORMATION: Xaa is Val, Met or Leu
<220> FEATURE:
<221> NAME/KEY: MISC_FEATURE
<222> LOCATION: (90)..(90)
<223> OTHER INFORMATION: Xaa is Phe, Tyr, Trp or Leu

<400> SEQUENCE: 61

Xaa Pro Ser Ser Leu Ser Ala Ser Leu Gly Glu Xaa Val Ser Xaa Thr
1               5                   10                  15

Cys Arg Ala Ser Gln Ser Xaa Gly Ser Ser Leu Xaa Trp Xaa Gln Gln
            20                  25                  30

```
Lys Pro Gly Xaa Ser Pro Lys Leu Leu Ile Tyr Ala Thr Ser Xaa Leu
            35              40                  45

Asp Ser Gly Val Pro Xaa Arg Phe Ser Gly Ser Gly Ser Gly Thr Asp
        50              55                  60

Tyr Ser Leu Thr Ile Ser Ser Xaa Glu Ala Glu Asp Phe Val Asp Tyr
65                  70              75                      80

Tyr Cys Leu Gln Tyr Ala Ser Ser Pro Xaa Thr Phe Gly
                85              90
```

METHODS OF DIAGNOSING *CLOSTRIDIUM DIFFICILE* INFECTION

RELATED APPLICATIONS

This application claims the benefit of priority of U.S. Provisional Patent Application No. 61/447,225, filed Feb. 28, 2011, which is incorporated herein by reference in its entirety.

FIELD

The disclosure generally relates to methods of diagnosing *Clostridium difficile* infection and compounds used in the methods. More particularly, the disclosure related to methods of diagnosing *Clostridium difficile*-associated diarrhea (CDAD) in a subject with *Clostridium difficile* infection (CDI) and reagents and kits for carrying out the methods.

BACKGROUND

*Clostridium difficile*, often called *C. difficile* or *C. diff*, is a bacterium that can cause symptoms ranging from diarrhea to life-threatening inflammation of the colon. *Clostridium difficile* infection (CDI), also known as *Clostridium difficile*-associated diarrhea (CDAD), became a medically recognized infectious disease, initially as clindamycin colitis, over 3 decades ago. In the U.S. alone there are several hundred thousand cases per year, with a conservative estimated cost approaching $10,000 per case. CDAD/CDI is a significant health concern worldwide, resulting from the colonization and infection of the bowel by *Clostridium difficile*, a Gram-positive, spore-forming, obligate anaerobic bacterium. *Clostridium difficile* causes diarrhea and other intestinal disease when competing bacteria in the gut flora are wiped out by antibiotics. Even though much has been learned about CDAD/CDI, still many unsolved questions remain, particularly in the diagnostic field.

CDAD/CDI remains the most important infectious cause of diarrhea that develops from health care contact. While patient isolation and environmental disinfection appear to help in the control of CDAD/CDI, the effectiveness of infection control measures has been inconsistent. Outbreaks of particularly aggressive infection recently have appeared. One report involving a surgical unit found 5% of their patients with CDAD/CDI required surgical intervention, and overall there was an associated mortality rate of 3.5%. Since then, recognition of outbreaks from this hypervirulent *Clostridium difficile* strain (BI or NAP1), represented by a genotype overproducing toxins and harboring multiple resistance phenotypes, have been reported from Canada and the United States. Another alarming development has been the recognition that there are strains incapable of expressing an intact toxin A that can still cause disease and death. This observation complicates the current laboratory diagnosis since many of the common tests employed by clinical microbiology laboratories are immunoassays only detecting toxin A.

CDAD/CDI has also been recognized as the most commonly diagnosed reason for bacterial diarrhea in persons infected with HIV, further expanding the clinical impact of this infectious disease. CDAD/CDI appears to be growing in prevalence for many populations. With recent reports of hypervirulent disease from Canada and the United States, the diagnosis of this infection is critical as we are now faced with potentially more life-threatening as well as more antibiotic-resistant CDAD/CDI infections.

CDAD/CDI is a globally important, yet poorly diagnosed, healthcare-associated infectious disease. Importantly, the causative agent of this disease has become a crucial emerging pathogen with new virulent strains seen in the hospital, apparent emergence of community acquired disease, and recognition of CDAD/CDI as a key pathogen for HIV-infected persons. Understanding all these important biologic observations will be dependent on accurate diagnostic testing that is now largely lacking.

The diagnosis of CDAD/CDI in today's environment is based on clinical and laboratory findings because of current suboptimal laboratory diagnostic capabilities. A case definition for the usual presentation of CDAD/CDI includes: (i) diarrhea, typically defined as at least six watery stools over 36 hours, (or eight stools during 48 hours), (ii) a history of antimicrobial agent therapy within eight weeks of the onset of diarrhea, (iii) pseudomembranes seen at lower gastrointestinal endoscopy (this is required for the diagnosis of colitis), or a stool sample positive for the presence a toxin B (or toxins A and B), or a toxigenic isolate of *Clostridium difficile* (toxin B or toxins A and B) recovered from the stool, and (iv) no other reason for diarrhea.

Since 10 to 30% of hospitalized patients can be colonized with *Clostridium difficile*, and 20% of hospitalized patients experience some diarrhea, evaluating stools from patients without all the clear risk factors for CDAD/CDI using current technology testing only for the presence of *Clostridium difficile* or its toxins, with no objective measure of host response, leads to false positive clinical diagnostics. Thus, suboptimal detection of true disease combined with substantial reporting of false positive results indicates an urgent need for a better, fully objective diagnostic test. Current laboratory testing is limited to detection of the *Clostridium difficile* organism and/or its toxin product(s) and does not differentiate infected from simply colonized patients, thus leading to inaccurate diagnosis as well as antibiotic mis/overuse.

Accordingly, there is a need in the art for more specific and sensitive diagnostic methods for CDAD/CDI that will improve patient care by enabling specific, correct treatment at a very early time point, thus lowering the potential risk of severe disease and death as well as lower the overuse of antimicrobial agents. The following disclosure describes the specifics of such methods.

SUMMARY

The disclosure satisfies at least one of the aforementioned needs in the art by providing improved methods of diagnosing CDAD/CDI.

The disclosure provides methods of diagnosing CDAD/CDI in a stool specimen or fluid exposed to a stool specimen of a subject, the method comprising detecting in the stool specimen or fluid exposed to the stool specimen an increase in a non-muscle tropomyosin, or a fragment thereof. In exemplary embodiments, the methods of the disclosure further comprise detecting a *Clostridium difficile* toxin A polypeptide or polynucleotide, or a fragment thereof. In further exemplary embodiments, the methods further comprise detecting a C-terminal 250-amino-acid fragment of *Clostridium difficile* toxin B polypeptide, or a fragment thereof, or a 3'-terminal 750-nucleotide fragment of a *Clostridium difficile* toxin B nucleic acid molecule, or a fragment thereof.

The disclosure also provides methods of diagnosing CDAD/CDI in a stool specimen or fluid exposed to a stool specimen of a subject, the method comprising detecting in the stool specimen or fluid exposed to the stool specimen a *Clostridium difficile* toxin B, or a fragment thereof; and an increase in a colonic epithelial cell protein, or a fragment thereof, selected from the group consisting of non-muscle tropomyosin 1 (TM1), non-muscle tropomyosin 2 (TM2), non-muscle tropomyosin 4 (TM4), and non-muscle tropomyosin 5 (TM5).

In exemplary embodiments, the methods of the disclosure comprise detecting a tropomyosin isoform encoded by a tropomyosin gene selected from the group consisting of tropomyosin 1 (TPM1), tropomyosin 2 (TPM2), tropomyosin 3 (TPM3), and tropomyosin 4 (TPM4). In aspects, the tropomyosin isoform is tropomyosin 5 (TM5).

In exemplary embodiments, the methods of the disclosure comprise detecting a non-muscle tropomyosin by an anti-tropomyosin antibody. In exemplary aspects, the anti-tropomyosin antibody specifically binds a tropomyosin isoform encoded by a tropomyosin gene selected from the group consisting of tropomyosin 1 (TPM1), tropomyosin 2 (TPM2), tropomyosin 3 (TPM3), and tropomyosin 4 (TPM4). In exemplary aspects, the anti-tropomyosin antibody specifically binds tropomyosin 5 (TM5). In exemplary aspects, the anti-tropomyosin antibody is a monoclonal antibody, a polyclonal antibody, a human antibody, a humanized antibody, or a chemically modified derivative of an antibody.

In exemplary embodiments, the methods of the disclosure comprise detecting *Clostridium difficile* toxin B by immunoassay, cytotoxicity assay, toxigenic culture, reverse-transcriptase polymerase chain reaction (PCR), PCR, or real-time PCR.

In exemplary embodiments, the methods of the disclosure comprise detecting a *Clostridium difficile* toxin B or a fragment thereof by an antibody or antibody fragment that binds *Clostridium difficile* toxin B. In exemplary aspects, the antibody or antibody fragment binds a C-terminal 250-amino-acid fragment of *Clostridium difficile* toxin B polypeptide, or a fragment thereof, of *Clostridium difficile* toxin B (CDB-250). In exemplary aspects, the CDB-250 antibody or antibody fragment does not detectably bind to *Clostridium difficile* toxin A. In exemplary aspects, the antibody or antibody fragment is monoclonal. In exemplary aspects, the antibody or antibody fragment specifically binds to a polypeptide comprising the sequence selected from the group consisting of SEQ ID NOS: 3-13. In exemplary aspects, the antibody or antibody fragment is produced by a hybridoma selected from the group consisting of the 3H10 hybridoma, the 1C11 hybridoma, the 2C10 hybridoma, the 3E1 hybridoma, the 3G8 hybridoma and the 4B3 hybridoma. In particular aspects, the antibody or antibody fragment binds the C-terminal 250-amino-acid region of *Clostridium difficile* toxin B polypeptide with an affinity of at least $10^8$ $M^{-1}$.

In exemplary embodiments, the methods of the disclosure include the use of an antibody or antibody fragment which comprises a heavy chain CDR1 amino acid sequence selected from the group consisting of SEQ ID NOS: 39, 42, 45, 48, 51 and a variant thereof in which at most two amino acids have been changed, or a consensus sequence thereof; a heavy chain CDR2 amino acid sequence selected from the group consisting of SEQ ID NOS: 40, 43, 46, 49, 52 and a variant thereof in which at most two amino acids have been changed or a consensus sequence thereof; and a heavy chain CDR3 amino acid sequence selected from the group consisting of SEQ ID NOS: 41, 44, 47, 50, 53 and a variant thereof in which at most two amino acids have been changed, or a consensus sequence thereof. In exemplary aspects, one or more of the heavy chain CDR1, CDR2 or CDR3 amino acid sequences is a consensus sequence set forth in FIG. 4. In exemplary aspects, an amino acid in a heavy chain CDR1 amino acid sequence is replaced with an amino acid from a corresponding position within a different heavy chain CDR1 amino acid sequence set forth in FIG. 4; an amino acid in a heavy chain CDR2 amino acid sequence is replaced with an amino acid from a corresponding position within a different heavy chain CDR2 amino acid sequence set forth in FIG. 4; or an amino acid in a heavy chain CDR3 amino acid sequence is replaced with an amino acid from a corresponding position within a different heavy chain CDR3 amino acid sequence set forth in FIG. 4. In exemplary aspects, the antibody or antibody fragment comprises an amino acid sequence at least 95% identical to a heavy chain variable region amino acid sequence set forth in FIG. 4. In exemplary aspects, the antibody or antibody fragment comprises a heavy chain variable region amino acid sequence set forth in FIG. 4. In exemplary aspects, the antibody or antibody fragment in which one or more heavy chain framework amino acid(s) have been replaced with a corresponding amino acid(s) from another human antibody heavy chain framework amino acid sequence.

In exemplary embodiments, the methods of the disclosure include the use of an antibody or antibody fragment which comprises a light chain CDR1 amino acid sequence selected from the group consisting of SEQ ID NOS: 25, 27, 30, 33, 36 and a variant thereof in which at most two amino acids have been changed; a light chain CDR2 amino acid sequence selected from the group consisting of SEQ ID NOS: 26, 28, 31, 34, 37 and a variant thereof in which at most two amino acids have been changed; and a light chain CDR3 amino acid sequence selected from the group consisting of SEQ ID NOS: 29, 32, 35, 38 and a variant thereof in which at most two amino acids have been changed. In exemplary aspects, one or more of the light chain CDR1, CDR2 or CDR3 amino acid sequences is a consensus sequence set forth in FIG. 4. In exemplary aspects an amino acid in a light chain CDR1 amino acid sequence is replaced with an amino acid from a corresponding position within a different light chain CDR1 amino acid sequence set forth in FIG. 4; an amino acid in a light chain CDR2 amino acid sequence is replaced with an amino acid from a corresponding position within a different light chain CDR2 amino acid sequence set forth in FIG. 4; or an amino acid in a light chain CDR3 amino acid sequence is replaced with an amino acid from a corresponding position within a different light chain CDR3 amino acid sequence set forth in FIG. 4. In exemplary aspects, the antibody or antibody fragment comprises an amino acid sequence at least 95% identical to a light chain variable region amino acid sequence set forth in FIG. 4. In some aspects, the antibody or antibody fragment comprises a light chain variable region amino acid sequence set forth in FIG. 4. In exemplary aspects, one or more light chain framework amino acids have been replaced in the antibody or antibody fragment with corresponding amino acid(s) from another human antibody light chain framework amino acid sequence. In exemplary aspects, the methods of the disclosure are carried out on a human subject.

The disclosure includes kits for diagnosing CDI or CDAD comprising reagents for detecting in a stool specimen or fluid exposed to the stool specimen an increase in a non-muscle tropomyosin, or a fragment thereof; and optionally, instructions for using the reagents to make a diagnosis of CDAD. In exemplary aspects, the kits also comprise reagents for detecting a *Clostridium difficile* toxin A polypeptide or polynucleotide, or a fragment thereof. In exemplary aspects, the kits can also comprise reagents for detecting a C-terminal 250-amino-acid fragment of *Clostridium difficile* toxin B polypeptide, or a fragment thereof, or a 3'-terminal 750-nucleotide fragment of a *Clostridium difficile* toxin B nucleic acid molecule, or a fragment thereof.

The disclosure likewise includes kits for diagnosing CDI or CDAD comprising reagents for detecting in a stool specimen or fluid exposed to the stool specimen a *Clostridium difficile* toxin B, or a fragment thereof, and a colonic epithelial cell protein, or a fragment thereof, wherein the colonic epithelial protein is selected from the group consisting of non-muscle tropomyosin 1, non-muscle tropomyosin 2, non-muscle tropomyosin 4, and non-muscle tropomyosin 5.

In exemplary aspects, the kits of the disclosure comprise reagents for detecting a non-muscle tropomyosin. In exemplary aspects, the reagent for detecting a non-muscle tropomyosin is an anti-tropomyosin antibody. In exemplary aspects, the anti-tropomyosin antibody is an antibody that that specifically binds a tropomyosin isoform encoded by a tropomyosin gene selected from the group consisting of tropomyosin 1 (TPM1), tropomyosin 2 (TPM2), tropomyosin 3 (TPM3), and tropomyosin 4 (TPM4). In exemplary aspects, the anti-tropomyosin antibody specifically binds non-muscle tropomyosin isoform 5 (TM5). In exemplary aspects, the anti-tropomyosin antibody is a monoclonal antibody, a polyclonal antibody, a human antibody, a humanized antibody, or a chemically modified derivative of an antibody.

In exemplary aspects, the kits of the disclosure also comprise reagents for detecting *Clostridium difficile* toxin B or a fragment thereof. In exemplary aspects, the reagent is an antibody or antibody fragment that binds *Clostridium difficile* toxin B. In exemplary aspects, the antibody or antibody fragment binds a C-terminal 250-amino-acid fragment of *Clostridium difficile* toxin B polypeptide (CDB-250), or a fragment thereof. In exemplary aspects, the antibody or antibody fragment does not detectably bind to *Clostridium difficile* toxin A. In exemplary aspects, the CDB-250 antibody is a monoclonal antibody or a fragment thereof. In exemplary aspects, the CDB-250 antibody or antibody fragment specifically binds to a polypeptide comprising the sequence selected from the group consisting of SEQ ID NOS: 3-13. In exemplary aspects, the antibody or antibody fragment is produced by a hybridoma selected from the group consisting of the 3H10 hybridoma, the 1C11 hybridoma, the 2C10 hybridoma, the 3E1 hybridoma, the 3G8 hybridoma and the 4B3 hybridoma.

In an exemplary embodiment, a kit of the disclosure comprises an antibody or antibody fragment, wherein the antibody or antibody fragment comprises a heavy chain CDR1 amino acid sequence selected from the group consisting of SEQ ID NOS: 39, 42, 45, 48, 51 and a variant thereof in which at most two amino acids have been changed, or a consensus sequence thereof; a heavy chain CDR2 amino acid sequence selected from the group consisting of SEQ ID NOS: 40, 43, 46, 49, 52 and a variant thereof in which at most two amino acids have been changed or a consensus sequence thereof; and a heavy chain CDR3 amino acid sequence selected from the group consisting of SEQ ID NOS: 41, 44, 47, 50, 53 and a variant thereof in which at most two amino acids have been changed, or a consensus sequence thereof.

In an exemplary embodiment, a kit of the disclosure comprises an antibody or antibody fragment, wherein the antibody or antibody fragment comprises a light chain CDR1 amino acid sequence selected from the group consisting of SEQ ID NOS: 25, 27, 30, 33, 36 and a variant thereof in which at most two amino acids have been changed; a light chain CDR2 amino acid sequence selected from the group consisting of SEQ ID NOS: 26, 28, 31, 34, 37 and a variant thereof in which at most two amino acids have been changed; and a light chain CDR3 amino acid sequence selected from the group consisting of SEQ ID NOS: 29, 32, 35, 38 and a variant thereof in which at most two amino acids have been changed.

The disclosure also provides kits wherein the reagent for detecting a 3'-terminal 750-nucleotide fragment of *Clostridium difficile* toxin B (CDB-250) nucleic acid molecule, or a fragment thereof, is one or more nucleotides or nucleotide primers that specifically binds CDB-750, or a fragment thereof. Such kits may further comprise an antibody or a fragment thereof that specifically binds a colonic epithelial protein selecting from the group consisting of tropomyosin 1 (TM1), tropomyosin 2 (TM2), tropomyosin 3 (TM3), tropomyosin 4 (TM4), and tropomyosin 5 (TM5).

In exemplary embodiments, the methods of the disclosure detect CDAD/CDI in a stool specimen or fluid exposed to a stool specimen, wherein the specimen or fluid is diluted in a buffer of neutral pH and boiled for a period of time which ranges from about 30 seconds to about 30 minutes. In exemplary aspects, the specimen or fluid is optionally cooled on ice, and further subjected to centrifugation at about 12,000 g for about 30 minutes for collection of a supernatant. In exemplary aspects, the specimen or fluid is further subjected to isoelectric point precipitation to enrich tropomyosin, wherein the isoelectric point precipitation is carried out by adjusting sample pH to a pH from about pH 4.5 to about pH 4.7 with hydrochloric acid followed by centrifugation at about 12,000×g for about 30 minutes to collect tropomyosin in a pellet.

The foregoing summary is not intended to define every aspect of the subject matter of the disclosure, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the subject matter of the disclosure will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

BRIEF DESCRIPTION OF THE DRAWING

The following drawing forms part of the present specification and is included to further illustrate aspects of the disclosure. The disclosure may be better understood by reference to the figures of the drawing in combination with the detailed description of the specific embodiments presented herein.

FIG. 1 provides an alignment of the amino acid sequences of *Clostridium difficile* toxin A and of *Clostridium difficile* toxin B.

FIG. 2 provides the amino acid sequence (single-letter code) of a region containing sequence repeat motifs in the C-terminal region of 250 amino acids of *Clostridium difficile* toxin B (C-250) identified in this disclosure as having effective immunogenicity.

DETAILED DESCRIPTION

Figure 3:
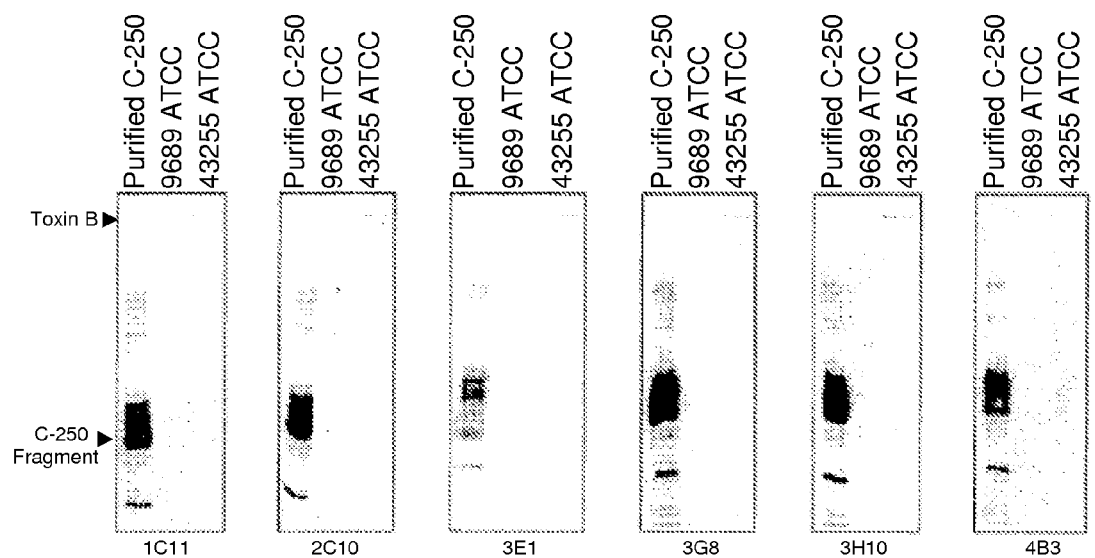
FIG. 3 presents a panel of Western blots. Each blot contained purified CDB-C250, a crude lysate of a *Clostridium difficile* (ATCC 9689) that produced reduced amounts of toxin and a crude lysate of a pathogenic strain of *Clostridium difficile* (ATCC 43255) that is a strong toxin producer. Anti-CDB-C250 mAb probes were present in culture supernatants of hybridomas 1C11, 2C10, 3E1, 3G8, 3H10, and 4B3.
Figure 4B:
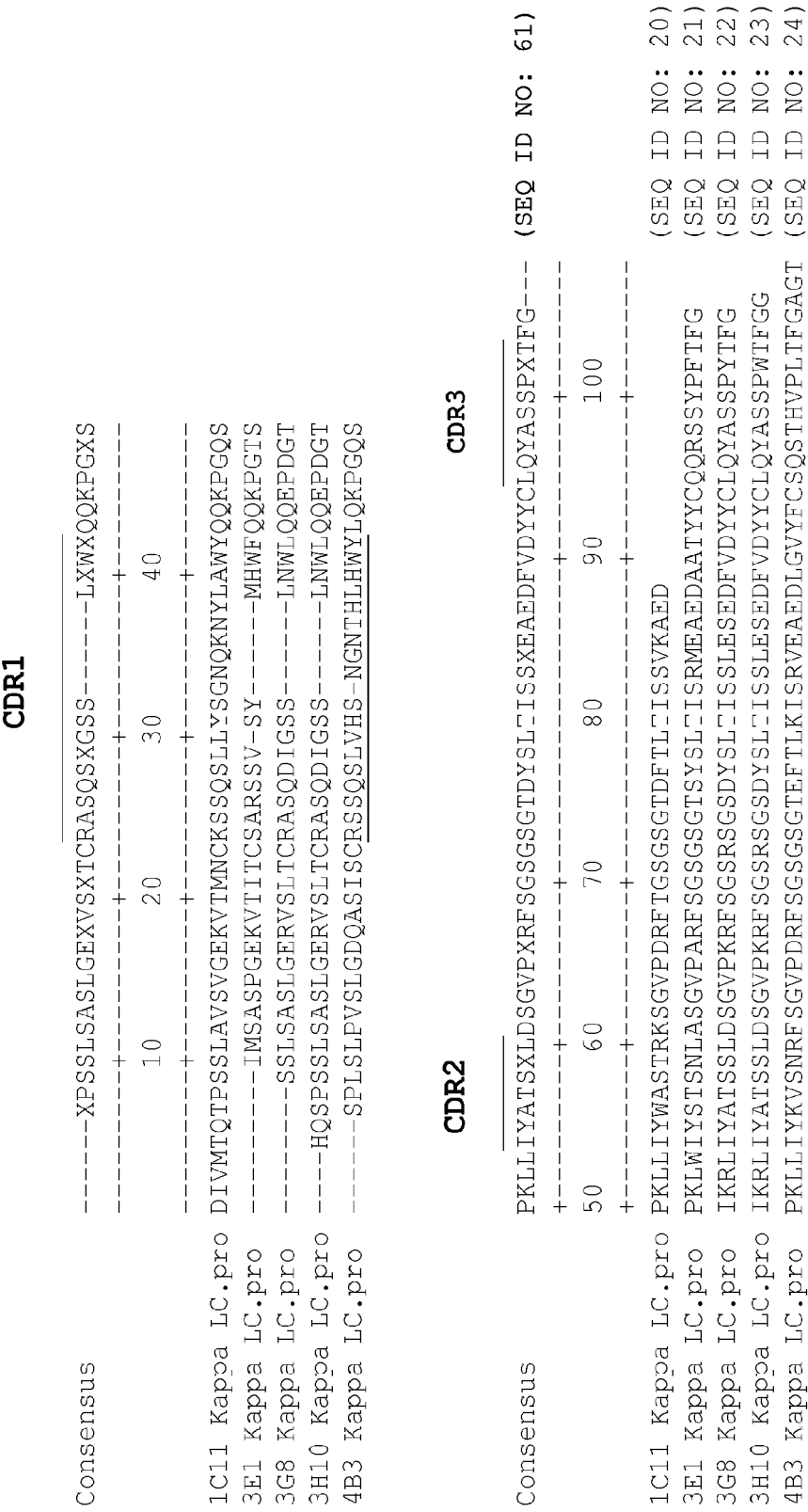
FIG. 4 provides the amino acid sequences of the variable regions of the heavy chain (upper panel) and light chain (lower panel) of anti-CDB-C250 monoclonal antibodies identified in Example 5. The complementarity determining regions are highlighted by identification as CDR1, CDR2 and CDR3 for each of the heavy and light chain variable regions. A horizontal bar over a region of the consensus sequence demarcates the consensus sequence of each CDR and a horizontal bar under regions of the monoclonal antibody sequences demarcates CDR regions in those antibodies.

The disclosure provides methods of diagnosing *Clostridium difficile* infection (CDI), also known as *Clostridium difficile*-associated diarrhea (CDAD). More specifically, the disclosure is directed to methods of diagnosing CDAD/CDI by detecting host response targets alone. The disclosure also includes methods of diagnosing CDAD/CDI by detecting both microbial and host response targets for CDAD/CDI. In exemplary aspects, the methods target positive detection of a host response (release of colonic epithelial cell protein) and a microbial target (*Clostridium difficile* toxin A or B). In exemplary aspects, the methods target the expression of non-muscle tropomyosin as a colonic epithelial cell protein and toxin B as the CDAD/CDI toxin. In addition, the methods provide improved protocols for stool specimen preparation.

Before any embodiments of the subject matter of the disclosure are explained in detail, however, it is to be understood that the disclosure is not limited in its application to the details of construction and the arrangement of components set forth in the following description or illustrated in the figures and examples. The section headings used herein are for organizational purposes only and are not to be construed as limiting the subject matter described. All references cited in this application are expressly incorporated by reference herein.

The disclosure embraces other embodiments and is practiced or carried out in various ways. Also, it is to be understood that the phraseology and terminology used herein is for the purpose of description and should not be regarded as limiting. The terms "including," "comprising," or "having" and variations thereof are meant to encompass the items listed thereafter and equivalents thereof as well as additional subject matter.

Definitions

To aid in the detailed description of the methods and kits according to the disclosure, a few express definitions are provided. As used herein, the following terms have the meanings ascribed to them unless specified otherwise.

It is noted here that, as used in this specification and the appended claims, the singular forms "a," "an," and "the" include plural reference unless the context clearly dictates otherwise.

Ranges, in various aspects, are expressed herein as from "about" or "approximately" one particular value and/or to "about" or "approximately" another particular value. When ranges are expressed in these terms, it is understood that some amount of variation is included in the range. Likewise, when values are expressed as approximations, by use of the antecedent "about" or "approximately," it is understood that some amount of variation is included in the value.

The terms "polypeptide," "peptide" and "protein" are used interchangeably herein to refer to a polymer of amino acid residues linked via peptide bonds. The term "protein" typically refers to large polypeptides. The term "peptide" typically refers to short polypeptides.

The term "gene" refers to a DNA sequence that encodes a sequence of amino acids which comprise all or part of one or more polypeptides.

"CDI" means "*Clostridium difficile* infection" or "*C. diff* infection" including, but not limited to, *Clostridium difficile*-associated diarrhea (CDAD). CDI typically involves a disease of the gastrointestinal tract of a mammal, such as a human. CDAD is the medical condition associated with diarrhea and other threatening intestinal conditions resulting from CDI. Thus, CDAD and CDI are used interchangeably herein and, in some aspects, referred to as CDAD/CDI herein.

The term "toxin A" refers to the toxin A protein (enterotoxin) produced by *Clostridium difficile*. Toxin A has been characterized (Dove et al., Infect. Immun. 58:480-8, 1990) and its nucleotide and protein (GenBank Accession No. AAA23283) structures are known in the art. The amino acid sequence of *Clostridium difficile* toxin A is provided in SEQ ID NO: 14.

The term "toxin B" or "tcdB" refers to the toxin B protein (cytotoxin) produced by *Clostridium difficile*. The amino acid sequence of *Clostridium difficile* toxin B is provided in SEQ ID NO: 1.

The term "CDB-250" refers to the C-terminal 250-amino-acid region of *Clostridium difficile* toxin B. The sequence of CDB-C250 is set forth in SEQ ID NO: 2. CDB-C250 was identified as a segment unique to toxin B, with no homologous/similar counterpart in toxin A. Thus, it provides a unique region for targeting toxin B with toxin B-specific antibodies and probes for detecting the presence of toxin B.

The term "CDB-750" refers to the 3'-terminal nucleic acid region comprising 750 nucleotides encoding CDB-250.

The term "colonic epithelial cell protein" or "colonic epithelial protein" refers to a protein present within epithelial cells of the colon. Various colonic epithelial proteins include, but are not limited to, non-muscle tropomyosins 1-5, macrophage inflammatory protein 3 alpha, and proteolipid protein 2.

The term "non-muscle tropomyosin" refers to at least one of seven isoforms of non-muscle tropomyosin known including, but not limited to, human tropomyosin 1 (TM1), TM2, TM3, TM4, TM5, TM5a, and TM5b or a non-muscle tropomyosin encoded by any of the genes for tropomyosin 1 (TPM1), TPM2, TPM3, and TPM4.

An "antibody" is given the broadest definition consistent with its meaning in the art, and includes proteins, polypeptides and peptides capable of binding to at least one binding partner, such as a proteinaceous or non-proteinaceous antigen. An "antibody" is a protein including at least one or two, heavy (H) chain variable regions (abbreviated herein as VH), and at least one or two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the FR and CDRs has been precisely defined (see, Kabat, E. A., et al. Sequences of Proteins of Immunological Interest, Fifth Edition, U.S. Department of Health and Human Services, NIH Publication No. 91-3242, 1991, and Chothia, C. et al., J. Mol. Biol. 196:901-917, 1987, which are incorporated herein by reference). In some embodiments, each VH and VL is composed of three CDRs and four FRs, arranged from amino-terminus to carboxy-terminus in the following order: FR1, CDR1, FR2, CDR2, FR3, CDR3, FR4.

An "antibody" includes members of the immunoglobulin superfamily of proteins, of any species, of single- or multiple-chain composition, and variants, analogs, derivatives and fragments of such molecules. Specifically, an "antibody" includes any form of antibody known in the art, including but not limited to, monoclonal and polyclonal antibodies, chimeric antibodies, CDR-grafted antibodies, humanized antibodies, human antibodies, single-chain variable fragments, bi-specific antibodies, diabodies, and antibody fusions.

A "human antibody," is an antibody that has variable and constant regions derived from human germline immunoglobulin sequences. The human antibodies described herein may include amino acid residues not encoded by human germline immunoglobulin sequences (e.g., mutations introduced by random or site-specific mutagenesis in vitro or by somatic mutation in vivo).

An "anti-*Clostridium difficile* antibody" is an antibody that interacts with (e.g., specifically binds to) a protein or other component produced by a *Clostridium difficile* bacterium.

An "anti-toxin antibody" is an antibody or fragment thereof that interacts with a toxin produced by *Clostridium difficile* (e.g., toxin A or toxin B). An anti-toxin antibody, in various aspects, is an antibody that binds to an epitope, e.g., a conformational or a linear epitope, or to a fragment of the full-length toxin protein.

As used herein, "specific binding" or "specifically binds to" refers to the ability of an antibody to: (1) bind to a toxin of *Clostridium difficile* with an affinity of at least $1 \times 10^7 \, M^{-1}$, and (2) bind to a toxin of *Clostridium difficile* with an affinity that is at least two-fold greater than its affinity for a nonspecific antigen.

A "binding domain" is a peptide region, such as a fragment of a polypeptide derived from an immunoglobulin (e.g., an antibody), that specifically binds one or more specific binding partners. If a plurality of binding partners exists, those partners share binding determinants sufficient to detectably bind to the binding domain. In some embodiments, the binding domain is a contiguous sequence of amino acids.

An "epitope" is given its ordinary meaning herein of a single antigenic site, i.e., an antigenic determinant, on a substance (e.g., a protein) with which an antibody specifically interacts, for example by binding. Other terms that have acquired well-settled meanings in the immunoglobulin (e.g., antibody) art, such as a "variable light region," variable heavy region," "constant light region," constant heavy region," "antibody hinge region," "complementarity determining region," "framework region," "antibody isotype," "$F_C$ region," "constant region," "single-chain variable fragment" or "scFv," "diabody," "chimera," "CDR-grafted antibody," "humanized antibody," "shaped antibody," "antibody fusion," and the like, are each given those well-settled meanings known in the art, unless otherwise expressly noted herein.

The $V_H$ or $V_L$ chain of the antibody can further include all or part of a heavy or light chain constant region. In one embodiment, the antibody is a tetramer of two heavy immunoglobulin chains and two light immunoglobulin chains, wherein the heavy and light immunoglobulin chains are interconnected by, e.g., disulfide bonds. The heavy chain constant region includes three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The term "antibody" includes intact immunoglobulins of types IgA, IgG, IgE, IgD, IgM (as well as subtypes thereof), wherein the light chains of the immunoglobulin may be of types kappa or lambda.

"Immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon, and mu constant region genes, as well as the myriad immunoglobulin variable region genes. Full-length immunoglobulin "light chains" (about 25 kDa and 214 amino acids) are encoded by a variable region gene at the $NH_2$-terminus (about 110 amino acids) and a kappa or lambda constant region gene at the COOH-terminus. Full-length immunoglobulin "heavy chains" (about 50 kDa and 446 amino acids), are similarly encoded by a variable region gene (about 116 amino acids) and one of the other aforementioned constant region genes, e.g., gamma (encoding about 330 amino acids). The term "immunoglobulin" includes an immunoglobulin having CDRs from a human or non-human source. The framework of the immunoglobulin can be human, humanized, or non-human, e.g., a murine framework modified to decrease antigenicity in humans, or a synthetic framework, e.g., a consensus sequence.

As used herein, "isotype" refers to the antibody class (e.g., IgM or IgG.sub.1) that is encoded by heavy chain constant region genes.

The term "antigen binding portion" of an antibody (or simply "antibody portion," or "portion"), as used herein, refers to a portion of an antibody that specifically binds to a toxin of *Clostridium difficile* (e.g., toxin B), e.g., a molecule in which one or more immunoglobulin chains is not full length, but which specifically binds to a toxin. Examples of binding portions encompassed within the term "antigen-binding portion" of an antibody include (i) a Fab fragment, a monovalent fragment consisting of the VLC, VHC, CL and CH1 domains; (ii) a F(ab').sub.2 fragment, a bivalent fragment comprising two Fab fragments linked by a disulfide bridge at the hinge region; (iii) a Fd fragment consisting of the VHC and CH1 domains; (iv) a Fv fragment consisting of the VLC and VHC domains of a single arm of an antibody, (v) a dAb fragment (Ward et al., Nature 341:544-546, 1989), which consists of a VHC domain; and (vi) an isolated complementarity determining region (CDR) having sufficient framework to specifically bind, e.g., an antigen binding portion of a variable region. An antigen binding portion of a light chain variable region and an antigen binding portion of a heavy chain variable region, e.g., the two domains of the Fv fragment, VLC and VHC, can be joined, using recombinant methods, by a synthetic linker that enables them to be made as a single protein chain in which the VLC and VHC regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also encompassed within the term "antigen binding portion" of an antibody. These antibody portions are obtained using conventional techniques known to those with skill in the art, and the portions are screened for utility in the same manner as are intact antibodies.

The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or portions thereof with a single molecular composition.

The term "recombinant" antibody, as used herein, refers to antibodies that are prepared, expressed, created, or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes or antibodies prepared, expressed, created, or isolated by any other means that involves splicing of human immunoglobulin gene sequences to other DNA sequences. Such recombinant antibodies include humanized, CDR grafted, chimeric, in vitro-generated (e.g., by phage display) antibodies, and may optionally include constant regions derived from human germline immunoglobulin sequences. Recombinant antibodies also include polypeptide products comprising at least one peptide corresponding to a part of an antibody, such as an Fv fragment, a single-chain antibody, a single-chain $F_v$ (i.e., scFv) molecule, a linear antibody, a diabody, a peptibody, a bi-body (bispecific Fab-scFv), a tribody (Fab-(scFv)2), a hinged or hingeless minibody, a mono- or bi-specific antibody, or an antibody fusion. A peptide corresponds to a part of an antibody if it has a primary amino acid sequence at least 95% identical to a part of an antibody or if it contains at least one domain recognizable by one of skill in the art as an antibody domain. Peptide linkers of about 10-100 amino acids are used where appropriate to link polypeptide domains of a recombinant antibody, as would be known in the art.

As used herein, the term "substantially identical" (or "substantially homologous") refers to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of antibodies, the second antibody has the same specificity and has at least 50% of the affinity of the first antibody. Calculations of "homology" between two sequences are performed as described in Example 2 and such calculations are known in the art.

It is understood that the antibodies and antigen binding portions thereof described herein may have additional conservative or non-essential amino acid substitutions, which do not have a substantial effect on the polypeptide functions. Whether or not a particular substitution will be tolerated, i.e., will not adversely affect desired biological properties, such as binding activity, can be determined as described in Bowie et al., Science, 247:1306-1310, 1990. A "conservative amino acid substitution" is one in which an amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

A "non-essential" amino acid residue is a residue that can be altered from the wild-type sequence of a polypeptide, such as a binding agent, e.g., an antibody, without substantially altering a biological activity, whereas an "essential" amino acid residue results in such a change.

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. 6.3.1-6.3.6, 1989, which is incorporated herein by reference. Aqueous and nonaqueous methods are described in that reference and either can be used. Specific hybridization conditions referred to herein are as follows: 1) low stringency hybridization conditions: 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions: 6×SSC at about 45° C., followed by one or more washes in 0.2×SSC, 0.1% SDS at 60° C.; 3) high stringency hybridization conditions: 6×SSC at about 45° C., followed by one or more washes in 0.2×SSC, 0.1% SDS at 65° C.; and 4) very high stringency hybridization conditions: 0.5 M sodium phosphate, 7% SDS at 65° C., followed by one or more washes at 0.2×SSC, 1% SDS at 65° C.

A "toxin B polypeptide lacking the cytotoxic domain" is a polypeptide fragment of *Clostridium difficile* toxin B that is incapable of inducing cytotoxicity because the cytotoxic domain of the toxin B holo-protein is lacking. Exemplary toxin B polypeptides lacking the cytotoxic domain include the CDB-C250 toxin B fragment containing the C-terminal 250 amino acids of the protein, as well as fragments of the CDB-C250 region containing at least one of the repeat elements whose sequences are disclosed in FIG. 2. As shown in FIG. 2, these repeat elements are each about 20 amino acids in length.

The term "limit of detection" or "LOD" or "sensitivity" as used herein generally refers generally to the lowest analyte (e.g., toxin B, C-terminal fragment thereof, or C-terminal repeat-containing peptide thereof) concentration in a body fluid (e.g., serum) sample that can be detected but not necessarily quantitated as an exact value.

An "anti-tropomyosin antibody" is an antibody or fragment thereof that binds or interacts with a tropomyosin protein (TM), or a fragment thereof. An anti-tropomyosin antibody, in various aspects, binds to an epitope, e.g., a conformational or a linear epitope, or to a fragment of the full-length tropomyosin protein.

The term "heat resistant" or "heat-resistant protein" as used herein refers to a protein which is not denatured by boiling for at least 10 minutes. This is in contrast to most proteins which are denatured by heat treatment.

The term "host cell target protein" includes a protein, and fragments of the protein, present in a cell affected by *Clostridium difficile* toxin B. For example, a host cell target protein includes a colonic epithelial cell protein including, but not limited to, a non-muscle tropomyosin and fragments thereof.

The term "microbial target protein" includes a protein, and fragments or the protein, present in the microbe, i.e. *Clostridium difficile*. For example, a microbial target protein includes *Clostridium difficile* toxin B (tcdB) and fragments thereof, such as CDB-250, the C-terminal 250 amino acids of toxin B.

The term "immunoassay" is a biochemical test that measures the presence or concentration of a substance in solutions that frequently contain a complex mixture of substances. Such assays are based on the unique ability of an antibody to bind with high specificity to one or more antigens. Examples of immunoassays include, but are not limited to, Western blots, EIAs or ELISAs, immunohistochemistry, and immunofluorescence.

A "control," as used herein, refers to an active, positive, negative or vehicle control. As will be understood by those of skill in the art, controls are used to establish the relevance of experimental results, and provide a comparison for the condition being tested.

Unless otherwise defined, all technical and scientific terms used herein have the meaning commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The following abbreviations are used throughout.
Ab Antibody
CDAD *Clostridium difficile*-associated diarrhea
CDB-250 C-terminal 250-amino-acid region of *Clostridium difficile* toxin B
CDB-750 3'-terminal 750 nucleotide region encoding CDB-250
CDI *Clostridium difficile* infection
DNA Deoxyribonucleic acid
EIA Enzyme immunoassay
ELISA Enzyme-linked immunosorbent assay
FBS Fetal bovine serum
mAb Monoclonal antibody
μg Microgram
mL Milliliter
mM Millimolar
min Minute(s)
ng Nanogram
PCR Polymerase chain reaction
RNA Ribonucleic acid
RT-PCR Reverse-transcriptase polymerase chain reaction
SDS Sodium dodecyl sulfate
tcdB *Clostridium difficile* toxin B
TM Tropomyosin protein
TPM Tropomyosin gene The section headings are used herein for organizational purposes only, and are not to be construed as in any way limiting the subject matter described. *Clostridium difficile* infection (CDI)/*Clostridium difficile*-associated Diarrhea (CDAD)

The present section provides a brief summary of CDAD/CDI to the extent that such a summary will facilitate a better understanding of the methods of the present disclosure. In one embodiment, the disclosure provides new methods for CDAD/CDI diagnosis. Making a definitive diagnosis of CDAD/CDI through laboratory testing is uniformly complicated due to the high number of hospitalized patients that will have positive stool exams, not necessarily due to disease, but from colonization with *Clostridium difficile* associated with prolonged hospitalization. This highlights the fact that asymptomatic carriers outnumber those with CDAD/CDI by several-fold.

The diagnostic dilemma for CDAD/CDI in children is a particular problem. Many reports have demonstrated stool-positivity rates for culture approaching 50% during the first year of life, often with cytotoxin-producing strains. While this colonization is generally considered to have no clinical consequence, one study has found that newborns with toxin-positive feces appear to have more loose stools and longer hospital stays than those with toxin-negative stool exams. Currently, the only definitive diagnostic test for these young persons requires a potentially painful colonoscopy examination to visually examine the colon. Improved diagnostics, as provided herein, would dramatically benefit these young patients.

The diagnosis of CDAD/CDI currently is based on clinical and laboratory findings because of suboptimal laboratory diagnostic capabilities. A case definition for the usual presentation of CDAD/CDI includes: (i) diarrhea, typically defined as at least six watery stools over 36 hours, (or eight stools during 48 hours), (ii) a history of antimicrobial agent therapy within eight weeks of the onset of diarrhea, (iii) pseudomembranes seen upon lower gastrointestinal endoscopy (this is required for the diagnosis of colitis), or a stool sample positive for the presence of toxin B (or toxins A and B), or a toxigenic isolate of *Clostridium difficile* (toxin B, or A and B) recovered from the stool, and (iv) no other reason for diarrhea.

In the laboratory, detection of *Clostridium difficile* and its toxin(s) is the mainstay of diagnostic testing, but this detection does not define the disease. Actual disease diagnosis requires more than the presence of the *Clostridium difficile* organism or its toxin(s). The present disclosure provides an improved method of diagnosis as it provides a means of testing for the presence of both host response (colonic epithelial cell protein) and bacterial toxin (*Clostridium difficile* toxin) in a stool sample or fluid exposed to a stool sample of a subject.

*Clostridium Difficile* Toxins A and B

The methods according to the disclosure include detecting *Clostridium difficile* toxins in a subject. The present section provides a brief summary of *Clostridium difficile* toxins to the extent that such a summary will facilitate a better understanding of the disclosed methods. *Clostridium difficile* produces two major exotoxins—toxin A, classically considered an enterotoxin, and toxin B with more potent cytotoxic activity in tissue culture cells. Both of these toxins are high molecular weight proteins (280-300 kDa) that catalyze covalent modification of Rho proteins, ultimately leading to the depolymerization of actin filaments and cell death. Both toxins have been reported to be lethal to mice when injected parenterally; however, toxin B can cause disease even in the absence of toxin A. It recently has been published that toxin B is the *Clostridium difficile* virulence factor for CDI and is the more significant contributor to the CDI constellation of diseases (Lyras et al, Nature 458:1176-9, 2009). With the historical background that assumed both toxins were important in disease, it is not surprising that some in the field were untroubled by the difficulty in experimentally or diagnostically distinguishing the presence of toxin A and the presence of toxin B by antibody methods. Understanding these important biologic observations led to the development of the methods described in the disclosure.

Importantly, *Clostridium difficile* toxin A and toxin B share significant sequence similarities. Based on protein structure analyses, however, the C-terminal 250 amino acids of toxin B (CDB-250) were identified as a segment unique to toxin B, with no homologous/similar counterpart in toxin A. This finding provided the motivation to isolate this segment and use it for antibody preparation for the diagnosis of CDI or CDAD. Thus, CDB-C250 was identified as a region within which toxin B-specific epitopes are located, i.e., epitopes unique to toxin B and not shared with toxin A. Therefore, the methods of the present disclosure also include detecting CDB-250, or a fragment thereof, as an indicator of the presence of the microbial target protein, *Clostridium difficile* toxin B or "tcdB."

In exemplary aspects, the disclosure includes a variety of methods of detecting tcdB, generally, and CDB-250 more specifically. Such methods include testing for tcdB or CDB-250 protein, DNA, or both tcdB protein and DNA. Thus, in various aspects, the methods of the disclosure include the use of antibodies specific for tcdB or CDB-250. In other aspects, amplification of the tcdB gene or a portion of the tcdB gene, e.g. the nucleotide sequence encoding CDB-250, is used. In further aspects, the polymerase chain reaction (PCR), RT-PCR, or real-time PCR is used for detection of tcdB or CDB-250. In one aspect, real-time PCR for diagnosing CDAD can be carried out using the methods of Peterson et al. (Clin. Infect. Dis. 45: 1152-60, 2007) or modifications of those methods.

In a specific aspect, testing for the presence of CDB-C250 polypeptide or a fragment thereof or CDB-250 DNA (a region of tcdB comprising 750 nucleotides in length at the 3' end of the tcdB coding region) or a fragment thereof provides optimal results for detecting the presence of the microbial target tcdB. Thus, the methods of the disclosure include the use of antibodies and antibody fragments that specifically recognize or bind to the C-terminal domain (250 amino acids) of toxin B of *Clostridium difficile*. In particular, monoclonal antibodies are provided. In certain embodiments, these monoclonal antibodies are produced in mice expressing immunoglobulin gene segments (described below). Combinations of anti-toxin B antibodies are also provided, as are any form of recombinant antibody or antibody fragment specifically recognizing *Clostridium difficile* toxin B, such as the C-terminal 250-amino-acid region of intact toxin B, regardless of whether such region is found in intact toxin B or a fragment thereof.

The methods according to the disclosure include contacting a biological sample with an anti-toxin B-specific antibody or antigen-binding portion under conditions suitable for binding and diagnosing *Clostridium difficile* infection and/or CDAD on the basis of the binding detected.

Toxin Antibodies

In general, animals are immunized with antigens expressed by *Clostridium difficile* to produce antibodies. For producing anti-toxin antibodies, what had been known in the art was immunization with inactivated toxins, or toxoids. Toxins can be inactivated, e.g., by treatment with formaldehyde, SDS, glutaraldehyde, peroxide, or oxygen treatment. Mutant *Clostridium difficile* toxins with reduced toxicity can be produced using recombinant methods (see, e.g., U.S. Pat. Nos. 5,085,862; 5,221,618; 5,244,657; 5,332,583; 5,358,868; and 5,433,945). For example, mutants containing deletions or point mutations in the toxin active site can be made. Recombinant fragments of the toxins can be used as immunogens. These techniques, however, result in the use of immunogens that differ from the desired target of any elicited antibody. Another approach is to inactivate the toxin by treatment with UDP-dialdehyde. This approach also results in immunogens that differ from the target of the elicited antibody. Disclosed herein is an advance in methods of producing anti-toxin B-specific antibodies comprising the use of an immunogen derived from the C-terminal 250-amino-acid polypeptide of *Clostridium difficile* toxin B in a native form. That is, the polypeptide comprising the C-terminal 250-amino-acid region of toxin B and/or the intact toxin B from which the C-250 fragment may be physically derived, are not used as immunogens or sources of immunogens in a denatured or otherwise inactivated form.

The antibodies of the present disclosure are said to be immunospecific or specifically binding if they bind to antigen with a $K_a$ of greater than or equal to about $10^4$ $M^{-1}$, $10^5$ $M^{-1}$, $10^6$ $M^{-1}$, $10^7$ $M^{-1}$, $10^8$ $M^{-1}$, $10^9$ $M^{-1}$, or $10^{10}$ $M^{-1}$. The anti-toxin B antibodies bind to different naturally occurring forms of *Clostridium difficile* toxin B, including intact toxin B and fragments thereof. The monoclonal antibodies disclosed herein have affinity for the C-terminal 250-amino-acid portion of *Clostridium difficile* toxin B and are characterized by a dissociation equilibrium constant (Kd) of at least about $10^{-4}$ M, at least about $10^{-7}$ M, at least about $10^{-8}$ M, at least about $10^{-9}$ M, at least about $10^{-10}$ M, at least about $10^{-11}$ M, or at least about $10^{-12}$ M. Monoclonal antibodies and antigen-binding fragments thereof that are suitable for use in the methods of the disclosure are capable of specifically binding to toxin B. Such affinities may be readily determined using conventional techniques, such as by equilibrium dialysis; by using the BIAcore 2000 instrument, using general procedures outlined by the manufacturer; by radioimmunoassay using $^{125}$I labeled toxin B; or by other methods known in the art. The affinity data is analyzed, for example, by the method of Scatchard et al., Ann N.Y. Acad. Sci., 51:660 (1949). Thus, it will be apparent that preferred toxin B antagonists will exhibit a high degree of specificity for toxin B and will bind with substantially lower affinity to other molecules, including *Clostridium difficile* toxin A.

The antigen to be used for production of antibodies is, e.g., intact toxin B, a C-terminal fragment of toxin B of 250 amino acids (i.e., CDB-C250), or a fragment of CDB-C250 containing at least one repeat element from CDB-C250, which is optionally fused to another polypeptide that facilitates epitope display.

Polyclonal antibodies are raised in animals by multiple subcutaneous (sc) or intraperitoneal (ip) injections of, e.g., the CDB-C250 fragment of toxin B and an adjuvant. An improved antibody response may be obtained by conjugating, e.g., CDB-C250 to a protein that is immunogenic in the species to be immunized, e.g., keyhole limpet hemocyanin, serum albumin, bovine thyroglobulin, or soybean trypsin inhibitor, using a bifunctional or derivatizing agent such as maleimidobenzoyl sulfosuccinimide ester (conjugation through cysteine residues), N-hydroxysuccinimide (through lysine residues), glutaraldehyde, succinic anhydride or other agents known in the art.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later, the animals are boosted with one fifth to one tenth the original amount of peptide or conjugate in Freund's complete adjuvant by subcutaneous injection at multiple sites. At 7-14 days post-booster injection, the animals are bled and the serum is assayed for antibody titer. Animals are boosted until the titer plateaus. The animal is typically boosted with the conjugate of the same antigen, but conjugation to a different protein and/or through a different cross-linking reagent are contemplated. Conjugates also can be made in recombinant cell culture as protein fusions. Also, aggregating agents such as alum are suitably used to enhance the immune response.

Monoclonal antibodies are made using, e.g., the hybridoma method first described by Kohler et al., Nature, 256:495 (1975), or by recombinant DNA methods. In the hybridoma method, a mouse or other appropriate host animal, such as a hamster or macaque monkey, is immunized to elicit lymphocytes that produce or are capable of producing antibodies that will specifically bind to the protein, e.g., CDB-C250, used for immunization. Alternatively, lymphocytes may be immunized in vitro. Lymphocytes then are fused with myeloma cells using a suitable fusing agent, such as polyethylene glycol, to form a hybridoma cell (coding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), because those substances prevent the growth of HGPRT-deficient cells.

Exemplary myeloma cells are those that fuse efficiently, support stable high-level production of antibody by the selected antibody-producing cells, and are sensitive to a medium. Human myeloma and mouse-human heteromyeloma cell lines also have been described for the production of human monoclonal antibodies (Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. The binding specificity of monoclonal antibodies produced by hybridoma cells is determined, e.g., by immunoprecipitation or by an in vitro binding assay, such as a radioimmunoassay (RIA) or an enzyme-linked immunosorbent assay (ELISA). The binding affinity of the monoclonal antibody is, for example, determined by Scatchard analysis (Munson et al., Anal. Biochem., 107:220 (1980)).

After hybridoma cells are identified that produce antibodies of the desired specificity, affinity, and/or activity, the clones are subcloned by limiting dilution procedures and grown by standard methods (coding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

An antigen-antibody reaction is described in this paragraph in the context of immobilized antigen interacting with free antibody in an ELISA embodiment. Initially, 96-well plates are coated overnight at 48° C. with 100 μL per well of toxin B (25 μg/mL) in carbonate-bicarbonate buffer 50 mM, pH 9.6 (Sigma-Aldrich, St Louis, Mo.). Antibody preparations are diluted appropriately, e.g., 1:50 to 1:20, in 2% BSA, 0.05% Tween phosphate buffer saline (PBST), as would be known in the art. Diluted antibody is then added to the plate and incubated for two hours at room temperature. Toxin B-specific antibodies are detected with horseradish peroxidase-conjugated goat secondary antibody (KPL, Gaithersburg, Md.) diluted, e.g., 1:2500. The immobilized horseradish peroxidase is then revealed by adding tetramethylbenzidine peroxidase substrate (KPL) to the wells, and results are obtained using a microplate reader at 650 nm.

DNA encoding the monoclonal antibodies are also contemplated by the disclosure and may be isolated and sequenced from the hybridoma cells using conventional procedures (e.g., by using oligonucleotide probes that are capable of binding specifically to genes encoding the heavy and light chains of the monoclonal antibodies). Once isolated, the DNA may be recombined in expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies is well known in the art.

One type of animal useful in generating human monoclonal antibodies is a transgenic mouse that expresses human immunoglobulin genes rather than its own mouse immunoglobulin genes. Such transgenic mice, e.g., HuMAb® mice, contain human immunoglobulin gene miniloci that encode unrearranged human heavy (μ and γ) and κ light chain immunoglobulin sequences, together with targeted mutations that inactivate the endogenous μ and κ chain loci (see, e.g., Lonberg, et al., Nature 368: 856-59, 1994, and U.S. Pat. No. 5,770,429). Accordingly, the mice exhibit reduced expression of mouse IgM or K, and in response to immunization, the introduced human heavy and light chain transgenes undergo class switching and somatic mutation to generate high affinity human IgGκ monoclonal antibodies (Lonberg, et al., supra; reviewed in Lonberg, N. Handbook of Experimental Pharmacology 113: 49-101, 1994; Lonberg, et al., Intern. Rev. Immunol., 13: 65-93, 1995; Harding, et al., Ann. N.Y. Acad. Sci., 764: 536-46, 1995).

The preparation of such transgenic mice is described in further detail in Taylor et al., Nucl. Acids Res. 20:6287-6295, 1992; Chen et al., Internl. Immunol. 5: 647-656, 1993; Tuaillon et al., Proc. Natl. Acad. Sci. (USA) 90:3720-4, 1993; Choi et al., Nature Genetics 4:117-23, 1993; Chen et al, EMBO J. 12: 821-30, 1993; Tuaillon et al., J. Immunol. 152: 2912-20, 1994; Taylor et al., Internl. Immunol. 6: 579-91, 1994; and Fishwild et al., Nature Biotechnology 14: 845-51, 1996. See also, U.S. Pat. Nos. 5,545,806; 5,569,825, 5,625,126, 5,633, 425, 5,661,016, 5,770,429, 5,789,650, 5,814,318, 5,874,299 and 5,877,397, and PCT Publication Nos. WO 01/14424, WO 98/24884, WO 94/25585, WO 93/1227, and WO 92/03918.

To generate fully human monoclonal antibodies to an antigen, HuMAb® mice are immunized with an immunogen, as described by Lonberg et al. Nature, 368: 856-59, 1994; Fishwild et al., Nature Biotechnology 14: 845-51, 1996 and WO 98/24884. The mice are 6-16 weeks of age upon the first immunization. For example, a purified preparation of the peptide containing the C-terminal 250 amino acids of toxin B can be used to immunize the HuMAb® mice intraperitoneally.

HuMAb® transgenic mice respond best when initially immunized intraperitoneally (IP) with antigen in complete Freund's adjuvant, followed by IP immunizations every other week (typically up to a total of 6) with antigen in incomplete Freund's adjuvant. The immune response is monitored over the course of the immunization protocol with plasma samples being obtained by retro-orbital bleeds. The plasma is screened, for example by ELISA or flow cytometry, and mice with sufficient titers of anti-toxin human immunoglobulin are used for fusions. Mice are optionally boosted intravenously with antigen 3 days before sacrifice and removal of the spleen. It is expected that 2-3 fusions for each antigen may need to be performed.

Mouse splenocytes are isolated and fused with PEG to a mouse myeloma cell line using standard protocols. The resulting hybridomas are then screened for the production of antigen-specific antibodies. For example, single-cell suspensions of splenic lymphocytes from immunized mice are fused to one-sixth the number of P3×63-Ag8.653 or other nonsecreting mouse myeloma cells (ATCC, CRL 1580) with 50% PEG. Cells are plated at approximately $2 \times 10^4$ in flat-bottom microtiter plates, followed by a two-week incubation in selective medium containing 20% fetal clone serum, 18% "653" conditioned medium, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamicin and 1×HAT medium (Sigma; the HAT is added 24 hours after the fusion). After two weeks, cells are cultured in medium in which the HAT is replaced with HT. Supernatants from individual wells are then screened by ELISA for human anti-toxin B monoclonal IgM and IgG antibodies. The antibody-secreting hybridomas are replated, screened again and, if still positive for human IgG, anti-toxin monoclonal antibodies are subcloned at least twice by limiting dilution. The stable subclones are then cultured in vitro to generate small amounts of antibody in tissue culture medium for characterization.

The repertoire in the transgenic mouse will ideally approximate that shown in a non-transgenic mouse, usually at least about 10% as high, preferably 25 to 50% or more as high. Generally, at least about a thousand different immunoglobulins (ideally IgG), preferably $10^4$ to $10^6$ or more, will be produced, depending primarily on the number of different V, J, and D regions introduced into the mouse genome. Typically, the immunoglobulins will exhibit an affinity for preselected antigens of at least $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, or greater, e.g., up to $10^{13}$ $M^{-1}$ or greater.

HuMAb mice can produce B cells that undergo class-switching via intra-transgene switch recombination (cis-switching) to express immunoglobulins reactive with the toxin. The immunoglobulins can be human sequence antibodies, wherein the heavy and light chain polypeptides are encoded by human transgene sequences, which may include sequences derived by somatic mutation and V region recombined joints, as well as germline-encoded sequences. These human-sequence immunoglobulins are referred to as being effectively identical to a polypeptide sequence encoded by a human VL or VH gene segment and a human JL or JH segment, even though other non-germline sequences may be present as a result of somatic mutation and differential V-J and V-D-J recombination joints. With respect to such human sequence antibodies, the variable regions of each chain are typically at least 80 percent encoded by human germline V, J, and, in the case of heavy chains, D gene segments. Frequently at least 85 percent of the variable regions are encoded by human germline sequences present on the transgene. Often 90 or 95 percent or more of the variable region sequences are encoded by human germline sequences present on the transgene. However, since non-germline sequences are introduced by somatic mutation and VJ and VDJ joining, the human sequence antibodies will frequently have some variable region sequences (and less frequently constant region sequences) that are not encoded by human V, D, or J gene segments, as found in the human transgene(s) in the germline of the mice. Typically, such non-germline sequences (or individual nucleotide positions) will cluster in or near CDRs, or in regions where somatic mutations are known to cluster.

Some human sequence antibodies that bind to toxin B result from isotype switching, such that human antibodies comprising a human sequence gamma chain (such as γ1, γ2, or γ3) and a human sequence light chain (such as κ) are produced. Such isotype-switched human sequence antibodies often contain one or more somatic mutation(s), typically in the variable region and often in or within about 10 residues of a CDR, as a result of affinity maturation and selection of B cells by antigen, particularly subsequent to secondary (or subsequent) antigen challenge. These high-affinity human sequence antibodies have binding affinities of at least or about $1 \times 10^9$ $M^{-1}$, typically at least or about $5 \times 10^9$ $M^{-1}$, frequently more than $1 \times 10^{10}$ $M^{-1}$, and sometimes $5 \times 10^{10}$ m to $1 \times 10^{11}$ $M^{-1}$ or greater. Anti-toxin antibodies can also be raised in other animals, including but not limited to non-transgenic mice, humans, rabbits, goats, and chicken.

In aspects, testing for toxin B, i.e. tcdB, is carried out by an immunoassay. Suitable immunoassays include, but are not limited to, Western blot analysis, immunohistochemistry, immunofluorescence, ELISA, or EIA. In some methods, a biological sample, e.g., an isolated stool sample, or a fluid exposed to a sample, is contacted with a tcdB or CDB-C250 antibody or fragment thereof under conditions suitable for binding. The conditions suitable for binding include any set of conditions suitable or compatible with specific binding of an antigen and a cognate antibody or fragment thereof known in the art. In some embodiments, the antibody or antibody fragment is attached to a solid support, such as a glass or plastic chip or bead.

In exemplary aspects, the methods of the disclosure include various other tests or assays for detecting the presence of tcdB. In certain aspects, testing for tcdB is carried out by toxigenic culture or a cytotoxicity assay. In one aspect, an assay for production of tcdB in its various forms, and in particular CDB-C250, is an in vitro assay for cytotoxicity. In the cytotoxicity assay, *Clostridium difficile* strains are grown to purity, then 3 to 5 colonies are selected and inoculated into anaerobic broth and incubated anaerobically at 35-37° C. for 3 to 7 days. Cytotoxin testing is performed with the TechLab *Clostridium difficile* Tox-B (Toxin/Antitoxin) Kit (TechLab, Blacksburg, Va.). The TechLab *Clostridium difficile* Tox-B test relies on a tissue culture format to detect cytotoxic activity, in the form of cell rounding, in fecal specimens. The test identifies *Clostridium difficile* toxin B by using specific anti-toxin. Testing on isolated *Clostridium difficile* colonies is carried out by using 2-3 mL of anaerobic chopped-meat glucose broth suspension grown with *Clostridium difficile* and then centrifuged at 4,000×g for 10 minutes and subsequently filtered through a 0.45 μm Spin-X filter. To determine the presence of toxin, two tubes of MRC-5 cells (ViroMed Laboratories) are set up for each sample. Sample alone and sample plus anti-toxin are tested with the TechLab *Clostridium difficile* Tox-B (Toxin/Antitoxin) Kit. Test results are determined after 24 hours and 48 hours of incubation, according to the manufacturer's instructions. The sample is considered toxigenic if a cytopathic effect is observed in the toxin tube and not in the tube containing added anti-toxin. The in vitro cytotoxicity assay is amenable to the assessment of toxin B production by *Clostridium difficile* isolates, such as *Clostridium difficile* isolates from patient stool samples. In addition, an ELISA or a modification of the in vitro cytotoxicity assay is useful in assessing the cytotoxiciy of the various recombinantly produced toxin B proteins, peptides or peptide fragments, e.g., CDB-C250. In testing toxin B proteins, routine optimization will reveal the quantity of protein to use in an ELISA or to add to the TOX-B kit reagents to obtain reliable assay results, and the assay can be performed without the need for cell culturing.

In other aspects, testing for tcdB is carried out by RT-PCR, PCR, or real-time PCR. In a particular aspect, a method for detecting the presence of tcdB in a subject comprises obtaining a biological sample from the subject; adding to the sample a pair of PCR primers capable of amplifying a region of tcdB between about 20-750 nucleotides, or between about 100-750 nucleotides, or between about 200-750 nucleotides in length at the 3' end of the tcdB coding region, i.e., encoding part or all of CDB-C250, under polymerase chain reaction (PCR) conditions; carrying out a PCR; and diagnosing the presence of tcdB in the sample.

Pathophysiology of Toxin B

The present section provides a brief summary of the pathophysiology of tcdB to the extent that such a summary will facilitate a better understanding of the methods of the present disclosure. The pathophysiology of toxin B action is considered to be disruption of the actin cytoskeleton and, therefore, an assay to measure the effects of toxin B on human host colonic tissue was developed. Cell adhesion is dependent on the function of actin cytoskeleton and the effects of

*Clostridium difficile* toxin result in accelerated dissociation of colonic epithelial cells. Therefore, in some aspects, the present disclosure takes advantage of an increase in colonic epithelial proteins and fragments thereof in the patient's stool as an indication of host response to *Clostridium difficile* infection. Thus, colonic epithelial proteins, i.e., non-muscle tropomyosins, and fragments thereof in the stool are targeted as a diagnostic marker(s) for CDAD/CDI.

Tropomyosin(s)

The disclosure includes methods for detecting CDAD/CDI by detecting an increase in heat-resistant colonic epithelial cytoskeleton proteins, or fragments thereof, in a stool specimen or a fluid exposed to the stool specimen of a subject. In exemplary aspects, colonic epithelial cytoskeleton proteins are non-muscle tropomyosin(s). The present section provides a brief summary of tropomyosins to the extent that such a summary will facilitate a better understanding of the methods of the present disclosure.

Tropomyosin (TM) is an abundant cytoskeletal protein of approximately 33 kDa present in both muscle and non-muscle cells (Lin et al., Int. Rev. Cytol. 170:1-38, 1997; Perry et al., J. Muscle Res. Cell Motif. 22:5-49, 2001). In muscle, tropomyosin and the troponin complex associate with actin in myofibrils and regulate muscle contraction by regulating the binding of myosin with actin. In non-muscle cells, tropomyosin has been implicated in regulating actin filament stability, cell shape, intracellular granule movement, and cytokinesis (Lin et al., supra). To date, at least seven isoforms of non-muscle human tropomyosin (TM) are known including, but not limited to, TM1, TM2, TM3, TM4, TM5, TM5a, and TM5b. The disclosure includes methods of detecting the various isoforms of non-muscle tropomyosin, including isoforms which are expressed by alternative promoters and alternative RNA processing of four genes, TPM1, TPM2, TPM3, TPM4 (Perry et al., supra). Thus, the disclosure includes detection of any protein products (TM) of TPM1, TPM2, TPM3, TPM4, and all splice variants thereof.

In exemplary aspects, non-muscle tropomyosin or fragments thereof in the stool is an indicator of the release of cytoskeleton protein from *Clostridium difficile*-infected colonic epithelial cells, i.e., indicating that *Clostridium difficile* has elicited a host response to infection. In further aspects, non-muscle tropomyosin is used because: (1) non-muscle tropomyosin is an abundant structural protein in colonic epithelial cells; (2) non-muscle tropomyosin is heat-resistant and, therefore, heat treatment can be used to remove contaminating proteins in the stool sample; (3) methods were developed to enrich and specifically detect non-muscle tropomyosin; and (4) the baseline level of non-muscle tropomyosin in normal human stool due to normal epithelial turnover is much lower than that in CDI, in which massive cytoskeleton decomposition in colonic epithelial cells occurs, causing the release of large amounts of actin cytoskeletal tropomyosin proteins, and fragments thereof, into the colon and stool.

Tropomyosin Antibodies

In exemplary embodiments, methods use antibodies directed against non-muscle tropomyosin. In one aspect, the antibodies are monoclonal antibodies directed against human non-muscle tropomyosin. These antibodies were produced in the form of hybridoma ascites or cell culture supernatant and were purified in the form of IgG using protein G affinity chromatography as described previously (Yu et al, J. Biol. Chem. 276:15753-60, 2001). Anti-tropomyosin antibodies used in the detection of non-muscle tropomyosin include, but are not limited to, CG1, CGβ6, LC24, CG3, and LC1. Mouse anti-tropomyosin isoform mAbs, CG1 against TPM1, CGβ6 against TPM2 and TPM3, LC24 against TPM4, and CG3 against TPM5 were described previously (Lin et al., J. Cell Biol. 107: 563-72, 1988; Novy et al., Cell Motil. Cytoskeleton 26: 248-61, 1993; Warren et al., J. Cell Biol. 129: 697-708, 1995; Lin et al., Int. Rev. Cytol. 170:1-38, 1997)). LC1 reacts with human isoforms 5 and 4 (TPM5/4 fusion protein (Labome, Developmental Studies Hybridoma Bank at the University of Iowa, Iowa City, Iowa). Monoclonal antibody CH1 (Abcam, Cambridge, UK) does not cross-react with non-muscle isoforms of tropomyosin and, therefore, is used as a control to exclude muscle tropomyosin isoforms.

The non-muscle tropomyosin antibodies are used in different types of methodologies known in the art for detecting the presence of protein in a sample. Such methods include, but are not limited to, immunoassays. Such immunoassays include, but are not limited to, immunoblots, Western blot analysis, immunohistochemistry, immunofluorescence, EIA and ELISA.

Sample Collection and Preparation

In exemplary embodiments, testing for CDAD/CDI is carried out in a stool sample or a fluid exposed to a stool sample. In aspects of the disclosure, the stool sample is a watery or loose stool.

The disclosure includes methods of detecting host cell protein and fragments thereof in a patient's stool sample or fluid exposed to a stool sample. In exemplary aspects, the presence of non-muscle tropomyosin in the stool is detected using one or more of the anti-tropomyosin antibodies described herein.

In exemplary embodiments, the stool specimen or fluid exposed to a stool specimen is diluted in a buffer of neutral pH, e.g., $ddH_2O$, and subject to boiling (i.e., 100° C.) for a period of time. The period of time can range from a few seconds to about 30 minutes or more. In exemplary aspects, boiling can occur for about 1, about 5, about 10, about 15, about 20, about 25, about 30, about 35, about 40, about 45, about 50, about 55, about 60 seconds, or for about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 35, about 40, about 45, about 50, about 55, or about 60 minutes, or for about 1, about 2, about 3, about 4, about 5, about 6, about 7, about 8, about 9, or about 10 hours.

In exemplary aspects, the specimen or fluid exposed to the specimen is further cooled on ice and subjected to centrifugation for collection of a supernatant. In exemplary aspects, the supernatant is further subjected to isoelectric point precipitation to enrich for tropomyosin. In exemplary aspects, the enriched tropomyosin is adjusted to a pH of about 4.6 with hydrochloric acid and subjected to centrifugation in a microcentrifuge at 12,000×g at 4° C. for 30 minutes to collect tropomyosin in a pellet.

In exemplary aspects, the pH is adjusted from about 3.0 to about 6.0. In more exemplary aspects, the pH is adjusted from about 4.0 to about 5.0. In even more exemplary aspects, the pH is adjusted from about 4.5 to about 4.7. In certain aspects, the pH is about 4.6.

Kits

The disclosure includes kits for diagnosing CDAD/CDI. A kit of the present disclosure comprises reagents for detecting a colonic epithelial cell protein, or a fragment thereof, including, but not limited to, a non-muscle tropomyosin in a stool specimen or fluid exposed to the stool specimen. In an exemplary aspect, a suitable kit comprises reagents for detecting a colonic epithelial cell protein, wherein the colonic epithelial cell protein is selected from the group consisting of non-muscle tropomyosin 1, non-muscle tropomyosin 2, non-muscle tropomyosin 4, and non-muscle tropomyosin 5. A suitable kit also comprises reagents for detecting *Clostridium difficile* toxin A or toxin B. In an exemplary aspect, the kit comprises reagents for detecting CDB-250 or CDB-750, or fragments thereof. In an exemplary aspect, the kit comprises instructions for using the reagents to make a diagnosis of CDAD/CDI. A kit of the present disclosure can further comprise reagents for detecting a C-terminal 250-amino-acid fragment of *Clostridium difficile* toxin B polypeptide, or a fragment thereof, or a 3'-terminal 750-nucleotide fragment of a *Clostridium difficile* toxin B nucleic acid molecule, or a fragment thereof.

In an exemplary aspect, a kit comprises anti-tropomyosin antibodies, including antibodies that specifically bind a tropomyosin isoform, or a fragment thereof, encoded by a tropomyosin gene selected from the group consisting of: tropomyosin 1, tropomyosin 2, tropomyosin 3, and tropomyosin 4. In a further exemplary aspect, a kit comprises an antibody that binds a non-muscle tropomyosin isoform 5. The anti-tropomyosin antibody can be a monoclonal antibody, a polyclonal antibody, a human antibody, a humanized antibody, or a chemically modified derivative of an antibody.

In an exemplary aspect, the disclosure includes kits for diagnosing CDAD/CDI wherein the reagent for detecting *Clostridium difficile* toxin B, or a fragment thereof, is an antibody or antibody fragment that binds *Clostridium difficile* toxin B, or a fragment thereof. In exemplary aspects, the antibody or antibody fragment binds CDB-250, or a fragment thereof, wherein the antibody or antibody fragment does not detectably bind to *Clostridium difficile* toxin A. In some aspects, the antibody or antibody fragment specifically binds to a polypeptide comprising the sequence selected from the group consisting of SEQ ID NOS: 3-13. In exemplary aspects, the kit comprises an antibody, or a fragment thereof, produced by a hybridoma selected from the group consisting of the 3H10 hybridoma, the 1C11 hybridoma, the 2C10 hybridoma, the 3E1 hybridoma, the 3G8 hybridoma and the 4B3 hybridoma.

In exemplary aspects, the kits comprise an antibody or antibody fragment that comprises a heavy chain CDR1 amino acid sequence selected from the group consisting of SEQ ID NOS: 39, 42, 45, 48, 51 and a variant thereof in which at most two amino acids have been changed, or a consensus sequence thereof; a heavy chain CDR2 amino acid sequence selected from the group consisting of SEQ ID NOS: 40, 43, 46, 49, 52 and a variant thereof in which at most two amino acids have been changed or a consensus sequence thereof; and a heavy chain CDR3 amino acid sequence selected from the group consisting of SEQ ID NOS: 41, 44, 47, 50, 53 and a variant thereof in which at most two amino acids have been changed, or a consensus sequence thereof.

In exemplary aspects, the kits comprise an antibody or antibody fragment that comprises a light chain CDR1 amino acid sequence selected from the group consisting of SEQ ID NOS: 25, 27, 30, 33, 36 and a variant thereof in which at most two amino acids have been changed; a light chain CDR2 amino acid sequence selected from the group consisting of SEQ ID NOS: 26, 28, 31, 34, 37 and a variant thereof in which at most two amino acids have been changed; and a light chain CDR3 amino acid sequence selected from the group consisting of SEQ ID NOS: 29, 32, 35, 38 and a variant thereof in which at most two amino acids have been changed.

In exemplary aspects, the kits include reagents for detecting CDB-750, or a fragment thereof. Such reagents include one or more nucleotide primers that specifically bind CDB-750, or a fragment thereof.

Each publication, patent application, patent, and other reference cited herein is incorporated by reference in its entirety to the extent that it is not inconsistent with the present disclosure.

It is understood that the examples and embodiments described herein are for illustrative purposes only and that various modifications or changes in light thereof will be suggested to persons skilled in the art and are to be included within the spirit and purview of this application and the scope of the appended claims.

EXAMPLES

Additional aspects and details of the disclosure will be apparent from the following examples, which are intended to be illustrative rather than limiting.

Example 1

Cloning and Expression of Toxin B and CDB-C250

*Clostridium difficile* toxin A and toxin B share significant sequence similarities, which is the primary reason that past attempts to develop high-affinity antibody directed against toxin B (for use in diagnostic tests) have failed. A comparison of the amino acid sequences of *Clostridium difficile* toxin A and *Clostridium difficile* toxin B was performed, as described in Example 2. Based on protein structure analysis, the C-terminal 250 amino acids of toxin B (CDB-C250) were identified as a segment unique to toxin B, with no similar counterpart in toxin A.

The coding region for toxin B was obtained using conventional cloning technologies. Initially, genomic DNA was extracted from *Clostridium difficile* strain ATCC 43255 (a strong toxin B-producing isolate). PCR was then used to amplify the toxin B coding region using the extracted genomic DNA as template. Amplified products were cloned and a DNA encoding the C-terminal 250 amino acids of toxin B was identified. This DNA fragment was then cloned into a prokaryotic expression plasmid (pAED4) for protein expression in *E. coli*. More particularly, the DNA encoding CDB-C250 was cloned in the T7 RNA polymerase-based expression plasmid pAED4 and the resulting clone was used to transform BL21(DE3)pLysS *E. coli* cells. Freshly transformed bacteria were cultured in 2× tryptone-yeast broth containing ampicillin and chloramphenicol at 37° C. with vigorous shaking. The culture was induced during log-phase of growth with 0.4 mM isopropyl-1-thio-β-D-galactopyranoside. After 3 additional hours of culture, the bacterial cells were harvested by centrifugation and lysed by three passages through a French Press. The bacterial lysate was fractionated by ammonium sulfate precipitation, dialyzed and separated on a DE52 anion exchange column in 6 M urea at pH 7.0. The CDB-C250 peak identified by SDS-PAGE was dialyzed and concentrated by lyophilization for further purification on a Sephadex G-75 gel filtration column at pH 7.0 in the presence of 6 M urea, 0.5 M KCl and 0.1 mM EDTA. The purified CDB-C250 peak was identified by SDS-PAGE, dialyzed to remove urea and salt, and lyophilized. The CDB-C250 protein expressed from the clone showed very high level expression in *E. coli*, indicating excellent compatibility with the host bacterium. The CDB-C250 clone provided a ready reagent for producing CDB-C250 in quantity in any of a variety of in vivo, or in vitro, contexts.

In view of the success of the clone encoding CDB-C250 to express robust levels of CDB-C250, and the unique antigenicity of CDB-C250 demonstrated hereinbelow, it is expected that polynucleotides comprising the coding region for CDB-C250, or a fragment thereof, such as a polynucleotide encoding at least 6, 7, 8, 9, 10, 15, 20, 25, 30, 40, 50, 60, 70, 80, 90, 100, 125, 150, 175, 200 or 225 amino acids, or a polynucleotide encoding an amino acid sequence of length equal to any whole integer between 6 and 250 amino acids, will be useful in producing CDB-C250 or a fragment (6-250 amino acids from the CDB-C250 region) thereof for use as a prophylactic or for use as a therapeutic in preventing or treating CDI. In particular, it is expected that polynucleotides encoding at least one of the eleven repeat elements (about 20 amino acids in length) are useful in producing, via expression, a polypeptide that will competitively inhibit the cytotoxigenic activity of *Clostridium difficile* toxin B and/or in serving as probes for nucleic-acid-based diagnostic assays for *Clostridium difficile* as the causative agent of CDI.

An effective practical approach to deliver a polypeptide according to the disclosure to the colon will be an important step in animal treatment for CDI. In humans, and in larger domesticated animals such as cattle, horses, goats, sheep, cats, dogs and the like, it may be delivered via encapsulated capsules. Administration by oral capsule would be difficult, if not impossible, in mice and hamsters, and may prove unwieldy or undesirable for larger non-human animals. As an alternative, an approach relying on an engineered form of secreting *Lactococcus lactis* is used as a cell factory for in situ treatment of disease in the colon. *L. lactis* is a non-pathogenic, non-invasive, non-colonizing Gram-positive bacterium, mainly used to produce fermented foods. Recombinant *L. lactis* strains are known to be safe and effective for the production and in vivo delivery of cytokines. The use of engineered *L. lactis* secreting interleukin-10 for the treatment of inflammatory bowel disease has rapidly moved to clinical trials. As a gram-positive bacterium, *L. lactis* has only one cellular membrane. This makes it an ideal host for protein secretion with subsequent membrane- or cell-wall-anchoring, or export into the fermentation medium. Another advantage is the low extracellular proteinase activity in lactococci.

The development of this safe system for in vivo delivery of biologically active proteins/peptides as therapeutic agents is suitable for the use of CDB-C250, or CDB-C250 fragments containing a repeat element, to treat CDI, particularly in animals such as humans. Using the commercially available pNZ expression plasmid vectors, DNA clones encoding CDB-C250 (and/or CDB-C250 fragments containing at least one repeat element shown in FIG. 2) are constructed for expressing and secreting these products. Since codon usage was found to be an important factor in the efficiency of expressing exogenous genes in *L. lactis* whose genomic DNA has a GC content of 35-37%, the various coding fragments will need to be engineered using synthetic nucleotides. DNA coding templates of this length have been engineered by us using nested sets of multiple pairs of synthetic nucleotides of about 150 nucleotides each. After chain extension reactions in a thermocycler to generate three double-stranded DNA fragments with overlapping end sequences (about 280 by each), two rounds of recombinant PCR will be carried out to join them into the 753-bp DNA coding template of CDB-C250, along with an NcoI cloning site at the 5' end of the coding region for CDB-C250 and a couple restriction cloning sites at the 3' end. To ensure sequence authenticity, the synthetic nucleotides are ordered as gel-purified full-length products.

PCR procedures are performed with proofreading polymerase and the final DNA insert constructed in the recombinant expression plasmids will be sequenced. During the cloning process, chloramphenicol sensitive, rec A+ strain of *E. coli*, such as MC1061, is used for the expression system. The CDB-C250 protein expression using the recombinant pNZ vectors is first carried out in *L. lactis* for protein purification and in vitro characterization. The transformation of *L. lactis* is accomplished using electroporation. Transformed cells will be examined for molecular weight, isoelectric point and Western blotting using anti-CDB-C250 monoclonal antibodies for authenticity. Large-scale expression will be performed following the instructions in the operating manual of the easy-to-operate and strictly controlled NICE® system (Bocascientific). The purification of CDB-C250 will be carried out as described above. It is worth noting that in comparison to the aerobically growing *B. subtilis*, which can secrete several grams of protein per liter, protein secretion in *Lactococcus* spp. is less substantial. This lower level of expression, however, is sufficient for testing relatively large-scale production of CDB-C250 in culture and therapeutic activity in vivo. To engineer a *L. lactis* strain that secretes CDB-C250 in the colon, the non-fusion CDB-C250-expressing pNZ vector is modified by adding the 27-amino-acid signal peptide of the major lactococcal-secreted protein Usp45 as a fusion peptide to the N-terminus of CDB-C250.

*L. lactis* expression and secretion of CDB-C250 protein is achieved in vivo in the mouse colon by administering to C57BL/6 mice, by intragastric inocula typically a daily dose (5-7 days total) of approximately $2 \times 10^7$ colony forming units of transformed *L. lactis*. The *L. lactis* is transformed with the recombinant pNZ plasmid or control *L. lactis* is transformed with the pNZ empty vector and/or heat-killed *L. lactis* control expressing CDB-C250. Three, five and seven days after the final dose, mice are euthanized (sodium pentobarbital or secobarbital) and the colon contents extracted for SDS-PAGE and Western blotting analysis of CDB-C250 using anti-CDB-C250 monoclonal antibodies to validate the delivery of CDB-C250 to the mouse colon. In this way, the quantitative level of production and the integrity of the CDB-C250 protein produced in situ in mouse colon are evaluated. When necessary, longer incubation times in the mice before *Clostridium difficile* challenge as well as additional doses of *L. lactis* inoculation are examined. Use of *L. lactis* to deliver polynucleotides encoding polypeptides according to the disclosure in a subject, such as a human, is contemplated as useful to prevent or treat CDI.

In addition to the foregoing discussion of polynucleotides encoding toxin B fragments or specifically hybridizing under stringent conditions thereto, the disclosure contemplates any pair of nucleic acid primers capable of specifically amplifying a 3' region of tcdB. The tcdB gene encodes *Clostridium difficile* toxin B. Suitable primers amplify the 3' region of tcdB encoding CDB-C250 or a fragment thereof, and the targeted amplification of the 3' end of tcdB as useful in diagnostic assays for the presence of *Clostridium difficile*, as well as being useful in methods of producing a polynucleotide encoding CDB-C250 or a fragment thereof. The primer pairs according to the disclosure will specifically hybridize to DNA targets, preferably through complete complementarity. The DNA targets the primer pairs are offset from each other by about 18-750 nucleotides, or more, provided that any amplified nucleic acid product containing the sequence between the two targets is capable of specifically hybridizing to the 3' region of *Clostridium difficile* tcdB.

Example 2

Comparison of Amino Acid Sequences of Toxin A and Toxin B

A comparison of the amino acid sequences of *Clostridium difficile* toxin A and *Clostridium difficile* toxin B was performed in view of the known problem (see, e.g., U.S. Patent Publication No. 20050287150) of cross-reactivities of binding partners to either of these two exotoxins of *Clostridium difficile*. The sequences were aligned to optimize similarity (i.e., gaps were introduced). In general, the length of a reference sequence aligned for comparison purposes is at least 50% of the length of that reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent homology between two sequences can be accomplished using a mathematical algorithm. The percent homology between two amino acid sequences is determined using the Needleman and Wunsch, J. Mol. Biol. 48:444-453, 1970, algorithm which has been incorporated into the GAP program in the GCG software package, using a Blossum 62 scoring matrix with a gap penalty of 12, a gap extend penalty of 4, and a frameshift gap penalty of 5.

A comparison of the amino acid sequences of *Clostridium difficile* toxin A and *Clostridium difficile* toxin B is shown in FIG. 1. Sequence comparisons were performed using the Clustal method in the Megalign program from DNAStar. The repeat motifs were identified and aligned manually based on amino acid identities. The Figure shows divergence at the C-terminal ends of the amino acid sequences, and the C-terminal region of 250 amino acids of *Clostridium difficile* toxin B (i.e., CDB-C250) was identified as the region within which toxin B-specific epitopes are located, i.e., epitopes unique to toxin B and not shared with toxin A. Also apparent in FIG. 1 is that an antibody recognizing an epitope in the aligned C-terminal region of 589 amino acids of toxin A would include regions of toxin B showing considerable similarity to toxin A, thereby producing a likely result of cross-reacting antibodies.

Continued analysis of the amino acid sequence of the C-terminal 250-amino-acid region of *Clostridium difficile* toxin B revealed several amino acid repeat structures expected to form toxin B-specific epitopes, and to participate in toxin B-specific epitopes. The amino acid sequences of these repeat sequences are presented in FIG. 2. Aligning the repeat sequences manually based on amino acid identities, eleven repeats of about 20 amino acids per repeat were identified (FIG. 2). The gross mapping of the functional domains of toxins A and B indicated that the C-terminal regions of both toxins contain the cell surface receptor binding site. This domain outlined for toxin B contains about 500 amino acids and only the C-terminal half, i.e., the CDB-C250 region, contains the repeating motifs (FIG. 2). In contrast to the cellular receptor in the C-terminal domain of toxin A, which has been extensively studied (Jank et al., Glycobiol. 17:15R-22R, 2007), very little is known for the cellular receptor domain of toxin B in colon epithelial cells. Consistent with the observation that toxin A and toxin B target different cell surface receptors (Stubbe et al., J. Immunol. 164:1952-60, 2000), their sequences in the C-terminal domains are significantly different (FIG. 1). This notion is further supported by the observation that multiple anti-CDB-C250 monoclonal antibodies do not cross react with toxin A. These features support our expectation that CDB-C250, and peptides comprising at least one of the repeat structures of the C-terminal 250-amino acid domain, are benign competitors of toxin B useful in the treatment and prevention of CDI. Moreover, binding partners, e.g., antibodies or antibody fragments, that specifically recognize or bind one or more peptides comprising at least one repeat structure of FIG. 2 are expected to be useful in detecting the presence of *Clostridium difficile* toxin B and, thereby, to be useful in diagnosing, preventing, or treating CDI.

Example 3

Characterization of CDB-C250

The cloned CBD-C250 protein showed very high level expression in *E. coli*, indicating excellent compatibility with the host bacterium. The purified CDB-C250 protein is highly soluble in physiological buffers as well as in water. From the unique amino acid sequence and the physicochemical properties of CBD-C250, it is apparent that this polypeptide is not only consistent with a toxin B-specific antigenic epitope comprising a plurality of smaller antigenic peptide sequences but also has properties indicative of therapeutic agent useful in countering the pathogenic effect of native toxin B, the exotoxin whose presence is correlated with CDI. Data disclosed in the following examples confirms that CDB-C250 is antigenic and is useful in diagnosing, preventing, and/or treating CDI in that it can elicit anti-toxin B-specific antibodies and can function itself as a toxin B competitor.

Various physicochemical analyses of the C-terminal 250-amino-acid region of *Clostridium difficile* toxin B were undertaken using accepted, conventional techniques. The molecular weight, isoelectric point, pH-charge titration curves and hydrophilicity profile were analyzed with DNAStar software. The molecular weight and pH-charge relationship were verified by SDS-PAGE and ion-exchange chromatography. The primary amino acid sequence of the CDB-C250 polypeptide is set forth in SEQ ID NO: 2; the primary amino acid sequence of intact toxin B is set forth in SEQ ID NO: 1. The molecular weight of the C-terminal polypeptide comprising the 250 C-terminal residues of *Clostridium difficile* toxin B was determined to be 29,000 daltons. This polypeptide has 14 strongly basic amino acids (Lys, Arg), 47 strongly acidic amino acids (Asp, Glu), 75 hydrophobic amino acids (Ala, Ile, Leu, Phe, Trp, and Val), and 79 polar amino acids (Asn, Cys, Gln, Ser, Thr, and Tyr). The isoelectric point of the C-terminal 250-amino-acid polypeptide of *Clostridium difficile* toxin B is 3.722. Considering the primary amino acid sequence and the physicochemical properties of the C-terminal polypeptide, it is apparent that this polypeptide is not only consistent with an antigenic polypeptide, but with a polypeptide comprising a plurality of smaller peptide sequences that are antigenic, such as the repeat structures identified in FIG. 2 and addressed in Example 2.

Peptide fragments of CDB-C250, including fragments containing at least one repeat element from the CDB-C250 region (repeat element sequences are shown in FIG. 2 and provided in SEQ ID NOS: 3-13), are expected to be useful in eliciting specific anti-toxin B antibodies and in competing with intact toxin B in prophylactic and therapeutic methods according to the disclosure.

Example 4

Elicitation of Monoclonal Antibodies Specific to Toxin B

Monoclonal antibodies in accordance with the disclosure were made by the hybridoma method first described by Kohler et al., (*Nature*, 256:495-7, 1975). Other methods of eliciting or generating mAbs are known in the art and may be used in preparing mAbs that specifically bind the C-terminal 250-amino-acid polypeptide of toxin B or a peptide thereof comprising a repeat sequence as set forth in FIG. 2. An exemplary alternative method for generating the antibodies is by recombinant DNA methods (see, e.g., U.S. Pat. No. 4,816, 567). The monoclonal antibodies may also be isolated from phage antibody libraries using the techniques described in, for example, Marks et al., *J. Mol. Biol.* 222:581-597 (1991).

Employing the hybridoma method, a mouse was immunized with the C-terminal 250-amino-acid polypeptide of *Clostridium difficile* toxin B to elicit lymphocytes that produce or are capable of producing antibodies that will specifically bind to the immunogen (i.e., the C-terminal 250-amino acid polypeptide of toxin B). Other mammals may also be used in generating mAbs according to the disclosure, such as a hamster or macaque monkey. Alternatively, lymphocytes may be immunized in vitro.

Following immunization, lymphocytes were fused with myeloma cells using polyethylene glycol as a fusing agent to form a hybridoma cell (see Coding, Monoclonal Antibodies: Principles and Practice, pp. 59-103 (Academic Press, 1986)). The hybridoma cells thus prepared were seeded and grown in hypoxanthine, aminopterin, and thymidine (HAT medium) culture medium that selected against unfused HGPRT-deficient myeloma cells.

Preferred myeloma cells are those that fuse efficiently, support stable high-level production of antibody by the selected antibody-producing cells, and are sensitive to a medium. Human myeloma and mouse-human heteromyeloma cell lines also have been described for the production of human monoclonal antibodies (Kozbor, *J. Immunol.,* 133: 3001 (1984); Brodeur et al., Monoclonal Antibody Production Techniques and Applications, pp. 51-63 (Marcel Dekker, Inc., New York, 1987)). Exemplary murine myeloma lines include those derived from MOP-21 and M.C.-11 mouse tumors available from the Salk Institute Cell Distribution Center, San Diego, Calif. USA, and SP2/0 or X63-Ag8-653 cells available from the American Type Culture Collection, Rockville, Md. USA.

Culture medium in which hybridoma cells were growing was assayed for production of monoclonal antibodies directed against the C-terminal 250-amino-acid polypeptide of toxin B. Preferably, the binding specificity of monoclonal antibodies produced by hybridoma cells is determined by immunoprecipitation or by an in vitro binding assay, such as a radioimmunoassay (RIA) or enzyme-linked immunosorbent assay (ELISA). The binding affinity of the monoclonal antibody can, for example, be determined by Scatchard analysis (Munson et al., Anal. Biochem., 107:220 (1980)).

After hybridoma cells that produce antibodies of the desired specificity, affinity, and/or activity, were identified, the identified clones were subcloned by limiting dilution procedures and grown by standard methods (coding, Monoclonal Antibodies: Principles and Practice, pp. 59-103 (Academic Press, 1986)). Culture media for this purpose include, for example, DMEM or RPMI-1640 medium. In addition, the hybridoma cells may be grown in vivo as ascites tumors in an animal. The monoclonal antibodies secreted by the subclones are separated from the culture medium, ascites fluid, or serum by conventional immunoglobulin purification procedures such as, for example, protein G-Sepharose, hydroxylapatite chromatography, gel electrophoresis, dialysis, or affinity chromatography.

It is further contemplated that antibodies of the disclosure may be used or smaller antigen binding fragments of the antibody, which are well-known in the art and described herein, may be used in the methods according to the disclosure.

Example 5

Western Blot Analysis

The specificity of the binding of the monoclonal anti-CDB-C250 antibody was assessed by Western blot, using conventional techniques. Separate blots were prepared for the monoclonal anti-CDB-C250 antibodies secreted into the culture supernatant by each of the hybridomas generated in Example 4, i.e., 1C11, 2C10, 3E1, 3G8, 3H10 and 4B3. Each blot contained purified CDB-C250, a crude lysate of a strain of *Clostridium difficile* (ATCC 9689) that expresses toxin late in the growth cycle at a lower level (Rolfe, et al., Infection and Immunity, 25:191-201, 1979), and a crude lysate of a pathogenic strain of *Clostridium difficile* (ATCC 43255) that hyper-produces toxins A and B early in the growth phase (Murray et al., BMC Infectious Diseases 9:103 doi:10.1186/1471-2334-9-103, 2009). As shown in FIG. 3, each of the anti-CDB-C250 mAbs specifically bound to purified CDB-C250, although the polypeptide ran as a smear in the SDS-PAGE used to fractionate proteins. Without wishing to be bound by theory, one logical explanation for the smear is that CDB-C250 has a relatively high negative charge at neutral pH and weak binding to SDS. Also of note, the anti-CDB-C250 mAbs bound to intact toxin B in the hyper-producing strain, as expected, but not to intact toxin A, and this binding pattern was the same in both strains. There was no signal for toxin B in the ATCC 9689 strain, but this was not surprising based on the fact that the antibody preparations were crude antibody lysates and the ATCC 9689 strain is not a robust producer of toxin B in vitro. The results demonstrate that the monoclonal antibodies raised by immunization with the C-250 polypeptide fragment of *Clostridium difficile* toxin B recognized intact toxin B. In addition, the epitope structures recognized are stable after SDS-PAGE and Western blotting.

Example 6

In Vitro Cytotoxicity Testing

Early evaluations of CDB-C250 protein expressed in *E. coli* used protein that was effectively purified to homogeneity. From stocks of lyophilized product, the protein was diluted in physiological buffer and applied in cell culture studies. Using three strains of *Clostridium difficile* and exposing CDB-C250 to undefined titers of toxin B supernatant obtained from *Clostridium difficile* cultured in anaerobic chopped meat broth demonstrated that one strain was unaffected in its in vitro action in cell culture, one strain's toxin was partially affected by CDB-C250, and one strain demonstrated definitive inhibition of toxin activity. Thus, the data relating to CDB-C250 establish the potential of CDB-C250 to directly block the cytotoxic effect of *C. difficile* toxin B.

One of the assays for production of *Clostridium difficile* toxin B in its various forms, and in particular CDB-C250, is an in vitro assay for cytotoxicity. *Clostridium difficile* strains are grown to purity, then 3 to 5 colonies are selected and inoculated into anaerobic broth and incubated at 35-37° C. for 3 to 7 days. Cytotoxin testing is performed with the TechLab *C. DIFFICILE* TOX-B (Toxin/Antitoxin) Kit (TechLab, Blacksburg, Va.). The *C. DIFFICILE* TOX-B TEST relies on a tissue culture format to detect cytotoxic activity, in the form of cell rounding, in fecal specimens. The test identifies *Clostridium difficile* toxin B by using specific anti-toxin. Testing on isolated *Clostridium difficile* colonies is performed using 2-3 mLs of anaerobic chopped-meat glucose broth suspension grown with *Clostridium difficile* and then centrifuged at 4,000×g for 10 minutes and subsequently filtered through a 0.45 μm Spin-X filter. To determine the presence of toxin, two tubes of MRC-5 cells (ViroMed Laboratories) are set up for each sample. Sample alone and sample plus anti-toxin are tested with the TechLab *Clostridium difficile* Tox-B (Toxin/Antitoxin) Kit. Test results are determined after 24 hours and 48 hours of incubation, according to the manufacturer's instructions. The sample is considered toxigenic if a cytopathic effect (CPE) is observed in the toxin tube and not in the tube containing added anti-toxin. The in vitro cytotoxicity assay is amenable to the assessment of toxin B production by *Clostridium difficile* isolates, such as *Clostridium difficile* isolates from patient stool samples. In addition, an ELISA or a modification of the in vitro cytotoxicity assay are useful in assessing the cytotoxiciy of the various recombinantly produced toxin B proteins, peptides or peptide fragments, e.g., CDB-C250. In testing toxin B proteins, routine optimization will reveal the quantity of protein to use in an ELISA or to add to the TOX-B kit reagents to obtain reliable assay results, and the assay can be performed without the need for cell culturing.

An in vitro assay is also available to optimize dosages of the toxin B peptide fragments (CDB-C250, toxin B C-terminal repeat-containing peptides) and of the specific anti-toxin B antibodies. To optimize the dosage of a toxin B fragment, for example, subspecies *typing* of 100 strains of *Clostridium difficile* collected from unique patients will be performed using REA and PFGE to define the strain genotypes. The strategy is to select 20 unique strain types representative of those most common in current US circulation and measure their capacity for toxin production after 5 days incubation in anaerobic chopped-meat glucose broth. Five days is chosen so that toxin production is complete and thus permits reproducibility of the experiments over time. The toxin titer chosen for use in this portion of the analysis will be such that each strain's diluted toxin demonstrates 50% destruction of the tissue cells at 48 hours when diluted 1:100 with growth medium. A toxin B fragment such as CDB-C250 protein will then be tested at serially defined concentrations so that the action of toxin B is blocked in at least 80% of the 20 tested *Clostridium difficile* strains. One of skill in the art will recognize that there are alternative approaches to dosage determination and optimization known in the art, and each of these approaches is contemplated as suitable for use with the diagnostic, prophylactic and therapeutic compounds disclosed herein.

Example 7

Testing *Clostridium Difficile* in a Mouse Model

Another measure of the production of *Clostridium difficile* toxin B in it many forms, e.g., CDB-C250, uses a mouse model. This model was chosen as one of two animal models for use because it relatively closely resembles the full spectrum of human disease in that acute diarrhea as well as chronic diarrhea are represented, and it presents the opportunity for investigating new drug therapy (Steidler et al., Science 289(5483):1352-1355 (2000)). This mouse model is used to assess the prevention of CDI as well as the treatment of CDI using toxin B peptides and fragments, such as CDB-C250 or any of the peptides containing at least one of the repeat motifs found in CDB-C250. As a consequence, animals are tested by administering the polypeptide at the inception of experimental CDI as well as one day into the onset of disease. Following the method of Chen and colleagues (Chen et al., Gastroenterol. 135:1984-92, 2008), 9-week-old C57BL/6 female mice are each treated with an antibiotic mixture consisting of kanamycin (0.4 mg/mL), gentamicin (0.035 mg/mL), colistin (850 U/mL), metronidazole (0.215 mg/mL), and vancomycin (0.045 mg/mL) in drinking water for 3 days before clindamycin and *C. difficile* challenge. Clindamycin is administered after a single day of regular water for drinking as a single dose (10 mg/kg) intraperitoneally 1 day before *C. difficile* challenge. Animals are infected by gavage with strains of *C. difficile* and monitored for signs of disease such as diarrhea, hunched posture, wet tail, and weight loss for 10-14 days.

Histopathologic study is done on approximately 50% of the study animals to obtain a valid observation as to the consistent nature of the represented disease. Histologic examination of colonic tissues in mice exposed to *Clostridium difficile* is expected to demonstrate proliferative ulcerative enteritis with superficial epithelial necrosis and release of inflammatory exudates and necrotic cellular material into the intestinal lumen, as known in the art. Additional indications of CDI are extensive submucosal edema without submucosal inflammation and patchy epithelial necrosis, mucosal proliferation, with the presence of inflammatory cells, as is described for human *Clostridium difficille*-associated colitis.

Example 8

Testing *Clostridium Difficile* in a Hamster Model

The second animal model used to measure *Clostridium difficile* toxin B production in its several forms, including but not limited to CDB-C250 or any of the peptides containing at least one repeat motif from the CDB-C250 region of toxin B (see FIG. 2), is that of the well-described Syrian Hamster model (Steidler et al., Science 289(5483):1352-1355 (2000), Bermudez-Humaran, Hum. Vacc. 5:264-7 (2009), van Asseldonk et al., Gene 95:155-160 (1990)), following the method described by Razaq and colleagues (van Asseldonk et al.). The rationale for using this model as the second model is that it has become the standard for testing susceptibility to acute CDI disease after antibiotic administration, and the model is recognized by the FDA. This model is useful to assess the ability of CDB-C250 to protect against CDI. Therefore, the polypeptide is only administered at (or before) the inception of CDI and results are compared to controls. *Clostridium difficile* is inoculated anaerobically onto pre-reduced blood agar plates and incubated at 37° C. until colonies are confluent. The plates are maintained for 3 days to maximize sporulation. The organisms are then harvested, placed into 10 mL of phosphate-buffered saline (PBS) without added calcium or magnesium, washed in PBS, and heat-shocked at 56° C. for 10 minutes to kill surviving vegetative cells. The spores are centrifuged and resuspended in Dulbecco's Modified Eagle Medium (DMEM), aliquotted, and frozen at −80° C. The frozen spores are quantitated before use by plating 100 μL of 10-fold serial dilutions of the spores onto taurocholate fructose agar plates. Spores are diluted in DMEM for orogastric inoculation into hamsters. One μL of food coloring is added to the inoculum for ease of visibility to ensure that hamsters receive the entire dose. For each isolate, hamsters are given 1 dose of clindamycin orogastrically (30 mg/kg) on day 0, to establish susceptibility to CDI. This is followed on day 5 by gastric inoculation with 100 colony-forming units of the designated *Clostridium difficile* spores. Immediately preceding treatment with clindamycin, bedding is changed, and fecal pellets are collected for culture on *Clostridium difficile* selective medium. This is done to confirm that hamsters were not colonized with *Clostridium difficile* before the administration of clindamycin. Hamsters are monitored for signs of *Clostridium difficile* infection that include stiffness, lying prone, wet tail, diarrhea, and death. Hamsters found lying prone or unresponsive are euthanized.

Histopathologic study is performed on approximately 50% of the study to obtain a valid observation as to the consistent nature of the represented disease. As with the mice, we will assess the comparison of CDB-C250 polypeptide-treated animals (with no prior antimicrobial or *Clostridium difficile* exposure) to controls so as to demonstrate no adverse effect of the therapy on the colonic mucosa.

Example 9

Further Testing of Antibodies Specific to Toxin B

Additional work was carried out on monoclonal antibodies raised against CDB-C250 to determine their reactivities to toxin B from various strains of toxigenic *Clostridium difficile*. After preliminary evaluation of the six monoclonal antibodies identified in Example 5, monoclonal antibody 3H10 was identified as demonstrating good immunoreactivity against toxin B and the best neutralization of toxin B cytotoxicity. As a result, 3H10 from ascites fluid (2.3 mg of purified mAb from 1 mL fluid) was affinity purified on a toxin B column. The original hybridoma supernatant concentration was about 23 μg/mL. The purified 3H10 antibody was tested for immunoreactivity and found to have a positive reaction to native toxin B at antibody dilutions of $10^{-6}$ to $10^{-7}$. These data correspond to an antibody concentration of about 1 ng/mL and a binding affinity of $1.8 \times 10^{11}$ M$^{-1}$. The mAb was also tested for specificity using an ELISA assay. The 3H10 mAb did not react with purified native toxin A. By immunoblotting, 3H10 was found to react also with denatured toxin B.

Additional experiments were performed to test the capacity of 3H10 to neutralize toxin B in tissue-culture cell-rounding assays. Undiluted (500 μg/mL per assay well) purified antibody showed complete neutralization of cell rounding caused by a $10^{-7}$ dilution of toxin B and partial neutralization of rounding caused by a $10^{-6}$ dilution of toxin B.

A biotinylated 3H10 mAb was also conjugated to plates coated with Streptavidin to yield Streptavidin:biotin-3H10. Both 0.5 and 1 μg/well 3H10-biotin showed equivalent ability to capture toxin B as a toxin A/B II polyclonal antibody mix developed at TECHLAB.

These new data add convincing evidence that the CDB-C250 peptide represents a highly specific domain structure of toxin B with an important role in cytotoxicity. This confirmation further justifies the expectation that CDB-C250 peptide, and peptides comprising at least one repeat motif from the CDB-C250 domain of toxin B, will provide effective prophylaxis and/or treatment of CDI in subjects, including human patients and non-human animals.

Example 10

Clostridium Difficile Strains

Each *Clostridium difficile* strain is plated to a pre-reduced cycloserine-cefoxitin-fructose agar (CCFA-VA formulation) and anaerobic blood agar media. Plates are then incubated anaerobically at 35-37° C. for up to 72 hours to assure purity of the strains. Colonies are confirmed by Gram stain, aerotolerance, and a Pro-disk test (Key Scientific). Two methods are available to ensure that the growth and handling of various *Clostridium difficile* species do not lead to confusion and to ensure that there is no uncertainty in the classification of the *Clostridium difficile* genotypes. Restriction Endonuclease Analysis (REA) typing is one standardized method that is performed, e.g., with the HindIII restriction enzyme, as would be known in the art. Briefly, brain-heart-infusion broth is inoculated with 3-5 colonies from an anaerobic blood agar plate and then incubated overnight. Cells are washed in TE (10 mM Tris-HCl, 1 mM EDTA [pH 8.0]), re-suspended in 0.1 mL of TE with lysozyme (50 mg/mL; Sigma-Aldrich), incubated for 30 min at 35° C., mixed with 0.5 mL of GES solution (guanidine thiocyanate, 0.6 g/mL; EDTA, 100 mM; sarcosyl, 0.5%, vol/vol), incubated for 10 minutes at room temperature, mixed with 0.75 mL of ammonium acetate (7.5 M), and held on ice for 10 minutes. DNA is extracted with phenol:chloroform:isoamyl alcohol (25:24:1) and precipitated with cold 2-propanol. For restriction digestion, DNA (10 to 20 RID is incubated with HindIII (Bethesda Research Laboratories, Gaithersburg, Md.) according to the manufacturer's recommendations, except that 20 U of enzyme is used and 3 RI of spermidine (100 μg/mL; Sigma) is added. The resulting restriction fragments are resolved in a 0.7% agarose gel and the gel is then stained with ethidium bromide and photographed under UV light, producing a characteristic banding pattern for each isolate that is visually compared with the patterns of previously identified REA types. Isolates are categorized into groups (letter designation) if the patterns had <6 band differences (similarity index >90%) and into specific types (number designation following the group letter) based on unique, identical REA patterns.

Pulsed-Field Gel Electrophoresis (PFGE) is another standard method for *Clostridium difficile* genotyping and is accomplished following standard methods. Briefly, isolates are inoculated into pre-reduced brain-heart-infusion broth and incubated at 37° C. The optical density is monitored with a spectrophotometer. When growth reaches mid-exponential phase (about 0.5 OD$_{540}$), typically, about 7 hours after inoculation, the organisms are collected by centrifugation at 4° C. and then processed for DNA using conventional methods. *Clostridium difficile* DNA in agarose is digested with SmaI (New England Biolabs, Cambridge, Mass.), and the resulting macrorestriction fragments are resolved by PFGE. The gels are electrophoresed for 22 hours in a contour-clamped homogeneous electric field apparatus (CHEF DR11; Bio-Rad, Richmond, Calif.) at 6.0 V/cm, with initial and final switch times of 20 and 70 s, respectively, and linear ramping. The gels are stained with ethidium bromide and photographed under UV light. SmaI-digested *S. aureus* DNA (ATCC 8325) is used as a molecular weight size standard.

Example 11

Detection of Tropomyosin in Stool Samples from Patients with CDAD

To determine if host proteins, i.e., colonic epithelial cytoskeleton proteins, or fragments thereof, were present at an elevated level in stool samples from patients with *Clostridium difficile* disease, human non-muscle tropomyosin, a major component of the actin cytoskeleton, was measured in stool samples from patients positive for *Clostridium difficile* toxin B by PCR.

Two grams of stool sample from a watery or loose stool were brought to 10 mL volume in ddH$_2$O and boiled for 10 minutes, cooled on ice for 20 minutes, and spun at 6,000×g at 4° C. for 20 minutes to remove a majority of insoluble material. The supernatant was further clarified by centrifugation at 12,000×g at 4° C. for 30 minutes. The clean supernatant was then subjected to isoelectric point precipitation to enrich the sample for tropomyosin. With the pH of the solution monitored by a pH meter, sample pH was adjusted to 4.6 with hydrochloric acid (0.1 N) and subjected to additional centrifugation at 12,000×g at 4° C. for 30 minutes to collect tropomyosin in the pellet. Samples were analyzed by SDS-PAGE and Western blotting using specific anti-tropomyosin monoclonal antibodies using conventional methods (Hossain et al., J. Biol. Chem. 280:42442-53, 2005).

Eleven different patient samples were analyzed in parallel by SDS-polyacrylamide gel electrophoresis and Western blot analysis using a mixture of anti-tropomyosin 1-5 monoclonal antibodies, (CH1 (control), LC1 (against isoform TM5); and LC24 (against isoform TM4). Protein extracts from human epithelial cell culture were used as positive control and chicken leg muscle extracts were used as a control to exclude food protein (e.g., muscle tropomyosin) residues.

The results showed detection of non-muscle tropomyosin and non-muscle tropomyosin fragments in samples positive for *Clostridium difficile*. Results of this study demonstrated an increased release, i.e., elevated level, of non-muscle tropomyosin in stool samples from patients with CDAD. No tropomyosin was detected in negative controls. Without being bound by theory, the low molecular weight non-muscle tropomyosin fragments detected in *Clostridium difficile*-diarrhea stool samples provide a more specific target for assessing host response to CDI, leading to improved clinical diagnosis.

Example 12

Detection of *Clostridium Difficile* Toxin B

In addition to testing for host response, i.e., host proteins, as described in Example 1, the disclosure includes methods for detecting the presence of the microbial target tcdB. To test for the presence of tcdB in the host, a subject's stool sample is tested for the presence of tcdB DNA, RNA, or protein.

Testing for tcdB is carried out by cytotoxicity assay, toxigenic culture, immunoassay, RT-PCR, PCR, real-time PCR, or any suitable technique known in the art. Immunoassays include, but are not limited to, Western blot analysis, immunohistochemistry, immunofluorescence, ELISA, and EIA. Testing for the presence of the CDB-250 polypeptide, or a fragment thereof, or for the presence of CDB-750 DNA (a region of tcdB comprising 750 nucleotides in length at the 3' end of the tcdB coding region encoding CDB-250), or a fragment thereof, provides a suitable means for detecting the presence of the microbial target.

The assays developed for nucleic acid detection of tcdB were carried out on a wide variety of clinical specimens and necessitated optimizing pre-analytical sample preparation approaches in order to maximize target recognition. A PCR test is considered a sensitive and reliable test for detection of toxigenic *Clostridium difficile*. Several real-time PCR assays are commercially available for the detection of tcdB.

Example 13

Additional Methods for the Detection of Clostridium Difficile Toxin B

Monoclonal antibodies (mAbs) were raised against CDB-C250 and are described herein above in detail. These CDB-C250-specific mAbs were sent to TECHLAB®, Inc. for testing to determine their reactivity against toxin B from various strains of toxigenic *Clostridium difficile*.

Monoclonal antibody (mAb) 3H10 was selected from among six mAbs after preliminary evaluation, based on having the best neutralization of toxin B cytotoxicity and good immunoreactivity. Following this, 3H10 from ascites fluid (2.3 mg purified mAb from 1 mL) was affinity-purified on a toxin B column. The original hybridoma supernatant concentration was about 23 µg/mL. The purified 3H10 was tested for immunoreactivity and found to have a positive reaction to native toxin B at antibody dilution of $10^{-6}$ to $10^{-7}$, which represents about 1 ng/mL and an affinity of about $1.8 \times 10^{-11}$ M. The mAb was also tested for specificity using an ELISA assay. The 3H10 mAb did not react with purified native toxin A. By immunoblotting, 3H10 was also found to react with denatured toxin B.

Experiments were further carried out to test the capacity of 3H10 to neutralize toxin B in tissue culture cell rounding assays. Undiluted (500 µg/mL per assay well) purified antibody showed complete neutralization of cell-rounding caused by a $10^{-7}$ dilution of toxin B and partial neutralization of rounding caused by a $10^{-6}$ dilution.

Additionally, 3H10 was conjugated to plates coated with Streptavidin:Biotin-3H10. Both 0.5 and 1 µg/well 3H10-biotin showed equivalent ability to capture toxin B as a toxin A/B II polyclonal antibody mix developed at TECHLAB®. These new data add convincing evidence that the CDB-250 peptide represents a highly specific domain structure of toxin B, playing a critical role in cytotoxicity.

The disclosure has been described in terms of particular embodiments found or proposed to comprise specific modes for the practice of the subject matter of the disclosure. Various modifications and variations of the described disclosure will be apparent to those skilled in the art without departing from the scope and spirit of the disclosure. Although the disclosure has been described in connection with specific embodiments, it should be understood that the subject matter of the disclosure as claimed should not be unduly limited to such specific embodiments. Indeed, various modifications of the described modes for carrying out the disclosure that would be apparent to those skilled in the relevant fields are intended to be within the scope of the following claims.

What is claimed is:

1. A method of diagnosing *Clostridium difficile*-associated diarrhea (CDAD) or *Clostridium difficile* infection (CDI) in a stool specimen of a subject, the method comprising detecting in the stool specimen an increase in a level of a non-muscle tropomyosin polypeptide, or fragment thereof, with an antibody, or antigen-binding portion thereof, that specifically binds the non-muscle tropomyosin polypeptide, or fragment thereof; and detecting the presence of a C-terminal 250-amino-acid fragment of *Clostridium difficile* toxin B polypeptide comprising the amino acid sequence set forth in SEQ ID NO: 2, or fragment thereof, with an antibody, or antigen-binding portion thereof, that specifically binds the C-terminal 250-amino-acid fragment of *Clostridium difficile* toxin B polypeptide comprising the amino acid sequence set forth in SEQ ID NO: 2, or fragment thereof,
wherein the increase in the level of the non-muscle tropomyosin polypeptide, or fragment thereof, and the presence of the C-terminal 250-amino-acid fragment of *Clostridium difficile* toxin B polypeptide comprising the amino acid sequence set forth in SEQ ID NO: 2, or fragment thereof, is diagnostic for CDAD or CDI in the subject.

2. The method of claim 1, the method further comprising detecting a *Clostridium difficile* toxin A polypeptide, or fragment thereof, with an antibody, or antigen-binding portion thereof, that specifically binds the *Clostridium difficile* toxin A polypeptide, or fragment thereof.

3. The method of claim 1, wherein the non-muscle tropomyosin is selected from the group consisting of non-muscle tropomyosin 1, non-muscle tropomyosin 2, non-muscle tropomyosin 4, and non-muscle tropomyosin 5.

4. The method of claim 1, wherein the antibody, or antigen-binding portion thereof, that specifically binds the C-terminal 250-amino-acid fragment of *Clostridium difficile* toxin B polypeptide comprising the amino acid sequence set forth in SEQ ID NO: 2, or fragment thereof, also specifically binds to a polypeptide comprising the sequence selected from the group consisting of SEQ ID NOS: 3-12 and 13.

5. The method of claim 1, wherein the antibody, or antigen-binding portion thereof, that specifically binds the C-terminal 250-amino-acid fragment of *Clostridium difficile* toxin B polypeptide comprising the amino acid sequence set forth in SEQ ID NO: 2, or fragment thereof, comprises:
   (a) a heavy chain CDR1 amino acid sequence selected from the group consisting of SEQ ID NOS: 39, 42, 45, 48, and 51;
   (b) a heavy chain CDR2 amino acid sequence selected from the group consisting of SEQ ID NOS: 40, 43, 46, 49, and 52; and
   (c) a heavy chain CDR3 amino acid sequence selected from the group consisting of SEQ ID NOS: 41, 44, 47, 50, and 53.

6. The method of claim 5 wherein at least one of the heavy chain CDR1, CDR2 or CDR3 amino acid sequences is a consensus sequence for CDR1, CDR2, or CDR3, respectively, as set forth in SEQ ID NO: 60.

7. The method of claim 1, wherein the antibody, or antigen-binding portion thereof, that specifically binds the C-terminal 250-amino-acid fragment of *Clostridium difficile* toxin B polypeptide comprising the amino acid sequence set forth in SEQ ID NO: 2, or fragment thereof, comprises:
   (a) a light chain CDR1 amino acid sequence selected from the group consisting of SEQ ID NOS: 25, 27, 30, 33, and 36;
   (b) a light chain CDR2 amino acid sequence selected from the group consisting of SEQ ID NOS: 26, 28, 31, 34, and 37; and
   (c) a light chain CDR3 amino acid sequence selected from the group consisting of SEQ ID NOS: 29, 32, 35, and 38.

8. The method of claim 7 wherein at least one of the light chain CDR1, CDR2 or CDR3 amino acid sequences is a consensus sequence for CDR1, CDR2, or CDR3, respectively, as set forth in SEQ ID NO: 61.

9. A kit for diagnosing *Clostridium difficile*-associated diarrhea (CDAD) or *Clostridium difficile* infection (CDI) in a stool specimen comprising (a) a first reagent comprising an antibody, or antigen binding portion thereof, that specifically binds a non-muscle tropomyosin, or fragment thereof; and (b) a second reagent comprising an antibody, or antigen binding portion thereof, that specifically binds a C-terminal 250-amino-acid fragment of *Clostridium difficile* toxin B polypeptide comprising the amino acid sequence set forth in SEQ ID NO: 2, or fragment thereof; and optionally, instructions for using the reagents to make a diagnosis of CDAD or CDI.

10. The kit of claim 9 further comprising a third reagent comprising an antibody, or antigen binding portion thereof, that specifically binds a *Clostridium difficile* toxin A polypeptide, or fragment thereof.

11. The kit of claim 9, wherein the non-muscle tropomyosin is selected from the group consisting of non-muscle tropomyosin 1 (TM1), non-muscle tropomyosin 2 (TM2), non-muscle tropomyosin 4 (TM4), and non-muscle tropomyosin 5 (TM5).

12. The kit of claim 9, wherein the antibody, or antigen binding portion thereof, that specifically binds the C-terminal 250-amino-acid fragment of *Clostridium difficile* toxin B polypeptide comprising the amino acid sequence set forth in SEQ ID NO: 2, or fragment thereof, also specifically binds to a polypeptide comprising the sequence selected from the group consisting of SEQ ID NOS: 3-12 and 13.

13. The kit of claim 9, wherein the antibody, or antigen binding portion thereof, that specifically binds the C-terminal 250-amino-acid fragment of *Clostridium difficile* toxin B polypeptide comprising the amino acid sequence set forth in SEQ ID NO: 2, or fragment thereof, comprises:

(a) a heavy chain CDR1 amino acid sequence selected from the group consisting of SEQ ID NOS: 39, 42, 45, 48, and 51;
(b) a heavy chain CD2 amino acid sequence selected from the group consisting of SEQ ID NOS: 40, 43, 46, 49, and 52; and
(c) a heavy chain CDR3 amino acid sequence selected from the group consisting of SEQ ID NOS: 41, 44, 47, 50, and 53.

14. The kit of claim 9, wherein the antibody, or antigen binding portion thereof, that specifically binds the C-terminal 250-amino-acid fragment of *Clostridium difficile* toxin B polypeptide comprising the amino acid sequence set forth in SEQ ID NO: 2, or fragment thereof, comprises:
(a) a light chain CDR1 amino acid sequence selected from the group consisting of SEQ ID NOS: 25, 27, 30, 33, and 36, or a consensus sequence thereof;
(b) a light chain CDR2 amino acid sequence selected from the group consisting of SEQ ID NOS: 26, 28, 31, 34, and 37, or a consensus sequence thereof; and
(c) a light chain CDR3 amino acid sequence selected from the group consisting of SEQ ID NOS: 29, 32, 35, and 38, or a consensus sequence thereof.

15. The kit of claim 13, wherein at least one of the heavy chain CDR1, CDR2 or CDR3 amino acid sequences is a consensus sequence for CDR1, CDR2, or CDR3, respectively, as set forth in SEQ ID NO: 60.

16. The kit of claim 14, wherein at least one of the light chain CDR1, CDR2 or CDR3 amino acid sequences is a consensus sequence for CDR1, CDR2, or CDR3, respectively, as set forth in SEQ ID NO: 61.

* * * * *

UNITED STATES PATENT AND TRADEMARK OFFICE
CERTIFICATE OF CORRECTION

| | |
|---|---|
| PATENT NO. | : 8,906,635 B2 |
| APPLICATION NO. | : 13/978965 |
| DATED | : December 9, 2014 |
| INVENTOR(S) | : Jian-Ping Jin et al. |

Page 1 of 1

It is certified that error appears in the above-identified patent and that said Letters Patent is hereby corrected as shown below:

In the Claims:

At Column 95, line 4, "CD2" should be -- CDR2 --.

Signed and Sealed this
Twenty-fourth Day of November, 2015

Michelle K. Lee
*Director of the United States Patent and Trademark Office*